United States Patent [19]

Hunt

[11] 4,206,120
[45] Jun. 3, 1980

[54] OXAAZABICYCLOHEPTANE ANTIBIOTICS

[75] Inventor: Eric Hunt, Reigate, England

[73] Assignee: Beecham Group Limited, Great Britain

[21] Appl. No.: 763,866

[22] Filed: Jan. 31, 1977

[30] Foreign Application Priority Data

Feb. 4, 1976 [GB] United Kingdom ............... 4320/76
Mar. 4, 1976 [GB] United Kingdom ............... 8597/76
Apr. 14, 1976 [GB] United Kingdom ............. 15346/76
Jun. 11, 1976 [GB] United Kingdom ............. 24227/76

[51] Int. Cl.² .................. C07D 498/04; A61K 31/42
[52] U.S. Cl. .............................. 260/245.3; 424/272;
260/239 A; 260/340.9 R; 542/420; 542/437;
542/444; 260/330.3
[58] Field of Search .................. 260/307 FA; 424/272

[56] References Cited
FOREIGN PATENT DOCUMENTS 2616087 10/1976 Fed. Rep. of Germany .... 260/307 FA Primary Examiner—Mark L. Berch
Attorney, Agent, or Firm—Jacobs & Jacobs

[57] ABSTRACT

Compounds of the formula (I):

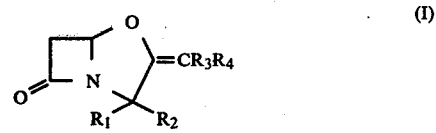

wherein $R_1$ is hydrogen, lower alkyl, hydroxymethyl or phenyl; $R_2$ is hydrogen, lower alkyl or an optionally salted or esterified carboxyl group; $R_3$ is hydrogen, chlorine, opticnally substituted alkyl or a conjugating group; and $R_4$ is a conjugating group, $CH_2OH$ or $CH(OH)CH_3$; are useful for their $\beta$-lactamase inhibitory activity and are also useful in symergistic combinations with penicillins or cephalosporins.

19 Claims, No Drawings

OXAAZABICYCLOHEPTANE ANTIBIOTICS

The present invention relates to new β-lactam containing compounds, to their pharmaceutical compositions and to a process for their preparation.

Many strains of bacteria owe their resistance to conventional penicillins and cephalosporins to their production of β-lactamase. Inhibition of such enzymes by a novel naturally occurring β-lactamase inhibitor has been described in Belgian Patent No. 827926.

A group of synthetic compounds has now been discovered that inhibit a number of β-lactamases and so enhance the effectiveness of penicillin and cephalosporin derivatives against a range of β-lactamase producing gram-positive and gram-negative bacteria.

Accordingly the present invention provides compounds of the formula (I):

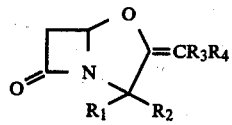

wherein $R_1$ is a hydrogen atoms or a lower alkyl, hydroxymethyl or phenyl group; $R_2$ is a hydrogen atom or a lower alkyl group or an optionally salted or esterified carboxyl group; $R_3$ is a hydrogen or chlorine atom or an optionally substituted alkyl group or a conjugating group and $R_4$ is a conjugating group or a $CH_2OH$ or $CH(OH)CH_3$ group.

When used herein the term 'conjugating group' means a group which contains an unsaturated atom linked directly to the olefinic carbon atom shown in the compound of the formula (I). Suitable conjugating groups include $NO_2$, $CN$, alkenyl, alkynyl, aryl, $CO.R_5$, $CO_2R_6$, $SOR_7$, $SO_2R_7$, $CONR_8R_9$ and the like wherein $R_5$ is a hydrogen atom or an optionally substituted hydrocarbon group, $R_6$ is a hydrogen atom, a salting ion, an optionally substituted hydrocarbon group, $R_7$ is an optionally substituted hydrocarbon group, $R_8$ is a hydrogen atom or a hydrocarbon group and $R_9$ is a hydrogen atom or an optionally substituted hydrocarbon group.

When used herein the term 'alkenyl group' means a vinyl group or a vinyl group substituted by a hydrocarbon group and the term 'alkynyl group' means an ethynyl group or an ethynyl group substituted by a hydrocarbon group. When used herein the term 'lower' means that the group contains up to 4 carbon atoms. When used herein the term 'aryl' includes phenyl and substituted phenyl groups and 5- and 6- membered heterocyclic rings of up to 4 heteroatoms such as the thienyl and furyl groups. Particularly suitable 'aryl' groups include phenyl, hydroxyphenyl, thienyl and furyl groups. When used herein the term 'optionally substituted' means unsubstituted or substituted by halogen, hydroxyl, etherified hydroxyl, acrylated hydroxyl, aryl, acyl, carboxyl, salted carboxyl or etherified carboxyl group.

Herein, unless stated otherwise, a generically named group will contain not more than 9 carbon atoms and will more suitably contain not more than 6 carbon atoms.

One particularly suitable group of compounds of the formula (I) is that of the formula (II):

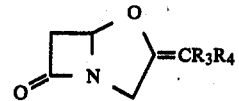

wherein $R_3$ and $R_4$ are as defined in relation to formula (I) except that $R_4$ is not $CH_2OH$ or $CH(OH)CH_3$.

A further particularly suitable group of compounds of the formula (I) is that of the formula (III):

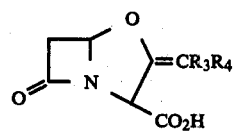

and salts and esters thereof wherein $R_3$ and $R_4$ are as defined in relation to formula (I) except that $R_4$ is not $CH_2OH$ or $CH(OH)CH_3$.

One favoured value for $R_3$ in the compounds of the formulae (II) and (III) is the hydrogen atom. Other further favoured values for $R_3$ include the lower alkyl groups such as the methyl, ethyl and n-propyl groups.

Favoured values for $R_4$ in the compounds of the formulae (II) and (III) include $NO_2$, $CN$, aryl, optionally salted or esterified $CO_2H$ or a $COR_5$ group where $R_5$ is a hydrogen atom or an optionally substituted hydrocarbon group.

Certain particularly suitable values for $R_4$ include (a) optionally salted or esterified $CO_2H$ groups, (b) $COR_5'$ where $R_5'$ is a hydrocarbon group and (c) aryl groups.

One group of particularly useful compounds of this invention is that of the formula (IV):

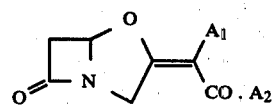

wherein $A_1$ is a hydrogen atom or a methyl, ethyl, phenyl or thienyl group and $A_2$ is an optionally substituted hydrocarbon group.

More suitably $A_1$ is a methyl group. Suitably $A_2$ is an unsubstituted hydrocarbon group such as a lower alkyl group such as a methyl, ethyl or n-propyl group or a phenyl group.

A second group of particularly useful compounds of this invention is that of the formula (V):

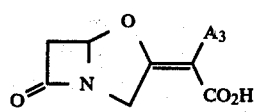

and salts and esters thereof wherein $A_3$ is a hydrogen atoms or an alkyl group of 1-6 carbon atoms or an aryl group.

Suitably $A_3$ is a hydrogen atom or a methyl, ethyl, n-propyl, phenyl, hydroxyphenyl, methoxyphenyl or a thienyl group.

More suitably $A_3$ is an ethyl, n-propyl, phenyl or p-hydroxyphenyl group.

A third group of particularly useful compounds of this invention is that of the formula (VI):

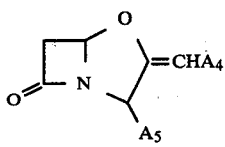

wherein $A_4$ is an aryl group and $A_5$ is a hydrogen atom or an optionally salted or esterified carboxyl group.

Certain favoured compounds of the formula (VI) are those of the formula (VIa):

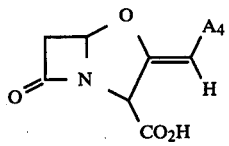

and salts and esters thereof wherein $A_4$ is an aryl group.

Suitably $A_4$ is a phenyl, substituted phenyl, thienyl or furyl or like group.

A preferred group $A_4$ is the p-hydroxyphenyl group.

More suitably $A_4$ is a phenyl, p-hydroxyphenyl, p-methoxypenyl, p-nitrophenyl, 2- or 3- thienyl, 2- or 3-furyl or like group.

Salts of the compounds of this invention which contain carboxyl groups are preferably pharmaceutically acceptable salts such as alkali metal, alkaline earth metal, ammonium and substituted ammonium salts.

Specific salts of this invention include the lithium, sodium, potassium, calcium, magnesium, ammonium, dimethylaminoethanol, trimethylamine, triethylamine, pyrrolidine, benzathine, 1-ephenamine, procain and the like salts and salts with ion exchange resins.

Particularly useful salts include the lithium, sodium and potassium salts especially when crystalline.

The salts of this invention may also be used as intermediates in producing esters in conventional manner.

Suitable esters of the compounds of this invention containing a carboxylic acid group include those wherein the ester moiety is of the sub formula (a) or (b):

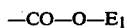

wherein $E_1$ is a hydrocarbon group of up to 8 carbon atoms optionally substituted by halogen or a group of the formula $OE_4$, $O.CO.E_4$, $SE_4$ or $SO_2E_4$ where $E_4$ is a hydrocarbon group of up to 8 carbon atoms; $E_2$ is a hydrogen atom, lower alkyl or aryl group; and $E_3$ is an aryl group.

Particularly suitable esters include the lower alkyl, benzyl, p-methoxybenzyl, allyl, phthalidyl, pivaloyloxymethyl, acetoxymethyl, methoxymethyl, α-ethoxycarbonyloxyethyl and like esters.

For those compounds of this invention which contain a carboxylic group at C-2 this carboxylic group is preferably and normally cis to the C-5 hydrogen atom.

In general the compounds of this invention are generally produced as racemic mixtures. In the compounds of the formula (II), the preferred enantiomer of the mixture has the (5R) stereochemistry. In the compounds of the formula (III) the preferred enantiomer of the mixture has the (2R, 5R) stereochemistry.

The present invention also provides a process for the preparation of the compounds of the formula (I) which process comprises the ring closing elimination of HX from a compound of the formula (VII):

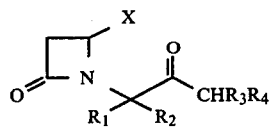

wherein X is Cl or Br and $R_1$, $R_2$, $R_3$ and $R_4$ are as defined in relation to formula (I) except that $R_4$ is not $CH_2OH$ or $CH(OH)CH_3$.

Normally and preferably X is Cl.

For those compounds of the formula (I) wherein $R_1$ is hydrogen and $R_2$ is an esterified carboxylic acid group has ring closure is believed to proceed via the formation and rearrangement of a compound of the formula (VIII):

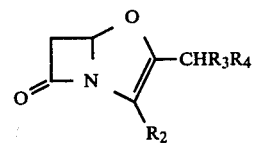

wherein $R_3$ and $R_4$ are as defined in relation to formula (I). If desired the compound of the formula (VIII) may be isolated but in general it is much more convenient to allow or cause it to re-arrange in situ by treatment with base.

The ring closure is normally effected in an inert non-hydroxylic solvent such as dimethylformamide, diethylether, dimethoxyether, tetrahydrofuran, dichloroethane, chloroform, dimethylsulphoxide or other similar solvent.

The cyclisation reaction is induced by at least a molar equivalent of a base. Suitable bases for use in the reaction include bases of low nucleophilicity such as sodium hydride, potassium hydride, potassium carbonate, 1,5-diazabicyclo[5,4,0]undec-5-ene, triethylamine, N-methylmorpholine and the like.

The reaction may take place at any non-extreme temperature such as −40° to 30° C., for example −30° to 20° C., often 5°–18° C. If the base used to bring about the reaction is potassium carbonate or the like the reaction is normally carried out at about ambient temperature. If a tertiary amine is used as base it is usual to start the reaction at a depressed temperature and then allow it to reach ambient temperature.

Following the cyclistion reaction the isomerisation of the compounds of the formula (VIII) to compounds of the formula (III) is usually accomplished by the addition of a further quantity of base, preferably potassium carbonate or a tertiary amine, generally in an amount from 0.1 to 1 molar equivalents.

If the required compound of the formula (I) is one in which one of the substituents is an optionally salted carboxyl group then it is generally more suitable to perform the cyclisation reaction on a corresponding compound of the formula (VII) wherein the substituent is a cleavable ester group and thereafter cleaving the ester, for example by hydrogenolysis of a benzyl ester.

The present invention provides a process for the preparation of the compounds of the formula (VII) which comprises the chlorination (or bromination) of a corresponding compound of the formula (IX):

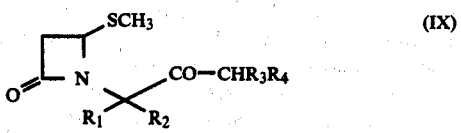 (IX)

wherein $R_1$, $R_2$, $R_3$ and $R_4$ are as defined in relation to formula (I).

The chlorination (or bromination) is normally brought about by the action of chlorine at a non-extreme temperature such as $-10°$ to $20°$ C. in an inert organic solvent such as dichloromethane, chloroform, carbon tetrachloride, or the like.

The compounds of the formula (IX) can be prepared by the alkylation of 4-methylthioazetidin-2-one with a compound of the formula (X):

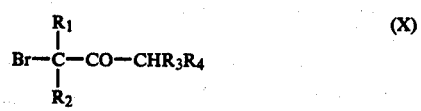 (X)

wherein $R_1$, $R_2$, $R_3$ and $R_4$ are as defined in relation to formula (I).

Most suitably 4-methylthioazetidinone is in the form of its sodium or like salt which may be generated in situ by reaction with sodium hydride or the like. The alkylation reaction is normally carried out in an inert organic solvent such as dimethylformamide or the like at a depressed temperature such as $-30°$ C. to $10°$ C., for example about $0°$ C.

The compounds of the formula (IX) wherein $R_2$ is an esterified carboxylic acid group may also be prepared by the acylation of a compound of the formula (XI):

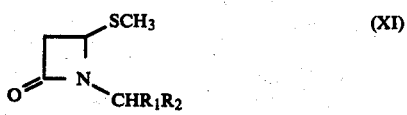 (XI)

wherein $R_1$ is as defined in relation to formula (IX) and $R_2$ is an ester group, with a compound of the formula (XII):

$$Cl-CO-CHR_3R_4 \quad (XII)$$

wherein $R_3$ and $R_4$ are as defined in relation to formula (VII).

This reaction is generally carried out in the presence of two equivalents of a base such as lithium dialkylamide or lithium di(trimethylsilyl)amide so that the compound of the formula (XI) is present as its lithium salt. The reaction is performed at a depressed temperature such as $-70°$ to $-40°$ C. in an inert medium such as tetrahydrofuran.

The compound of the formula (XI) may be prepared by the alkylation of 4-methylthioazetidin-2-one.

The compound of the formula (IX) wherein $R_2$ is not a carboxyl, or salted or esterified carboxyl group may also be prepared by the reaction of the compound of the formula formula (XIII):

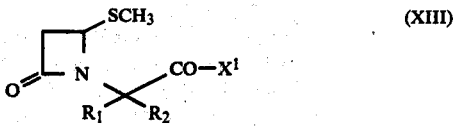 (XIII)

wherein $X^1$ is a chlorine atom or a $O.PO.(Ph)_2$ group, with a compound of the formula (XIV):

$$R_3-CH_2-R_4 \quad (XIV)$$

where $R_3$ and $R_4$ are as defined in relation to formula (IX), in the presence of a base.

The conditions for this reaction will be similar to those described for the reaction of the compounds of the formula (XI) and (XII).

If present, reactive groups such as carboxylic acid groups will normally be masked during the preceding reactions, for example as the benzyl ester from which the carboxylic acid group may be regenerated by hydrogenation, or as the methyl ester from which a salt of the carboxylic acid may be regenerated by mild basic hydrolysis.

4-Methylthioazetidin-2-one may be prepared by the reaction of $CH_3S$ with 4-acetoxyazetidinone.

The groups $R_1$, $R_2$, $R_3$ and $R_4$ in the compounds of the formula (I) may be modified chemically after the ring closure of the compound of the formula (VII) if desired. Thus, for example, an acid group may be converted to an amide; an ester or a ketonic group (e.g in $R_3$ or $R_4$) may be reduced to an alcoholic group; a doublet bond may be isomerised and the like. Suitable reagents for such transformations are described in the Examples herein.

The present invention also provides pharmaceutical compositions which comprise a compound of the invention together with a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of those salts of their invention are particularly suitable as good blood levels of the compound can occur after administration by injection or infusion. Thus, one preferred composition aspect of this invention comprises a salt of this invention in sterile form.

Unit dose compositions comprising a compound of this invention adapted for oral administration form a further composition aspect of this invention.

Under certain conditions, the effectiveness of oral compositions can be improved if such compositions contain a buffering agent or an enteric coating agent.

The compound of the invention may be present in the composition as sole therapeutic agent or it may be present together with other therapeutic agents such as a penicillin or cephalosporin.

Suitable penicillins or cephalosporins for inclusion in the compositions of this invention include benzylpenicillin, phenoxymethylpenicillin, carbenicillin, methicillin, propicillin, ampicillin, amoxycillin, epicillin, ticarcillin, cephaloridine, cephalothin, cefazolin, cephaloexin, cephacetrile, cephamandole, cepharpirin, cephradine, cephaloglycine and other well known penicillins and cephalosporins or pro-drugs therefore such as hetacillin, metampicillin, the acetoxymethyl, pivaloyloxymethyl or phthalidyl esters of benzylpenicillin, ampicillin, amoxycillin or cephaloglycine or the phenyl, tolyl or indanyl α-esters of carbenicillin or ticarcillin or the like.

When present in a pharmaceutical composition together with a penicillin or cephalosporin, the ratio of a compound of the invention to penicillin or cephalosporin, may be for example, 10:1 to 1:10 and advantageously may be from 3:1 to 1:5 for example, 1:1 to 1:3.

The total quantity of antibacterial agents present in any unit dosage form will normally be between 50 and 1500 mg and will usually be between 100 and 1000 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 500 mg of the compounds of the invention will be administered per day.

A preferred penicillin for inclusion in the compositions of this invention is amoxycillin.

The following Examples illustrate the invention:

EXAMPLE 1.1

Methyl 4-(4-methylthio-2-oxoazetidin-1-yl)-3-oxobutyrate

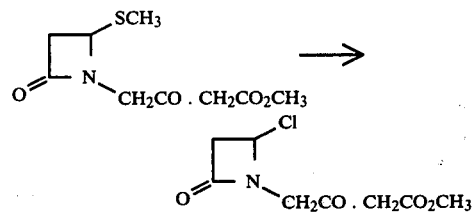

4-Methylthioazetidin-2-one (7.3 g, 62 mmole) was dissolved in a mixture of dry dimethylformamide (40 ml) and dry 1,2-dimethoxyethane (40 ml) and the solution was stirred at −20° C. (bath temperature) while sodium hydride (50% dispersion in oil, 6.3 g, 131 mmole) was added in one portion. The mixture was stirred vigorously at −20° C. with exclusion of moisture until evolution of hydrogen had ceased (ca. 5 minutes) and then while methyl 4-bromoacetoacetate (13.5 g, 69 mmole) in dry 1,2-dimethoxyethane (10 ml) was added dropwise over 2–3 minutes. After addition of the bromide, the cooling bath was replaced by an ice-water bath and stirring was continued with exclusion of moisture for 30 minutes. The mixture was poured into ice-water (200 ml) and the pH was adjusted to 4 using cold citric acid solution. The mixture was stirred with ethyl acetate (200 ml) and was filtered, the solid being washed well with more ethyl acetate. The filtrate was shaken and the layers were separated. The organic layer was washed twice with water and then dried (magnesium sulphate). The solvent was evaporated under reduced pressure to yield a dark coloured oil (11.5 g). The oil was chromatographed on silica gel (30 g) using ethyl acetate/petroleum ether to give the pure title compound as a pale yellow gum (3.6 g, 25%). (Found: M+, 231.05676. C₉H₁₃NO₄S requires 231.05652).

$\nu_{max}$ (CHCl₃): 1760 (β-lactam C=O), 1740 (shoulder, keto-ester C=O) cm⁻¹. δp.p.m. (CDCl₃): 2.03 (s, 3H, SCH₃), 2.99 (dd, J 16 Hz, J' 2.5 Hz, 1H, azetidinone C(3)H), 3.45 (dd, J 16 Hz, J' 5 Hz, 1H, azetidinone C(3)H), 3.50 (s, 2H, COCH₂CO), 3.74 (s, 3H, CO₂CH₃), 3.90 (d, J 18 Hz, 1H, NCHHCO), 4.42 (d, J 18 Hz, 1H, NCHHCO), 4.88 (dd, J 5 Hz, J' 2.5 Hz, 1H, azetidinone C(4)H). m/e (2.5%, M+), 185 (10), 184 (83), 152 (30), 142 (22), 130 (27), 116 (10), 115 (100), 110 (28), 102 (65), 101 (52), 88 (73), 87 (55), 82 (75).

EXAMPLE 1.2

Methyl 3-oxo-4-(4-chloro-2-oxoazetidin-1-yl)butyrate

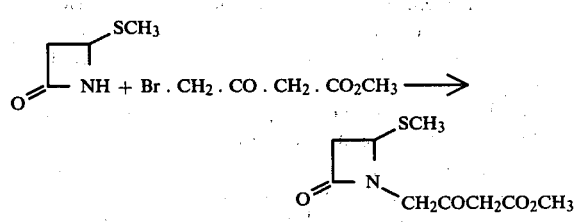

Methyl 3-oxo-4-(2-oxo-4-methylthioazetidin-1-yl)butyrate (300 mg) was dissolved in dry carbon tetrachloride (10 ml) and the solution was stirred and ice-cooled with exclusion of moisture while chlorine (90 mg) in dry carbon tetrachloride (1.5 ml) was added in one portion. After addition, the mixture was warmed to room temperature and stirred for 3 minutes. The solvent was then evaporated under reduced pressure. The residue was dissolved in fresh carbon tetrachloride (5 ml) and again the solvent was removed under reduced pressure. The title compound was thus obtained as a yellow gum (300 mg).

$\nu_{max}$ (CHCl₃): 1790 (β-lactam C=O), 1750 (keto-ester C=O) cm⁻¹. δp.p.m. (CDCl₃): 3.22 (dd, J 15 Hz, J' 1.5 Hz, 1H, azetidinone C(3)H), ca. 3.7 (overlapped m, 1H, azetidinone C(3)H), 3.55 (s, 2H, COCH₂CO), 3.74 (s, 3H, CO₂CH₃), 3.90 (d, J 18 Hz, 1H, NCHHCO), 4.49 (d, J 18 Hz, 1H, NCHHCO), 5.82 (dd, J 4 Hz, J' 1.5 Hz, 1H, azetidinone C(4)H).

EXAMPLE 1.3

(E)-3-Carbmethoxymethylene-4-oxa-1-azabicyclo[3.2.0]heptan-7-one

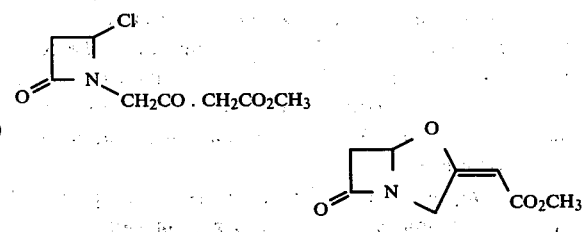

Methyl 4-(4-chloro-2-oxoazetidin-1-yl)-3-oxobutyrate (200 mg) was dissolved in dry dimethylformamide (5 ml) and anhydrous finely-powdered potassium carbonate (200 mg) was added to the solution. The mixture was stirred at room temperature with exclusion of moisture for 18 hours. The mixture was then diluted with ethyl acetate (50 ml) and was washed three times with water. The solution was dried (magnesium sulphate) and the solvent was evaporated under reduced pressure to yield a yellow gum (78 mg). The gum was chromatographed on silica gel (20 g) using ethyl acetate/petroleum ether to give the title compound as a colourless gum (42 mg, 26%) which crystallised from ether/pentane as colourless needles, m.p. 64°–65° C. (Found: M+, 183.05317. $C_8H_9NO_4$ requires 183.05315).

$\lambda_{max}$ (EtOH): 234 nm ($\epsilon$ 17000).

$\nu_{max}$ (CHCl$_3$): 1805 ($\beta$-lactam C=O), 1715 (ester C=O), 1665 (C=C), 1120 (C—O) cm$^{-1}$.

$\delta$ (CDCl$_3$): 3.05 (d, J 16 Hz, 1H, C(6)H), 3.47 (dd, J 16 Hz, J' 2 Hz, 1H, C(6)H), 3.64 (s, 3H, CO$_2$CH$_3$), 3.88 (dd, J 18 Hz, J' 2 Hz, 1H, C(2)H), 5.02 (dd, J 18 Hz, J' 2 Hz, 1H, C(2)H), 5.45 (t, J 2H$_3$, 1H, olefinic H), 5.60 (d, J 2 Hz, 1H, C(5)H). m/e: 183 (M+, 68%), 152 (48), 141 (48), 127 (100), 114 (52), 110 (29), 109 (65).

The title compound was also obtained from the experiment described in

EXAMPLE 2

(Z)-3-Carbmethoxymethylene-4-oxa-1-azabicyclo[3.2.0]heptan-7-one

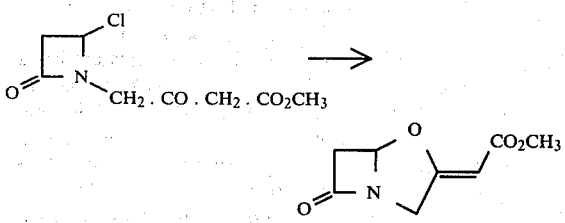

Methyl 4-(4-chloro-2-oxoazetidin-1-yl)-3-oxobutyrate (1.1 g, 5 mmole) was dissolved in a mixture of diethyl ether (20 ml) and methylene dichloride (30 ml). The solution was stirred at −30° C. with exclusion of moisture while triethylamine (510 mg, 5 mmole) in diethyl ether (5 ml) was added dropwise over 3 minutes. The mixture was then warmed to 0° C. and stirred for a further 40 minutes. The mixture was diluted with ethyl acetate (100 ml) and the solution was washed twice with 5% sodium chloride solution. The solution was dried (magnesium sulphate) and the solvent was evaporated to yield a yellow gum (350 mg). The gum was chromatographed on silica gel (30 g) using ethyl acetate/petroleum ether to give, in order of elution, (Z)-carbmethoxychloromethylene-4-oxa-1-azabicyclo[3.2.0]heptan-7-one (5 mg), (E)-carbmethoxymethylene-4-oxa-1-azabicyclo[3.2.0]heptan-7-one (73 mg) and (Z)-carbmethoxymethylene-4-oxa-1-azabicyclo[3.2.0]heptan-7-one (65 mg). The latter compound was obtained as colourless prisms, m.p. 168°–169° C., from ethyl acetate/petroleum ether (b.p. 60°–80° C.). (Found: M+, 183.05334. $C_8H_9NO_4$ requires 183.05315).

$\lambda_{max}$ (EtOH): 232 nm ($\epsilon$ 16000). $\nu_{max}$ (CHCl$_3$): 1805 ($\beta$-lactam C=O), 1715 (ester C=O), 1675 (C=C) cm$^{-1}$.

$\delta$ (CDCl$_3$): 3.18 (d, J 16.5 Hz, 1H, C(6)H), 3.52 (dd, J 16.5 Hz, J' 2 Hz, 1H, C(6)H), 3.65 (s, 3H, CO$_2$CH$_3$), 3.70 (dd, J 16 Hz, J' 1 Hz, 1H C(2)H), 4.51 (dd, J 16 Hz, J' 1 Hz, 1H, C(2)H), 4.93 (t, J 1 Hz, 1H, olefinic H), 5.75 (d, J 2 Hz, 1H, C(5)H).m/e: 183 (M+, 43%), 152 (52), 141 (47), 127 (100), 114 (39), 110 (28), 109 (43).

EXAMPLE 3

(Z)-3-(Carbmethoxychloromethylene)-4-oxa-1-azabicyclo[3.2.0]heptan-7-one

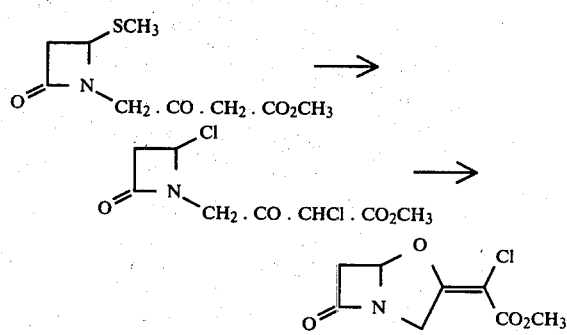

Methyl 3-oxo-4-(2-oxo-4-methylthioazetidin-1-yl)butyrate (120 mg, 0.52 mmole) was dissolved in dry carbon tetrachloride (15 ml) and the solution was stirred and ice-cooled while chlorine (75 mg, 1.05 mmole) in carbon tetrachloride (1.4 ml) was added in one portion. The cooling bath was removed and stirring was continued for 10 minutes. The solvent was then evaporated under reduced pressure to yield a pale yellow gum (135 mg).

$\nu_{max}$ (CHCl$_3$): 1785 ($\beta$-lactam C=O), 1745 (sh.) (keto-ester C=O) cm$^{-1}$.

The gum was dissolved in dry DMF (3 ml) and anhydrous, finely-powdered potassium carbonate (200 mg) was added to the solution. The mixture was stirred at room temperature with exclusion of moisture for 17 hours. The mixture was then diluted with ethyl acetate (50 ml) and washed with water (3×20 ml). The solution was dried (magnesium sulphate) and the solvent was evaporated under reduced pressure to yield a pale yellow gum (55 mg). The gum was chromatographed on silica gel (10 g) using ethyl acetate/petroleum ether to give the title compound as a colourless gum (45 mg, 40% yield). (Found: M+, 217,01426. $C_8H_8NO_4{}^{35}Cl$ requires 217.01418).

$\lambda_{max}$ (EtOH): 246 nm ($\epsilon$ 15000). $\nu_{max}$ (CHCl$_3$): 1805 ($\beta$-lactam C=O), 1715 (ester C=O), 1645 (olefinic C=C) cm$^{-1}$.

$\delta$ (CDCl$_3$): 3.05 (d, J 16 Hz, 1H, C(6)H), 3.48 (dd, J 16 Hz, J' 2 Hz, 1H, C(6)H), 3.65 (s, 3H, CO$_2$CH$_3$), 3.98 (d, J 18 Hz, 1H, C(2)H), 5.05 (d, J 18 Hz, 1H, C(2)H), 5.73 (d, J 2 Hz, 1H, C(5)H).

The title compound was also obtained from the experiment described in Example 2.

EXAMPLE 4.1

Ethyl 4-(4-methylthio-2-oxoazetidin-1-yl)-3-oxobutyrate

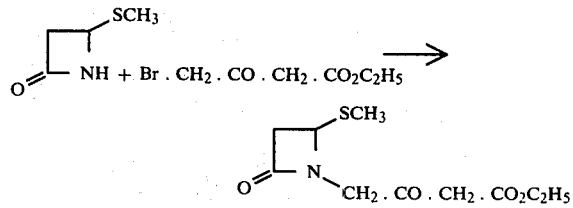

The title compound was prepared by a procedure exactly analogous to that described in Example 1.1 and was obtained as a colourless gum. $\nu_{max}$ (CHCl$_3$): 1760 ($\beta$-lactam C=O), 1740 (sh.) and 1725 (sh.) (ketoester C=O) cm$^{-1}$. $\delta$ (CDCl$_3$): 1.32 (t, J 7 Hz, 3H, CH$_3$), 2.05 (s, 3H, SCH$_3$), 2.98 (dd, J 15.5, J' 2 Hz, 1H, $\beta$-lactam CHH), 3.46 (dd, J 15.5, J' 5 Hz, 1H, $\beta$-lactam CHH), 3.50 (s, 2H, COCH$_2$CO), 3.87 (d, J 18 Hz, 1H, NCHHCO), 4.20 (q, J 7 Hz, 2H, OCH$_2$), 4.43 (d, J 18 Hz, 1H, NCHHCO), 4.88 (dd, J 5, J' 2 Hz, 1H, $\beta$-lactam CH).

EXAMPLE 4.2

(E)- and (Z)-3-Carbethoxymethylene-4-oxa-1-azabicyclo[3.2.0]heptan-7-one

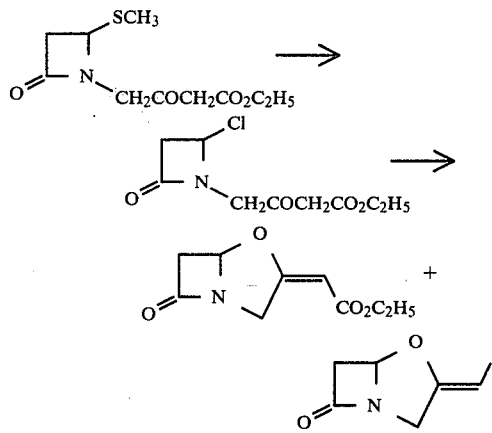

Ethyl 4-(4-methylthio-2-oxoazetidin-1-yl)-3-oxobutyrate (400 mg, 1.63 mmole) was dissolved in dry carbon tetrachloride (15 ml) and the solution was stirred and ice-cooled while chlorine (115 mg, 1.6 mmmole) in carbon tetrachloride (1.4 ml) was added in one portion. After addition of the chlorine, the cooling bath was removed and stirring was continued for 3 minutes. The solvent was removed under reduced pressure to yield ethyl 4-(4-chloro-2-oxoazetidin-1-yl)-3-oxobutyrate as a pale yellow gum (400 mg), $\nu_{max}$ (CHCl$_3$): 1785 ($\beta$-lactam C=O), 1750 and 1730 (keto-ester C=O) cm$^{-1}$.

The above product was dissolved in dry dimethylformamide (5 ml) and anhydrous finely-powdered potassium carbonate (400 mg) was added. The mixture was stirred at room temperature with exclusion of moisture for 16 hours. The mixture was diluted with ethyl acetate (50 ml) and was washed three times with water (20 ml portions). The solution was dried (magnesium sulphate) and the solvent was evaporated under reduced pressure to yield a yellow gum (140 mg). The gum was chromatographed on silica gel (20 g) using ethyl acetate/petroleum ether (b.p. 60°-80° C.) to give, in order of elution, the following compounds.

(E)-3-carbethoxymethylene-4-oxa-1-azabicyclo[3.2.0]heptan-7-one as a colourless gum (64 mg, 20% yield).

(Found: M$^+$, 197.06895. C$_9$H$_{11}$NO$_4$ requires 197.06880). $\lambda_{max}$ (EtOH): 233 nm ($\epsilon$ 18000). $\nu_{max}$ (CHCl$_3$): 1803 ($\beta$-lactam C=O), 1708 (ester C=O), 1660 (olefinic C=C) cm$^{-1}$.

$\delta$ (CDCl$_3$): 1.28 (t, J 7 Hz, 3H, CH$_3$), 3.05 (d, J 16 Hz, 1H, C(6)H), 3.48 (dd, J 16, J' 2 Hz, 1H, C(6)H), 3.84 (dd, J 18, J' 1.5 Hz, 1H, C(2)H), 4.08 (q, J 7 Hz, 2H, OCH$_2$), 5.08 (dd, J 18, J' 1.5 Hz, 1H, C(2)H), 5.56 (t, J 1.5 Hz, 1H, olefinic H), 5.66 (d, J 2 Hz, 1H, C(5)H). m/e: 197 (M$^+$, 43%), 152 (71), 141 (69), 127 (100), 125 (62), 110 (40), 109 (71), 100 (76).

(Z)-3-carbethoxymethylene-4-oxa-1-azabicyclo[3.2.0]heptan-7-one as a colourless gum (10 mg, 3% yield). (Found: M$^+$, 197.06894. C$_9$H$_{11}$NO$_4$ requires 197.06880).

$\nu_{max}$ (CHCl$_3$): 1802 ($\beta$-lactam C=O), 1710 (ester C=O), 1675 (olefinic C=C) cm$^{-1}$.

$\delta$ (CDCl$_3$): 1.26 (t, J 7 Hz, 3H, CH$_3$), 3.18 (d, J 16 Hz, 1H, C(6)H), 3.52 (dd, J 16, J' 2 Hz, 1H, C(6)H), 3.71 (d, J 16 Hz, 1H, C(2)H), 4.11 (q, J 7 Hz, 2H, OCH$_2$), 4.50 (dd, J 16 Hz, J' 1 Hz, 1H, C(2)H), 4.92 (d, J 1 Hz, 1H, olefinic H), 5.74 (d, J 2 Hz, 1H, C(5)H).

m/e: 197 (M$^+$, 31%), 152 (100), 141 (79), 127 (90), 125, (73), 110 (53), 109 (68), 100 (73).

EXAMPLE 5.1

3-Chloro-3-(carbethoxychloromethyl)-4-oxa-1-azabicyclo[3.2.0]heptan-7-one

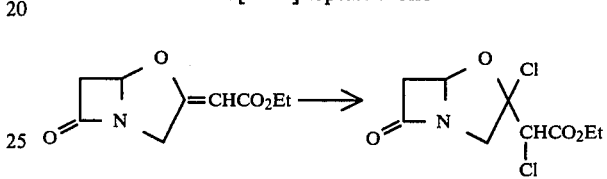

3-Carbethoxymethylene-4-oxa-1-azabicyclo[3.2.0]heptan-7-one (50 mg, 0.25 mmole) was dissolved in dry methylene dichloride (3 ml) and the solution was stirred and ice-cooled while chlorine (18 mg, 0.25 mmole) in dry carbon tetrachloride (0.9 ml) was added in one portion. The solution was stirred and ice-cooled for 10 minutes and then the cooling bath was removed and stirring was continued for a further one hour. The solvent was then evaporated under reduced pressure to yield the title compound as a yellow gum (70 g).

$\nu_{max}$ (CHCl$_3$): 1787 ($\beta$-lactam C=O), 1745 (ester C=O cm$^{-1}$. $\delta$ (CDCl$_3$): 1.31 (t, J 7 Hz, 3H, CH$_3$), 3.17 (d, J 15 Hz, 1H, C6-H), 3.67 (dd, J 15, 3 Hz, 1H, C6-H), 4.0–5.0 (complex, 5H), 5.89 (d, J 3 Hz, 1H, C5-H).

EXAMPLE 5.2

3-(Carbethoxychloromethylene)-4-oxa-1-azabicyclo[3.2.0]heptan-7-one

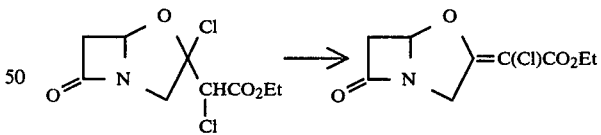

3-Chloro-3-(carbethoxychloromethyl)-4-oxa-1-azabicyclo[3.2.0.]-heptan-7-one (70 mg) was dissolved in dry methylene dichloride (5 ml) and the solution was stirred and ice-cooled while triethylamine (30 mg) was added dropwise. After addition, the mixture was stirred and ice-cooled for a further 2 hours. The mixture was then diluted with ethyl acetate (50 ml) and washed with water (2×20 ml). The solution was dried (magnesium sulphate) and the solvent was removed under reduced pressure to yield a yellow gum (30 mg). The gum was chromatographed on silica gel (5 g) using ethyl acetate/petroleum ether to give the title compound as a colourless gum.

$\lambda_{max}$. (EtOH): 247 nm ($\epsilon$ 17,000). $\nu_{max}$. (CHCl$_3$): 1805 ($\beta$-lactam C=O), 1705 (ester C=O), 1642 (olefinic C=C) cm$^{-1}$. δ (CDCl$_3$): 1.31 (t, J 7 Hz, 3H, CH$_3$), 3.15 (d, J 16 Hz, 1H, C6-H), 3.54 (dd, J 16, 2 Hz, 1H, C6-H), 3.94 (d, J 18 Hz, 1H, C2-H), 4.22 (q, J 7 Hz, 2H, CO$_2$CH$_2$), 5.03 (d, J 18 Hz, 1H, C2-H), 5.72 (d, J 2 Hz, 1H, C5-H). m/e 233 (M$^+$, 16%), 231 (M$^+$, 46), 188 (8), 186 (24), 177 (21), 175 (60), 168 (16), 163 (29), 161 (84), 136 (32), 134 (100).

EXAMPLE 6.1

Benzyl 4-(4-methylthio-2-oxoazetidin-1-yl)-3-oxobutyrate

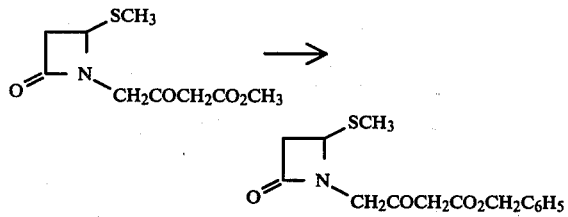

Methyl 4-(4-methylthio-2-oxoazetidin-1-yl)-3-oxobutyrate (2.0 g, 8.66 mmole) was dissolved in dry toluene (40 ml) and benzyl alcohol (2.8 g) and sodium methoxide (20 mg) were added to the solution. The mixture was stirred and refluxed, with azeotropic removal of methanol, for 20 hours. The mixture was cooled, diluted with ethyl acetate (75 ml), and washed twice with water. The solution was dried (magnesium sulphate) and the solvent was evaporated under reduced pressure to give a dark coloured oil (4.5 g). The oil was chromatographed on silica gel (35 g) using ethyl acetate/petroleum ether (b.p. 60°–80° C.) to give the title compound as a pale yellow oil (2.2 g, 83% yield). (Found: M$^+$, 307.08763. C$_{15}$H$_{17}$NO$_4$S requires 307.08782). ν$_{max}$ (CHCl$_3$): 1760 (β-lactam C=O), 1735 (sh.) (keto-ester C=O) cm$^{-1}$.

δ (CDCl$_3$): 1.95 (s, 3H, SCH$_3$), 2.90 (dd, J 15, J' 2 Hz, 1H, β-lactam CHH), 3.31 (dd, J 15, J' 5 Hz, 1H, β-lactam (CHH), 3.47 (s, 2H, COCH$_2$CO), 3.82 (d, J 18.5 Hz, 1H, NCHHCO), 4.33 (d, J 18.5 Hz, 1H, NCHHCO), 4.74 (dd, J 5, J' 2 Hz, 1H, β-lactam CH), 5.10 (s, 2H, OCH$_2$Ph), 7.27 (s, 5H, C$_6$H$_5$). m/e: 307 (M$^+$, 1%), 260 (25), 130 (11), 108 (19), 107 (15), 91 (100).

EXAMPLE 6.2

(E)- and (Z)-3-(Benzyloxycarbonylmethylene)-4-oxa-1-azabicyclo[3.2.0]-heptan-7-one and (Z)-3-(benzyloxycarbonylchloromethylene)-4-oxa-1-azabicyclo[3.2.0]heptan-7-one

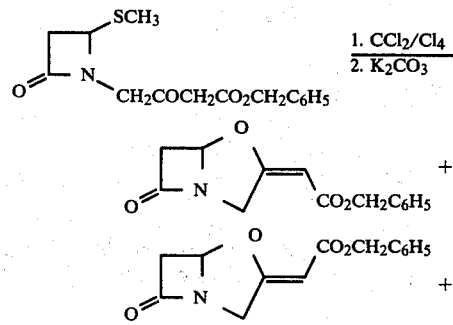

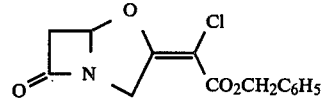

Benzyl 4-(4-methylthio-2-oxoazetidin-1-yl)-3-oxobutyrate (400 mg, 1.3 mmole) was dissolved in dry carbon tetrachloride (20 ml) and the solution was stirred and ice-cooled while chlorine (92 mg, 1.3 mmole) in carbon tetrachloride (1.9 ml) was added in one portion. After addition of the chlorine, the cooling bath was removed and stirring was continued for 3 minutes. The solvent was evaporated under reduced pressure to yield a yellow gum (395 mg). The gum was dissolved in dry dimethylformamide (5 ml) and anhydrous finely-powdered potassium carbonate (400 mg) was added. The mixture was stirred at room temperature with exclusion of moisture for 17 hours. The mixture was diluted with ethyl acetate (50 ml) and was washed three times with water. The solution was dried and the solent was evaporated under reduced pressure to yield a brown gum (290 mg). The gum was chromatographed on silica gel (20 g) using ethyl acetate/petroleum ether (b.p. 60°–80° C.) to give, in order of elution, the following compounds.

(Z)-3-(benzyloxycarbonylchloromethylene)4-oxa-1-azabicyclo[3.2.0]heptan-7-one as a colourless gum (13 mg, 3.5% yield). (Found: M$^+$, 293.04548. C$_{14}$H$_{12}$NO$_4{}^{35}$Cl requires 293.04548). λ$_{max}$ (EtOH): 247 nm (ε 13000). δ (CDCl$_3$): 3.14 (d, J 16 Hz, 1H, C(6)H), 3.52 (dd, J 16, J' 2 Hz, 1H, C(6)H), 3.91 (d, J 18 Hz, 1H, C(2)H), 5.00 (d, J 18 Hz, 1H, C(2)H), 5.19 (s, 2H, OCH$_2$Ph), 5.71 (d, J 2 Hz, 1H, C(5)H), 7.28 (s, 5H, C$_6$H$_5$). m/e: 295 (M$^+$, 26%), 293 (M$^+$, 76), 199 (5), 198 (4), 197 (15), 196 (9), 161 (8), 159 (21), 91 (100).

(E)-3-(benzyloxycarbonylmethylene)-4-oxa-1-azabicyclo[3.2.0]heptan-7-one was obtained as colourless prisms (120 mg, 36% yield), m.p. 112°–113° C. (Found: M$^+$, 259.08469. C$_{14}$H$_{13}$NO$_4$ requires 259.08445).

λ$_{max}$ (EtOH): 235 nm (ε 16200). ν$_{max}$ (CHCl$_3$): 1803 (β-lactam C=O), 1710 (ester C=O), 1660 (olefinic C=C) cm$^{-1}$.

δ (CDCl$_3$): 3.03 (d, J 16 Hz, 1H, C(6)H), 3.46 (dd, J 16, J' 2 Hz, 1H, C(6)H), 3.89 (dd, J 18, J' 1.5 Hz, 1H, C(2)H), 5.03 (dd, J 18, J' 1.5 Hz, 1H, C(2)H), 5.11 (s, 2H, OCH$_2$Ph), 5.48 (t, J 1.5 Hz, 1H, olefinic H), 5.56 (d, J 2 Hz, 1H, C(5)H), 7.28 (s, 5H, C$_6$H$_5$). m/e: 259 (M$^+$, 18%), 190 (15), 153 (100), 91 (80).

(Z)-3-(benzyloxycarbonylmethylene)-4-oxa-1-azabicyclo[3.2.0]heptan-7-one was obtained as a colourless gum (10 mg, 3% yield).

λ$_{max}$ (EtOH): 236 nm (ε 17000). ν$_{max}$ (CHCl$_3$): 1805 (β-lactam C=O), 1710 (ester C=O), 1675 (olefinic C=C) cm$^{-1}$.

δ (CDCl$_3$): 3.16 (d, J 16 Hz, 1H, C(6)H), 3.52 (dd, J 16, J' 2 Hz, 1H, C(6)H), 3.66 (d, J 16 Hz, 1H, C(2)H), 4.49 (d, J 16 Hz, 1H, C(2)H), 4.97 (s, 1H, olefinic H), 5.10 (s, 2H, OCH$_2$Ph), 5.74 (d, J 2 Hz, 1H, C(5)H), 7.27 (s, 5H, C$_6$H$_5$).

EXAMPLE 7

Sodium
(E)-7-oxo-4-oxa-1-azabicyclo[3.2.0]heptan-3-methylenecarboxylate

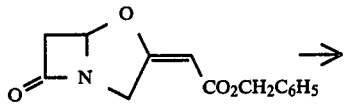

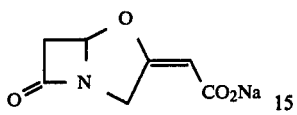

(E)-3-(Benzyloxycarbonylmethylene)-4-oxa-1-azabicyclo[3.2.0]-heptan-7-one (100 mg, 0.386 mmole) and 10% palladium-on-charcoal (120 mg) in tetrahydrofuran (15 ml) was shaken under one atmosphere of hydrogen at room temperature for 1 hour. The catalyst was removed by filtration and was washed well with fresh tetrahydrofuran. A solution of sodium bicarbonate (33 mg) in water (5 ml) was added with stirring to the filtrate. The tetrahydrofuran was evaporated under reduced pressure to give an aqueous residue which was freeze-dried to yield the title compound as a colourless amorphous powder (75 mg).

$\lambda_{max}$ (water): 227.5 nm ($\epsilon$ 17100). $\nu_{max}$ (KBr): 1785 ($\beta$-lactam C=O), 1660 (olefinic C=C), 1540 and 1410 (carboxylate) cm$^{-1}$.

$\delta$ (D$_2$O): 2.96 (d, J 17 Hz, 1H, C(6)H), 3.42 (dd, J 17, J' 2 Hz, 1H, C(6)H), 3.78 (dd, J 18, J' 2 Hz, 1H, C(2)H), 4.79 (dd, J 18, J' 2 Hz, 1H, C(2)H), 5.28 (t, J 2 Hz, 1H, olefinic H), 5.52 (d, J 2 Hz, 1H, C(5)H). Field-desorption mass spectrum, m/e: 214 (100%, C$_7$H$_6$NO$_4$Na+Na).

EXAMPLE 8

(E)-3-[(Benzyloxycarbonylmethoxy)carbonylmethylene]-4-oxa-1-azabicyclo[3.2.0]heptan-7-one

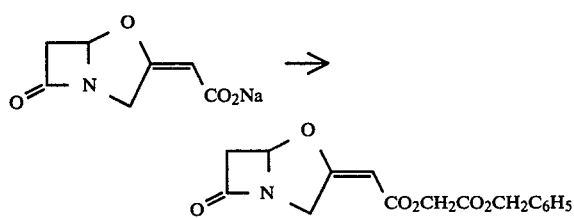

Sodium (E)-7-oxo-4-oxa-1-azabicyclo[3.2.0]heptan-3-methylenecarboxylate (45 mg, 0.235 mmole) was dissolved in dry dimethylformamide (2 ml) and benzyl bromoacetate (90 mg, 0.39 mmole) was added to the solution, which was then stirred at room temperature with exclusion of moisture for 17 hours. The solution was diluted with ethyl acetate (50 ml) and was washed three times with water (20 ml portions). The solution was dried (magnesium sulphate) and the solvent was evaporated under reduced pressure to yield a yale yellow gum (130 mg). The gum was chromatographed on silica gel (10 g) using ethyl acetate/petroleum ether (b.p. 60°–80° C.) to give the title compound as a colourless gum (50 mg, 67% yield). (Found: M+, 317.08982. C$_{16}$H$_{15}$NO$_6$ requires 317.08993).

$\lambda_{max}$ (EtOH): 236 nm ($\epsilon$ 18000). $\nu_{max}$ (CHCl$_3$): 1805 ($\beta$-lactam C=O), 1755 (ester C=O), 1710 (ester C=O), 1660 (olefinic C=C), 1120 (C—O) cm$^{-1}$.

$\delta$ (CDCl$_3$): 2.97 (d, J 16 Hz, 1H, C(6)H), 3.42 (dd, J 16, J' 2 Hz, 1H, C(6)H), 3.80 (d, J 18 Hz, 1H, C(2)H), 4.52 (s, 2H, OCH$_2$CO), 4.91 (dd, J 18, J' 2 Hz, 1H, C(2)H), 5.15 (s, 2H, OCH$_2$Ph), 5.63 (m, 2H, olefinic H and C(5)H), 7.30 (s, 5H, C$_6$H$_5$). m/e: 317 (M+, 37%), 289 (67), 275 (23), 231 (41), 213 (31), 185 (93), 91 (100).

EXAMPLE 9

(E)-3-[Carboxymethoxy)carbonylmethylene]-4-oxa-1-azabicyclo[3.2.0.]-heptan-7-one

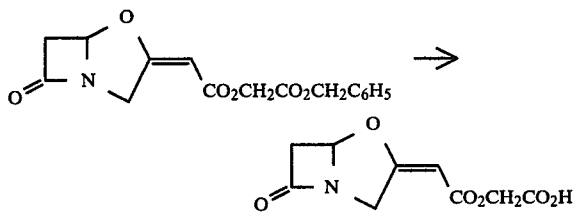

(E)-3-[Benzyloxycarbonylmethoxy)carbonylmethylene]-4-oxa-1-azabicyclo[3.2.0]heptan-7-one (65 mg, 0.2 mmole) and 10% palladium-on-charcoal (50 mg) in 5% aqueous tetrahydrofuran (20 ml) was shaken under one atmosphere of hydrogen at room temperature for one hour. The catalyst was removed by filtration and was washed with tetrahydrofuran. A solution of sodium bicarbonate (20 mg) in water (5 ml) was added to the filtrate with stirring. The tetrahydrofuran was evaporated under reduced pressure to give an aqueous residue which was freeze-dried to yield the sodium salt of the title compound as a colourless amorphous powder (53 mg). $\lambda_{max}$ (water): 239 nm ($\epsilon$ 14000). $\nu_{max}$ (KBr): 1790 ($\beta$-lactam C=O), 1700 (ester C=O), 1655 (sh.) (olefinic C=C), 1615 and 1400 (carboxylate) cm$^{-1}$. $\delta$ (D$_2$O): 3.11 (d, J 17 Hz, 1H, C(6)H), 3.53 (dd, J 17, J' 2 Hz, 1H, C(6)H), 3.96 (dd, J 18, J' 1.5 Hz, 1H, C(2)H), 4.38 (s, 2H, OCH$_2$CO), 4.95 (dd, J 18, J' 1.5 Hz, 1H, C(2)H), 5.53 (t, J 1.5 Hz, 1H, olefinic H), 5.74 (d, J 2 Hz, 1H, C(5)H).

EXAMPLE 10

(E)-3-(N-Phenylcarbamoylmethylene)-4-oxa-1-azabicyclo[3.2.0]heptan-7-one

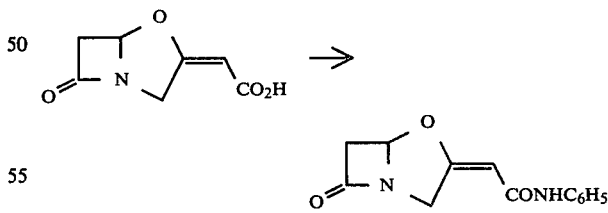

(E)-3-(Benzyloxycarbonylmethylene)-4-oxa-1-azabicyclo[3.2.0]-heptan-7-one (50 mg, 0.19 mmole) and 10% palladium-on-charcoal (50 mg) in dry tetrahydrofuran (5 ml) was shaken under one atmosphere of hydrogen at room temperature with exclusion of moisture for one hour. The catalyst was removed by filtration and was washed with dry tetrahydrofuran. The filtrate, which consisted of a solution of (E)-3-(carboxymethylene)-4-oxa-1-azabicyclo[3.2.0]-heptan-7-one (0.19 mmole) in tetrahydrofuran, was concentrated to ca. 2 ml by evaporation of solvent under reduced pressure.

To this solution dicyclohexylcarbodiimide (78 mg) and aniline (25 mg) were added and the mixture was stirred at room temperature with exclusion of moisture for 16 hours. The mixture was diluted with ethyl acetate (50 ml) and was washed with 10% citric acid solution, saturated sodium bicarbonate solution, and saturated brine. The solution was dried (magnesium sulphate) and the solvent was evaporated under reduced pressure to yield a yellow gum (145 mg). The gum was chromatographed on silica gel (10 g) using ethyl acetate/petroleum ether (b.p. 60°–80° C.) to give the title compound as a colourless gum (15 mg, 33% yield).

$\nu_{max}$ (CHCl$_3$): 3410 and 3300 (amide NH), 1800 ($\beta$-lactam C=O), 1690 (amide C=O), 1640 (olefinic C=C), 1520 (amide II band), 1110 (C—O) cm$^{-1}$. $\delta$(CDCl$_3$): 3.02 (d, J 16 Hz, 1H, C(6)H), 3.46 (dd, J 16, J' 2 Hz, 1H, C(6)H), 3.98 (dd, J 18, J' 1 Hz, 1H, C(2)H), 5.14 (dd, J 18, J' 1 Hz, C(2)H), 5.50 (br.s, 2H, olefinic H and C(5)H), 6.9–7.5 (m, 6H, NH and C$_6$H$_5$).

EXAMPLE 11.1

Methyl 4-(4-methylthio-2-oxoazetidin-1-yl)-2-methyl-3-oxobutyrate

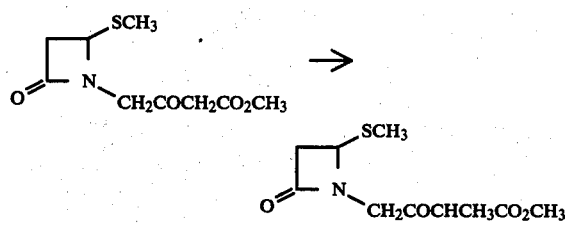

Methyl 4-(4-methylthio-2-oxoazetidin-1-yl)-3-oxobutyrate (575 mg, 2.5 mmole) and methyl iodide (355 mg, 2.5 mmole) were dissolved in dry dimethylformamide (10 ml) and anhydrous finely-powdered potassium carbonate (500 mg) was added to the solution, which was then stirred for 3 hours at room temperature with exclusion of moisture. The mixture was diluted with ethyl acetate (70 ml) and was washed three times with water (30 ml portions). The solution was dried (magnesium sulphate) and the solvent was evaporated under reduced pressure to give a yellow gum (560 mg). The gum was chromatographed on silica gel (20 g) using ethyl acetate/petroleum ether (b.p. 60°–80° C.) to give the title compound as a colourless gum (300 mg, 49% yield). This product consisted of a 1:1 mixture of diastereomers as judged by n.m.r. spectroscopy. (Found: M$^+$, 245.07218. C$_{10}$H$_{15}$NO$_4$S requires 245.07217).

$\nu_{max}$ (CHCl$_3$): 1760 ($\beta$-lactam C=O), 1750 (sh.) and 1730 (sh.) (ketoester C=O) cm$^{-1}$. $\delta$(CDCl$_3$): 1.33 (d, J 7 Hz, CH$_3$), 2.00 (s, 3H, SCH$_3$), 2.96 (dd, J 16, J' 2 Hz, 1H, $\beta$-lactam CHH), 3.47 (dd, J 16, J' 5 Hz, 1H, $\beta$-lactam CHH), ca. 3.7 (overlapped m, 1H, CHMe), 3.69 (s, 3H, OCH$_3$), 3.87 and 3.93 (both d, J 18 Hz, 1H, NCHHCO), 4.45 and 4.49 (both d, J 18 Hz, 1H, NCHHCO), 4.80 (m, 1H, C(5)H). m/e: 245 (M$^+$, 4%), 198 (100), 166 (24), 130 (40), 129 (80), 102 (44), 101 (32), 96 (40), 88 (52).

EXAMPLE 11.2

(E)-3-(1-Methoxycarbonylethylidene)-4-oxa-1-azabicyclo[3.2.0]heptan-7-one

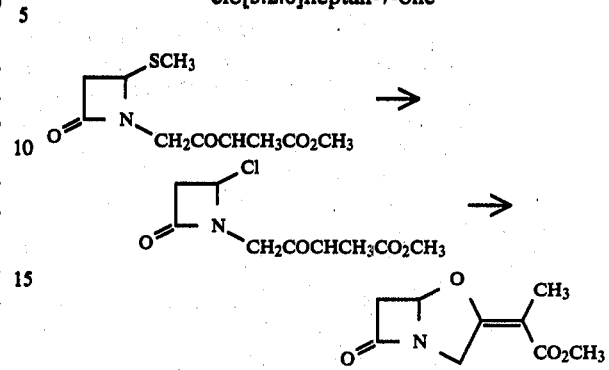

Methyl 4-(4-methylthio-2-oxoazetidin-1-yl)-2-methyl-3-oxobutyrate (280 mg, 1.14 mmole) was dissolved in dry carbon tetrachloride (15 ml) and to the stirred ice-cooled solution chlorine (80 mg, 1.13 mmole) in carbon tetrachloride (3.2 ml) was added in one portion. After addition of the chlorine, the cooling bath was removed and stirring was continued for 3 minutes. The solvent was evaporated under reduced pressure to yield methyl 4-(4-chloro-2-oxoazetidin-1-yl)-2-methyl-3-oxobutyrate as a pale yellow gum (275 mg). $\nu_{max}$ (CHCl$_3$): 1780 ($\beta$-lactam C=O), 1755 (ester C=O), 1725 (ketone C=O) cm$^{-1}$.

The above product was dissolved in dry dimethylformamide (5 ml) and anhydrous finely-powdered potassium carbonate (300 mg) was added. The mixture was stirred at room temperature with exclusion of moisture for 18 hours. The mixture was diluted with ethyl acetate (50 ml) and was washed three times with water (20 ml portions). The solution was dried (magnesium sulphate) and the solvent was evaporated under reduced pressure to yield a yellow gum (180 mg). The gum was chromatographed on silica gel (10 g) using ethyl acetate/petroleum ether (b.p. 60°–80° C.) to give the title compound as colourless needles (135 mg, 61% yield), m.p. 90°–91° C. (Found: M$^+$, 197.06895. C$_9$H$_{11}$NO$_4$ requires 197.06880).

$\lambda_{max}$ (EtOH): 238 nm ($\epsilon$ 15700). $\nu_{max}$ (CHCl$_3$): 1803 ($\beta$-lactam C=O), 1710 (ester C=O), 1655 (olefinic C=C), 1120 (C—O) cm$^{-1}$. $\delta$(CDCl$_3$): 1.82 (t, J 1 Hz, 3H, CH$_3$), 3.02 (d, J 16 Hz, 1H, C(6)H), 3.47 (dd, J 16, J' 2 Hz, 1H, C(6)H), 3.67 (s, 3H, OCH$_3$), 3.81 (dd, J 18, J' 1 Hz, 1H, C(2)H), 4.92 (dd, J 18, J' 1 Hz, 1H, C(2)H), 5.54 (d, J 2 Hz, 1H, C(5)H).

m/e: 197 (M$^+$, 76%), 182 (1), 166 (83), 155 (43), 141 (100), 128 (69), 122 (52), 96 (50), 83 (62).

EXAMPLE 12.1

Benzyl 4-(4-methylthio-2-oxoazetidin-1-yl)-2-methyl-3-oxobutyrate

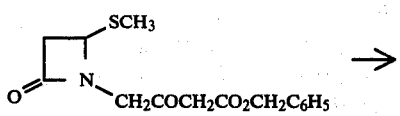

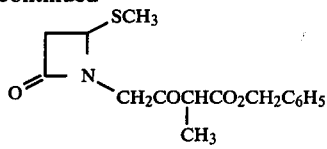

Benzyl 4-(4-methylthio-2-oxoazetidin-1-yl)-3-oxobutyrate (307 mg, 1 mmole) was converted into the title compound by a procedure exactly analogous to that described in Example 11.1. The title compound was obtained as a colourless gum (70 mg, 22% yield). $\nu_{max}$ (CHCl$_3$): 1760 ($\beta$-lactam C=O), 1740 (sh.) and 1720 (sh.) (keto-ester C=O) cm$^{-1}$. $\delta$(CDCl$_3$): 1.35 (d, J 7 Hz, 3H, CH$_3$), 1.94 (s, 3H, SCH$_3$), 2.90 (dd, J 16, J' 2 Hz, 1H, $\beta$-lactam CHH), 3.1–3.6 (complex, 2H, $\beta$-lactam CHH and COCHCO), 3.71 and 3.79 (both d, J 17 Hz, 1H, NCHHCO), 4.28 and 4.31 (both d, J 17 Hz, 1H, NCHHCO), 4.60 (m, 1H, $\beta$-lactam CH), 5.11 (s, 2H, OCH$_2$Ph), 7.30 (s, 5H, C$_6$H$_5$).

EXAMPLE 12.2

(E)-3-(1-Benzyloxycarbonylethylidene)-4-oxa-1-azabicyclo[3.2.0]heptan-7-one

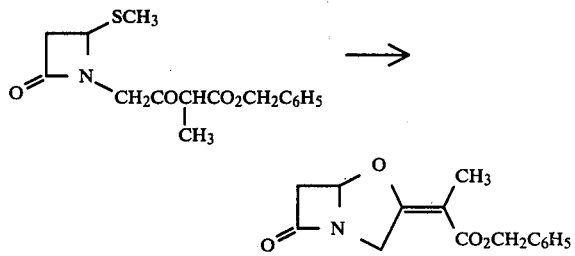

Benzyl 4-(4-methylthio-2-oxoazetidin-1-yl)-2-methyl-3-oxobutyrate (108 mg, 0.327 mmole) was converted into the title compound using the process described in Example 11.2. The title compound was obtained as a colourless gum (49 mg, 55% yield). (Found: M$^+$, 273.09993. C$_{15}$H$_{15}$NO$_4$ requires 273.100098). $\nu_{max}$ (CHCl$_3$): 1805 ($\beta$-lactam C=O), 1710 (ester C=O), 1660 (olefinic C=C), 1120 (C—O) cm$^{-1}$.

$\delta$(CHCl$_3$): 1.87 (s, 3H, SCH$_3$), 3.00 (d, J 16 Hz, 1H, C(2)H), 4.91 (dd, J 18, J' 1 Hz, 1H, C(2)H), 5.10 (s, 2H, OCH$_2$Ph), 5.52 (d, J 2 Hz, 1H, C(5)H), 7.28 (s, 5H, C$_6$H$_5$). m/e: 273 (M$^+$, 4%), 245 (0.3), 167 (2.4), 166 (2.6), 139 (14), 91 (100).

EXAMPLE 13

Sodium (E)-7-oxo-4-oxa-1-azabicyclo[3.2.0]heptane-3-(ethylidene-1-carboxylate)

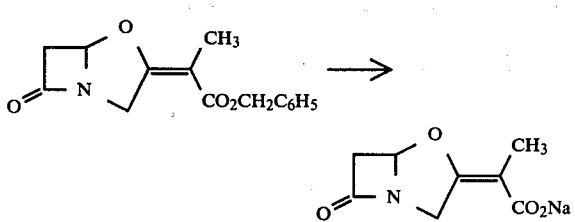

(E)-3-(1-Benzyloxycarbonylethylidene)-4-oxa-1-azabicyclo[3.2.0]heptan-7-one (35 mg, 0.128 mmole) was converted into the title compound using the process described in Example 7. The title compound was obtained as a colourless amorphous powder (25 mg). $\lambda_{max}$(water): 233 nm ($\epsilon$ 16000). $\nu_{max}$(KBr): 1787 ($\beta$-lactam C=O), 1670 (olefinic C=C), 1570 and 1400 (carboxylate) cm$^{-1}$.

$\delta$(D$_2$O): 1.67 (t, J 1 Hz, 3H, CH$_3$), 2.97 (d, J 17 Hz, 1H, C(6)H), 3.45 (dd, J 17, J' 2 Hz, 1H, C(6)H), 3.78 (br. d, J 18 Hz, 1H, C(2)H), ca. 4.8 (dd, part overlapped by HOD, C(2)H), 5.56 (d, J 2 Hz, 1H, C(5)H).

EXAMPLE 14.1

Benzyl 4-(4-methylthio-2-oxazetidin-1-yl)-2-ethyl-3-oxobutyrate

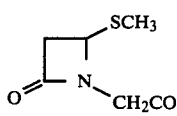 

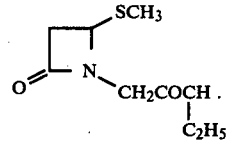

Benzyl 4-(4-methylthio-2-oxoazetidin-1-yl)-3-oxobutyrate (307 mg, 1 mmole) was converted into the title compound using the process described in Example 11.1. The title compound was obtained as a colourless gum (88 mg, 26% yield). (Found: M$^+$, 335.11894. C$_{17}$H$_{21}$NO$_4$S requires 335.11912). $\nu_{max}$ (CHCl$_3$): 1760 ($\beta$-lactam C=O), 1740 (sh.) and 1720 (sh.) (keto-ester C=O) cm$^{-1}$.

$\delta$(CDCl$_3$): 0.95 (t, J 7 Hz, 3H, CH$_3$), 1.9 (q, J 7 Hz, 2H, CH$_2$), 1.93 and 1.95 (both s, 3H, SCH$_3$), 2.88 (dd, J 16, J' 2 Hz, 1H, $\beta$-lactam CHH), 3.2–4.8 (complex, 5H, $\beta$-lactam CHH, $\beta$-lactam CH, NCH$_2$CO, COCHCO), 5.12 (s, 2H, OCH$_2$Ph), 7.28 (s, 5H, C$_6$H$_5$). m/e 335 (M$^+$, 3%), 288 (32), 261 (3), 196 (2), 182 (2), 180 (2), 130 (17), 91 (100).

EXAMPLE 14.2

(E)-3-(1-Benzyloxycarbonyl-1,1-propylidene)-4-oxa-1-azabicyclo[3.2.0]heptan-7-one

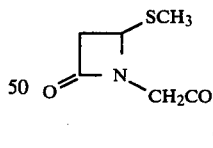 

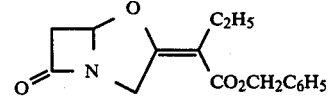

Benzyl 4-(4-methylthio-2-oxazetidin-1-yl)-2-ethyl-3-oxobutyrate (81 mg, 0.246 mmole) was converted into the title compound using the process described in Example 11.2. The title compound was obtained as a colourless gum (28 mg, 39%). (Found: M$^+$, 287.11534, C$_{16}$H$_{17}$NO$_4$ requires 287.11575). $\nu_{max}$ (CHCl$_3$): 1802 ($\beta$-lactam C=O), 1705 (ester C=O), 1650 (olefinic C=C), 1115 (C—O) cm$^{-1}$.

$\delta$(CDCl$_3$): 0.98 (t, J 7 Hz, 3H, CH$_3$), 2.33 (q, J 7 Hz, 2H, CH$_2$Me), 2.99 (d, J 16 Hz, 1H, C(6)H), 3.42 (dd, J 16, J' 2 Hz, 1H, C(6)H), 3.80 (d, J 18 Hz, 1H, C(2)H), 4.89 (d, J 18 Hz, 1H, C(2)H), 5.09 (s, 2H, OCH₂Ph), 5.52 (d, J 2 Hz, 1H, C(5)H), 7.27 (s, 5H, C₆H₅). m/e: 287 (M⁺, 5%), 272 (0.3), 259 (0.4), 223 (1), 180 (3), 153 (11), 149 (7), 91 (100).

EXAMPLE 15

Sodium (E)-7-oxo-4-oxa-1-azabicyclo[3.2.0]heptane-3-(1,1-propylidene-1-carboxylate)

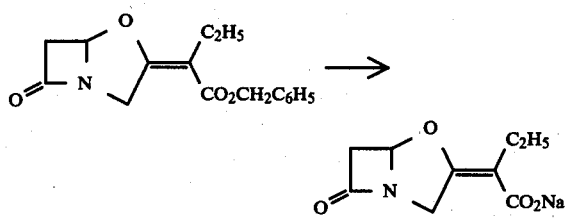

(E)-3-(1-Benzyloxycarbonyl-1,1-propylidene)-4-oxa-1-azabicyclo[3.2.0]heptan-7-one (17 mg.) was converted into the title compound using the process described in Example 7. The title compound was obtained as a colourless amorphous powder (12 mg.). $\lambda_{max}$ (water): 233 nm ($\epsilon$ 16,800). $\nu_{max}$ (KBr): 1788 ($\beta$-lactam C=O), 1665 (olefinic C=C), 1540 and 1390 (carboxylate) cm⁻¹.

EXAMPLE 16.1

Benzyl 4-(4-methylthio-2-oxoazetidin-1-yl)-2-n-propyl-3-oxobutyrate

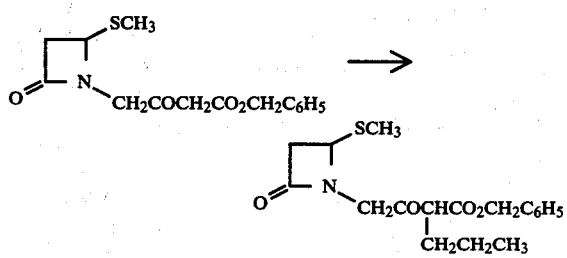

Benzyl 4-(4-methylthio-2-oxoazetidin-1-yl)-3-oxobutyrate (307 mg., 1 mmole) was converted into the title compound using the process described in Example 11.1. The title compound was obtained as a colourless gum (137 mg., 39% yield). (Found: M⁺, 349.13429. C₁₈H₂₃NO₄S requires 349.13477). $\nu_{max}$ (CHCl₃): 1760 ($\beta$-lactam C=O), 1745 (sh.) and 1720 (sh.) (keto-ester C=O) cm⁻¹. $\delta$(CDCl₃): 1.7–2.0 (complex, 7H, n-Pr), 1.91 and 1.93 (both s, 3H, SCH₃), 2.88 (dd, J 16, J' 2 Hz, 1H, $\beta$-lactam CHH), 3.0–4.8 (complex, 5H, $\beta$-lactam CH, NCH₂CO, COCHCO), 5.10 (s, 2H, OCH₂Ph), 7.29 (s, 5H, C₆H₅). m/e: 349 (M⁺, 2%), 302 (28), 275 (2.5), 258(1), 196(2), 194(2), 130(29), 91(100).

EXAMPLE 16.2

(E)-3-(1-Benzyloxycarbonyl-1,1-n-butylidene)-4-oxa-1-azabicyclo[3.2.0]heptan-7-one

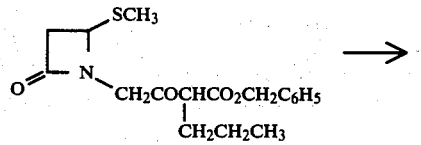

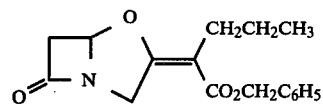

Benzyl 4-(4-methylthio-2-oxoazetidin-1-yl)-2-n-propyl-3-oxobutyrate (133 mg., 0.382 mmole) was converted into the title compound using the process described in Example 11.2. The title compound was obtained as a colourless gum (50 mg., 44% yield). (Found: M⁺, 301.131600. C₁₇H₁₉NO₄ requires 301.131397). $\nu_{max}$ (CHCl₃): 1803 ($\beta$-lactam C=O), 1705 (ester C=O), 1650 (olefinic C=C) cm⁻¹. $\delta$(CDCl₃): 0.88 (t, J 7 Hz, 3H, CH₃), 1.25–1.55 (m, 2H, CH₂Me), 2.32 (t, J 7.5 Hz, 2H, CH₂Et), 3.00 (d, J 16 Hz, 1H, C(6)H), 3.44 (dd, J 16, J' 2 Hz, 1H, C(6)H), 3.84 (d, J 18 Hz, 1H, C(2)H), 4.91 (d, J 18 Hz, 1H, C(2)H), 5.10 (s, 2H, OCH₂Ph), 5.53 (d, J 2 Hz, 1H, C(5)H), 7.27 (s, 5H, C₆H₅). m/e: 301 (M⁺, 4%), 272 (1), 230 (1), 194 (3), 167 (7), 125 (3), 91 (100).

EXAMPLE 17

Sodium (E)-7-oxo-4-oxa-1-azabicyclo[3.2.0]heptane-3-(1,1-n-butylidene-1-carboxylate)

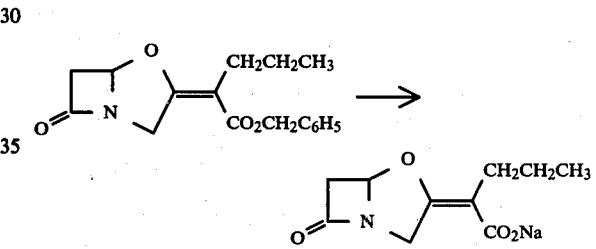

(E)-3-(1-Benzyloxycarbonyl-1,1-butylidene)-4-oxa-1-azabicyclo[3.2.0]heptan-7-one (38 mg., 0.127 mmole) was converted into the title compound using the process described in Example 7. The title compound was obtained as a colourless amorphous powder (29 mg.). $\lambda_{max}$ (water): 234 nm ($\epsilon$ 16,300). $\nu_{max}$ (KBr): 1785 ($\beta$-lactam C=O), 1665 (olefinic C=C), 1540 and 1390 (carboxylate), 1120 (C—O) cm⁻¹. $\delta$(D₂O): 0.90 (t, J 7 Hz, 3H, CH₃), 1.44 (sex., J 7 Hz, 2H, CH₂Me), 2.30 (t, J 7 Hz, 2H, CH₂Et), 3.10 (d, J 16.5 Hz, 1H, C(6)H). 3.60 (dd, J 16.5, J' 2 Hz, 1H, C(6)H), 3.90 (d, J 18 Hz, 2H, C(2)H), ca 4.8 (overlapped by HOD, C(2)H), 5.65 (d, J 2 Hz, 1H, C(5)H).

EXAMPLE 18

(E)-3-(1-Methoxycarbonyl-2-phenylthio-1,1-ethylidene)-4-oxa-1-azabicyclo[3.2.0]heptan-7-one

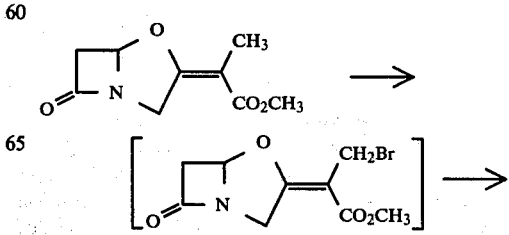

-continued

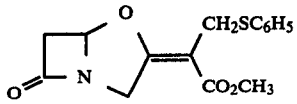

(E)-3-(1-Methoxycarbonyl-1,1-ethylidene)-4-oxa-1-azabicyclo[3.2.0]heptan-7-one (100 mg., 0.5 mmole) and 1,3-dibromo-5,5-dimethylhydantoin (75 mg., 0.26 mmole) were dissolved in dry carbon tetrachloride (6 ml.) and α,α'-azoisobutyronitrile (4 mg.) was added to the solution. The solution was refluxed and irradiated with white light (tungsten lamp) with exclusion of moisture. After about 30 minutes a colourless precipitate started to develop in the solution. One minute after this precipitate started, the mixture was cooled to room temperature. The mixture was concentrated to ca 0.5 ml. by evaporation of solvent under reduced pressure and was then diluted with 1,2-dimethoxyethane (3 ml.). The resulting solution was added to a solution of sodium thiophenolate (from 100 mg. thiophenol and 30 mg. 50% sodium hydride) in dimethylformamide (6 ml.) at 0°. The mixture was stirred at 0° with exclusion of moisture for 30 minutes. The mixture was diluted with ethyl acetate (50 ml.) and the solution was washed with water three times (20 ml. portions), dried (magnesium sulphate), and the solvent was evaporated under reduced pressure to give a yellow gum (270 mg.). The gum was chromatographed on silica gel (20 g.) using ethyl acetate/petroleum ether (b.p. 60°-80°) to give the title compound as a colourless gum (47 mg., 30% yield). (Found: M+, 305.07183. $C_{15}H_{15}NO_4S$ requires 305.07217). $\lambda_{max}$ (EtOH): 223 (ε 12,200) and 244 nm (ε 12,700). $\nu_{max}$ (CHCl$_3$): 1802 (β-lactam C=O), 1705 (ester C=O), 1645 (olefinic C=C), 1110 (C—O) cm$^{-1}$. δ(CDCl$_3$): 2.73 (d, J 16Hz, 1H, C(6)H), 3.33 (dd, J 16, J' 2Hz, 1H, C(6)H), 3.67 (s, 3H, OCH$_3$), 3.78 (s, 2H, SCH$_2$), 3.80 (d, J 18Hz, 1H, C(2)H), 4.93 (d, J 18Hz, 1H, C(2)H), 5.32 (d, J 2Hz, 1H, C(5)H), 7.15-7.45 (m, 5H, C$_6$H$_5$). m/e: 305 (M+, 13%), 196 (100), 164 (17), 154 (30), 127 (80), 110 (20), 109 (17).

EXAMPLE 19.1

Benzyl 4-(4-methylthio-2-oxoazetidin-1-yl)-2-phenyl-3-oxobutyrate

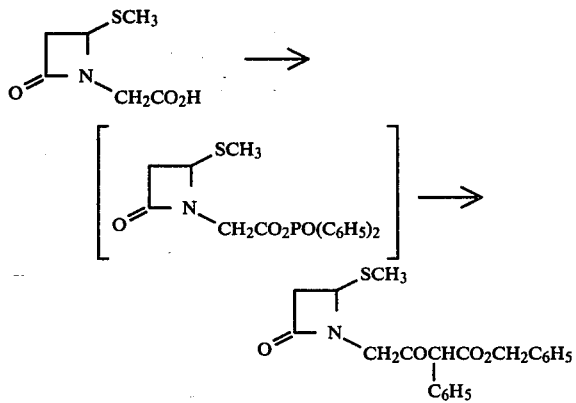

(4-Methylthio-2-oxoazetidin-1-yl)-acetic acid (175 mg., 1 mmole) was dissolved in a mixture of dry 1,2-dimethoxyethane (2 ml.) and dry ether (5 ml.). The solution was stirred and ice-cooled while 2,6-lutidine (110 mg., 1 mmole) was added followed by a solution of diphenylphosphinic chloride (240 mg., 1 mmole) in dry ether (2 ml.). The mixture was stirred and ice-cooled for 20 minutes. The precipitate was removed by filtration and was washed with dry ether. The solvent was evaporated from the combined filtrate and washings to give a colourless gum (390 mg.). The gum was dissolved in dry 1,2-dimethoxyethane (2 ml.) and the solution was added dropwise to a stirred solution of lithio benzyl acetate (1 mmole) and lithium bis(trimethylsilyl) amide (1 mmole) in dry 1,2-dimethoxyethane (10 ml.) at −70° under dry nitrogen. The mixture was stirred at −70° under dry nitrogen for 1.5 hours and was then poured into icewater (70 ml.). The aqueous mixture was overlayed with ethyl acetate (50 ml.) and the aqueous layer was brought to pH3 using citric acid solution. The mixture was shaken and the layers were separated. The aqueous layer was extracted once more with ethyl acetate (30 ml.) and the combined organic solutions were washed twice with water (30 ml. portions). The solution was dried (magnesium sulphate) and the solvent was evaporated under reduced pressure to yield a colourless gum (470 mg.). The gum was chromatographed on silica gel (30 g.) using ethyl acetate/petroleum ether (b.p. 60°-80°) to give the title compound as a colourless gum (70 mg, 18% yield). (Found: M+, 383.11906. $C_{12}H_{21}NO_4S$ requires 383.11912). $\nu_{max}$ (CHCl$_3$): 1760 (β-lactam C=O), 1735 (sh.) and 1720 (sh.) (keto-ester C=O) cm$^{-1}$. δ(CDCl$_3$): 1.90 (s, 3H, SCH$_3$), 2.81 (dd, J 16, J' 2Hz, 1H, β-lactam CHH), 3.28 (dd, J 16, J' 5Hz, 1H, β-lactam CHH), 3.70 and 3.74 (both d, J 17Hz, 1H, NCHH), 4.26 and 4.28 (both d, J 17Hz, 1H, NCHHCO), 4.60 (dd, J 5, J' 2Hz, 1H, β-lactam CH), 4.71 (s, 1H, COCHCO), 5.14 (s, 2H, OCH$_2$Ph), 7.28 (s, 5H, C$_6$H$_5$), m/e: 383 (M+, 0.5%), 336 (6), 309 (0.5), 275 (1), 267 (0.5), 236 (0.5), 228 (0.9), 226 (0.8), 201 (1.5), 130 (5), 108 (100), 107 (85), 91 (65), 79 (75), 77 (80).

EXAMPLE 19.2

(E)-3-(1-Benzyloxycarbonylbenzylidene)-4-oxa-1-azabicyclo[3.2.0]-heptan-7-one

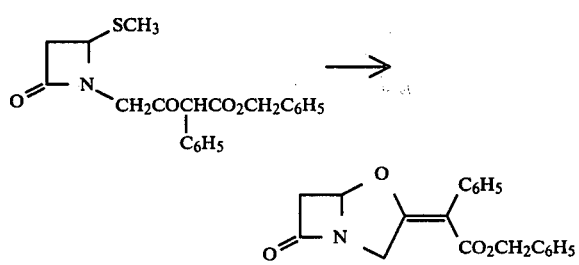

Benzyl 4-(4-methylthio-2-oxoazetidin-1-yl)-2-phenyl-3-oxobutyrate (70 mg., 0.183 mmole) was converted into the title compound using the process described in Example 11.2. The title compound was obtained as colourless needles (47 mg., 77% yield), m.p. 120°-121°. $\nu_{max}$ (EtOH): 245 nm (ε11,300). $\nu_{max}$ (CHCl$_3$): 1802 (β-lactam C=O), 1705 (ester C=O), 1640 (olefinic C=C) cm$^{-1}$. δ (CDCl$_3$): 2.99 (d, J 16Hz, 1H, C(6)H), 3.38 (dd, J 16, J' 2Hz, 1H, C(6)H), 4.02 (d, J 18Hz, 1H, C(2)H), 5.11 (s, 2H, OCH$_2$Ph), 5.12 (d, J 18Hz, 1H, C(2)H), 5.51 (d, J 2Hz, 1H, C(5)H), 7.25 (s, 10H, 2×C$_6$H$_5$). m/e: 335 (M+, 5%), 307 (1), 202 (2.5), 91 (100).

EXAMPLE 20

Sodium (E)-7-oxo-4-oxa-1-azabicyclo[3.2.0]heptane-3-(benzylidene-1-carboxylate)

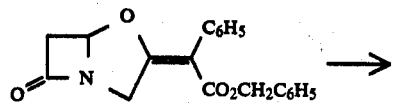

→

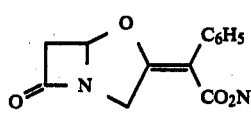

(E)-3-(1-Benzyloxycarbonylbenzylidene)-4-oxa-1-azabicyclo[3.2.0]heptan-7-one (28 mg.) was converted into the title compound using the process described in Example 7. The title compound was obtained as a colourless amorphous powder (23 mg.). $\nu_{max}$ (water): 241 nm (9,300). $\nu_{max}$ (KBr): 1780 (β-lactam C=O), 1650 (olefinic C=C), 1550 and 1380 (carboxylate) cm$^{-1}$. δ(D$_2$O): 2.89 (d, J 17Hz, 1H, C(6)H), 3.38 (dd, J 17, J' 2Hz, 1H, C(6)H), 3.90 (d, J 18Hz, 1H, C(2)H), 4.86 (d, J 18Hz, 1H, C(2)H), 5.50 (d, J 2Hz, 1H, C(5)H), 7.22 (s, 5H, C$_6$H$_5$).

EXAMPLE 21.1

1-(4-Methylthio-2-oxoazetidin-1-yl)-3-(p-nitrophenyl)-propan-2-one

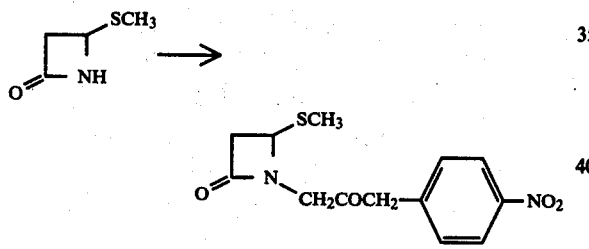

4-Methylthioazetidin-2-one (470 mg., 4 mmole) and 1-bromo-3-p-nitrophenylpropan-2-one (1.05 g., 4.07 mmole) were converted into the title compound using the process described in Example 1.1. The title compound was obtained as a yellow gum (176 mg., 15% yield). $\nu_{max}$ (CHCl$_3$): 1765 (β-lactam C=O), 1735 (ketone C=O), 1605 (aromatic C=C), 1530 and 1355 (aromatic NO$_2$) cm$^{-1}$. δ(CDCl$_3$): 1.98 (s, 3H, SCH$_3$), 2.98 (dd, J 15, J' 3Hz, 1H, β-lactam CHH), 3.42 (dd, J 15, J' 6Hz, 1H, β-lactam CHH), 3.80 (d, J 18Hz, 1H, NCHH), 3.88 (s, 2H, COCH$_2$Ar), 4.38 (d, J 18Hz, 1H, NCHH), 4.82 (dd, J 6, J' 3Hz, 1H β-lactam CH), 7.43 (d, J 8.5Hz, 2H, Ar-H), 8.22 (d, J 8.5Hz, 2H, Ar-H).

EXAMPLE 21.2

3-(p-Nitrobenzylidene)-4-oxa-1-azabicyclo[3.2.0]heptan-7-one

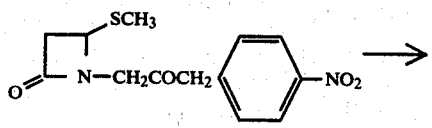

→

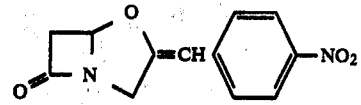

1-(4-Methylthio-2-oxoazetidin-1-yl)-3-(p-nitrophenyl)propan-2-one (159 mg.) was converted into the title compound using the process described in Example 11.2. The title compound was obtained as a yellow gum (13 mg.). (Found: M$^+$, 246.06381. C$_{12}$H$_{10}$N$_2$O$_4$ requires 246.06405). $\nu_{max}$ (EtOH): 337 nm. $\nu_{max}$ (CHCl$_3$): 1802 (β-lactam C=O), 1679 (olefinic C=C), 1600 (aromatic C=C), 1520 and 1350 (aromatic NO$_2$) cm$^{-1}$. δ(CDCl$_3$): 3.14 (d, J 16Hz, 1H, C(6)H), 3.56 (dd, J 16, J' 2Hz, 1H, C(6)H), 3.80 (d, J 17Hz, 1H, C(2)H), 4.62 (d, J 17Hz, 1H, C(2)H), 5.38 (s, 1H, olefinic H), 5.78 (d, J 2Hz, 1H, C(5)H), 7.60 (d, J 8.5Hz, 2H, Ar-H), 8.14 (d, J 8.5Hz, 2H, Ar-H). m/e: 246 (M$^+$, 75%), 218 (92), 204 (42), 176 (92), 175 (42), 162 (100), 130 (42), 129 (67), 119 (67).

EXAMPLE 22.1

3-(4-Methylthio-2-oxoazetidin-1-yl)-1-[o-(p-methoxybenzyloxycarbonyl)phenyl]-prop-1-yne

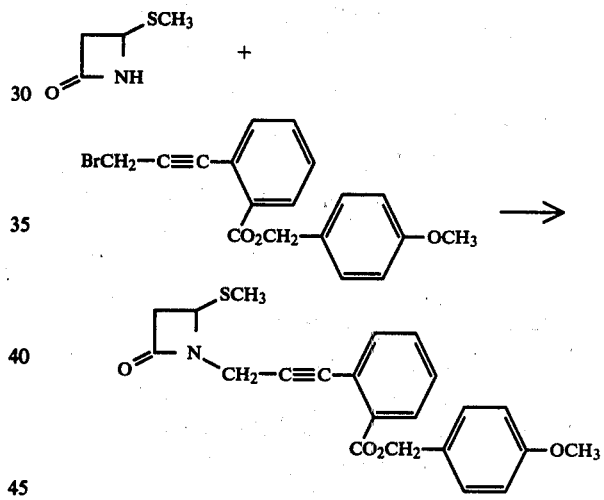

4-Methylthioazetidin-2-one (470 mg., 4 mmole) was dissolved in dry dimethylformamide (10 ml.) and the solution was stirred at −20° with exclusion of moisture while sodium hydride (50% dispersion in oil, 200 mg., 4 mmole) was added. When evolution of hydrogen had ceased (ca 10 minutes), 3-bromo-1-[o-(p-methoxybenzyloxycarbonyl)-phenyl]-prop-1-yne (1.44 g., 4 mmole) in dry dimethylformamide (5 ml.) was added dropwise to the stirred mixture at −20°. After addition of the bromide was complete, the mixture was warmed to 0° and stirred at that temperature for 30 minutes. The mixture was poured into ice-water (50 ml.) and the aqueous mixture was extracted twice with ethyl acetate (50 ml. portions). The combined ethyl acetate extracts were washed three times with water (30 ml. portions). The solution was dried (magnesium sulphate) and the solvent was evaporated under reduced pressure to yield a yellow gum. The gum was chromatographed on silica gel (25 g.) using ethyl acetate/petroleum ether (b.p. 60°–80°) to give the title compound as a colourless gum (400 mg., 26% yield). (Found: M$^+$, 395.11850. C$_{22}$H$_{21}$NO$_4$S requires 395.11912). $\nu_{max}$ (CHCl$_3$): 1760

(β-lactam C═O), 1730 (ester C═O), 1620 and 1520 (aromatic C═C) cm$^{-1}$. δ (CDCl$_3$): 2.10 (s, 3H, SCH$_3$), 2.91 (dd, J 15, J' 3 Hz, 1H, β-lactam CHH), 3.35 (dd, J 15, J' 6 Hz, 1H, β-lactam CHH), 3.75 (s, 3H, OCH$_3$), 3.86 (d, J 16.5 Hz, 1H, NCHH), 4.42 (d, J 16.5 Hz, 1H, NCHH), 4.94 (dd, J 6, J' 3 Hz, 1H, β-lactam CH), 5.35 (s, 2H, OCH$_2$Ar), 6.95 (d, J 8.5 Hz, 2H, Ar-H), 7.2–7.6 (m, 5H, Ar-H), 7.95 (m, 1H, Ar-H). m/e: 395 (M$^+$, 1%), 348 (14), 274 (63), 205 (37), 168 (56), 159 (68), 158 (44), 122 (76), 121 (100).

EXAMPLE 22.2

3-(4-Methylthio-2-oxoazetidin-1-yl)-1-[o-(p-methoxybenzyloxycarbonyl)-phenyl]-propan-2-one

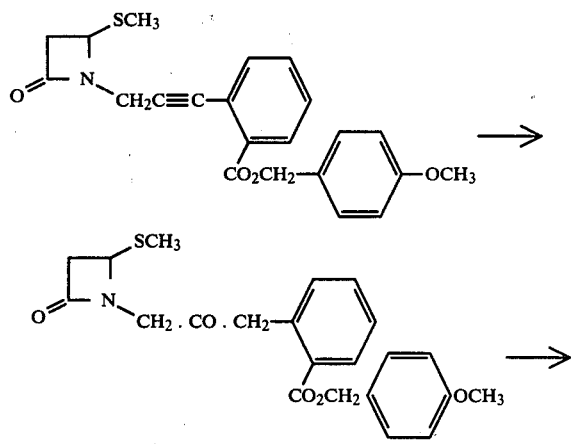

3-(4-Methylthio-2-oxoazetidin-1-yl)-1-[o-(p-methoxybenzyloxycarbonyl)-phenyl]-prop-1-yne (258 mg., 0.65 mmole) was dissolved in dry piperidine (6 ml.) and the solution was stirred at 40° for 3.5 hours. The piperidine was evaporated under reduced pressure and the residue was dissolved in ethyl acetate (50 ml.). The solution was washed twice with 0.1 N hydrochloric acid (30 ml. portions) and 5% sodium chloride solution (20 ml.). The solution was dried (magnesium sulphate) and the solvent was evaporated under reduced pressure to give the title compound as a colourless gum (245 mg., 91% yield). (Found: M$^+$, 413.12990. C$_{22}$H$_{23}$NO$_5$S requires 413.12968). ν$_{max}$(CHCl$_3$): 1760 (β-lactam C═O), 1730 (ester C═O), 1715 (ketone C═O), 1620 and 1520 (aromatic C═C) cm$^{-1}$. δ(CDCl$_3$); 2.02 (s, 3H, SCH$_3$), 2.95 (dd, J 15 J' 2.5 Hz, 1H, β-lactam CHH), 3.43 (dd, J 15 J' 5 Hz, 1H, β-lactam CHH), 3.77 (s, 3H, OCH$_3$), 3.93 (d, J 17 Hz, 1H, NCHH), 4.00 (s, 2H, COCH$_2$Ar), 4.45 (d, J 17 Hz, 1H, NCHH), 4.87 (dd, J 5, J' 2.5 Hz, 1H, β-lactam CH), 5.32 (s, 2H, OCH$_2$Ar), 6.95 (d, J 8.5 Hz, 1H, Ar-H), 7.2–7.6 (m, 5H, Ar-H), 8.10 (m, 1H, Ar-H). m/e: 413 (M$^+$, 5%), 365 (3), 324 (3), 292 (4), 277 (43), 230 (7), 228 (9), 121 (100).

EXAMPLE 22.3

3-[o-(p-Methoxybenzyloxycarbonyl)-benzylidene]-4-oxa-1-azabicyclo[3.2.0]heptan-7-one

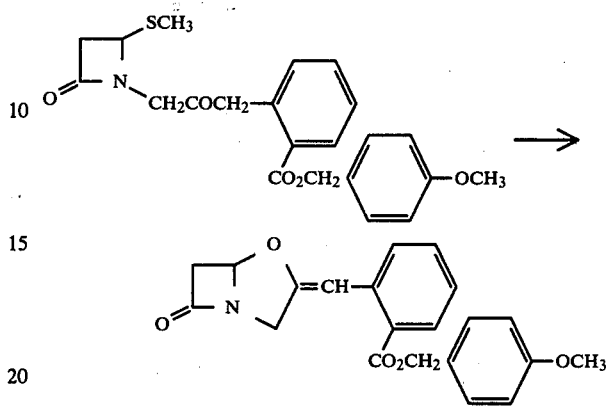

3-(4-Methylthio-2-oxoazetidin-1-yl)-1-[o-(p-methoxybenzyloxycarbonyl)-phenyl]-propan-2-one (76 mg.) was converted into the title compound using the process described in Example 11.2. The title compound was obtained as a colourless gum (9 mg.). ν$_{max}$(CHCl$_3$): 1795 (β-lactam C═O), 1715 (ester C═O), 1680 (sh.), (olefinic C═C), 1620 and 1520 (aromatic C═C) cm$^{-1}$. δ(CDCl$_3$): 3.02 (d, J 16 Hz, 1H, C(6)H), 3.43 (dd, J 16, J' 2.5 Hz, 1H, C(6)H), 3.50 (d, J 17 Hz, 1H, C(2)H), 3.76 (s, 3H, OCH$_3$), 4.47 (d, J 17 Hz, 1H, C(2)H), 5.22 (s, 3H, OCH$_2$Ar and olefinic H), 5.60 (d, J 2.5Hz, 1H, C(5)H), 6.90 (d, J 8.5 Hz, 2H, Ar-H), 7.1–7.5 (m, 5H, Ar-H), 7.90 (m 1H, Ar-H).

EXAMPLE 23.1

3-(4-Methylthio-2-oxoazetidin-1-yl)-1-[p-(p-methoxybenzyloxycarbonyl)-phenyl]-prop-1yne

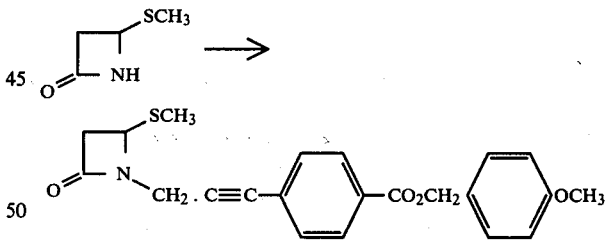

4-Methylthioazetidin-2-one (470 mg., 4 mmole) and 3-bromo-1-[p-(p-methoxybenzyloxycarbonyl)-phenyl]-prop-1-yne (1.44 g., 4 mmole) were converted into the title compound using the process described in Example 22.1. The title compound was obtained as a colourless gum (410 mg., 27% yield). ν$_{max}$ (CHCl$_3$): 1760 (β-lactam C═O), 1720 (ester C═O), 1610 and 1515 (aromatic C═C) cm$^{-1}$. δ(CDCl$_3$): 2.10 (s, 3H, SCH$_3$), 2.91 (dd, J 15.5, J' 2 Hz, 1H, β-lactam CHH), 3.34 (dd, J 15.5, J' 5 Hz, 1H, β-lactam CHH), 3.72 (s, 3H, OCH$_3$), 3.92 (d, J 17 Hz, 1H, NCHH), 4.40 (d, J 17 Hz, 1H, NCHH), 4.72 (dd, J 5, J' 2 Hz, 1H, β-lactam CH), 5.35 (s, 2H, OCH$_2$Ar), 6.93 (d, J 8 Hz, 2H, Ar-H), 7.42 (d, J 8 Hz, 2H, Ar-H), 7.48 (d, J 8.5 Hz, 2H, Ar-H), 8.03 (d, J 8.5 Hz, 1H, Ar-H).

EXAMPLE 23.2

3-(4-Methylthio-2-oxoazetidin-1yl)-1-[p-(p-methoxybenzyloxycarbonyl)-phenyl]-propan-2-one

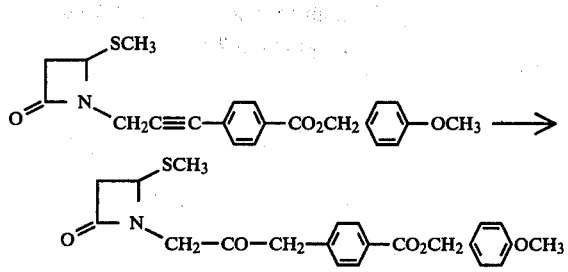

3-(4-Methylthio-2-oxoazetidin-1yl)-1-[p-(p-methoxybenzyloxycarbonyl)phenyl]-prop-2-yne (325 mg.) was converted into the title compound using the process described in Example 22.2. The title compound was obtained as a colourless gum (340 mg.). $v_{max}$ (CHCl$_3$): 1763 ($\beta$-lactam C=O), 1725 (br.) (ester and ketone C=O), 1620 and 1520 (aromatic C=C) cm$^{-1}$. $\delta$(CDCl$_3$): 1.98 (s, 3H, SCH$_3$), 2.94 (dd, J 16, J' 2.5 Hz, 1H, $\beta$-lactam CHH), 3.42 (dd, J 16, J' 5 Hz, 1H, $\beta$-lactam CHH), 3.72 (d, J 17 Hz, 1H, NCHH), 3.77 (s, 5H, OCH$_3$ and COCH$_2$Ar), 4.33 (d, J 17 Hz, 1H, NCHH), 4.76 (dd, J 5, J' 2.5 Hz, 1H, $\beta$-lactam CH), 5.35 (s, 2H, OCH$_2$Ar), 6.96 (d, J 8.5 Hz, 2H, Ar-H), 7.25–7.55 (m, 4H, Ar-H), 8.05 (d, J 8 Hz, 2H, Ar-H).

EXAMPLE 23.3

3-p-(p-Methoxybenzyloxycarbonyl)-benzylidene-4-oxa-1-azabicyclo[3.2.0]heptan-7-one

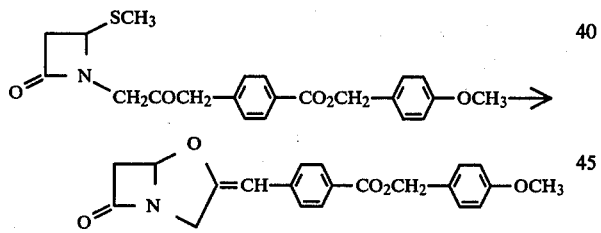

3-(4-Methylthio-2-oxoazetidin-1-yl)-1-[p-(p-methoxybenzyloxycarbonyl)-phenyl]-propan-2-one (93 mg.) was converted into the title compound using the process described in Example 11.2. The title compound was obtained as a colourless gum (5 mg.). (Found: M+, 365.12587. C$_{21}$H$_{19}$NO$_5$ requires 365.12631). $\lambda_{max}$ (EtOH): 297 nm ($\epsilon$ 17,200). $v_{max}$ (CHCl$_3$): 1800 ($\beta$-lactam C=O), 1715 (ester C=O), 1680 (olefinic C=O), 1610 and 1520 (aromatic C=O) cm$^{-1}$. $\delta$(CDCl$_3$): 3.05 (d, J 16 Hz, 1H, C(6)H), 3.49 (dd, J 16, J' 2 Hz, 1H, C(6)H), ca 3.7 (overlapped, 1H, C(2)H), 3.76 (s, 3H, OCH$_3$), 4.55 (d, J 15 Hz, 1H, C(2)H), 5.25 (s, 2H, OCH$_2$Ar), 5.32 (s, 1H, olefinic H), 5.71 (d, J 2 Hz, 1H, C(5)H), 6.88 (d, J 8 Hz, 2H, Ar-H), 7.35 (d, J 8 Hz, 2H, Ar-H), 7.52 (d, J 8.5 Hz, 2H, Ar-H), 7.95 (d, J 8.5 Hz, 2H, Ar-H). m/e: 365 (M+, 4%), 323 (3), 252 (6), 240 (4), 194 (9), 189 (28), 156 (28), 121 (72), 120 (100).

EXAMPLE 24.1

1-(4-Methylthio-2-oxoazetidin-1yl)-pentan-2,4-dione

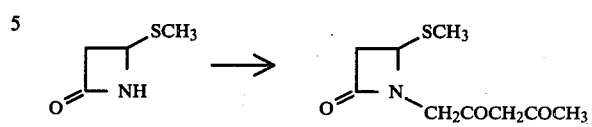

4-Methylthioazetidin-2-one (6.66 g., 57 mmole) and 1-bromopentan-2,4-dione (11.25 g., 63 mmole) were converted into the title compound using the process described in Example 1.1. The title compound was obtained as a colourless gum (3.13 g., 25% yield). $v_{max}$ (CHCl$_3$): 3400 (br.) (enol OH), 1760 ($\beta$-lactam C=O), 1720 (sh.) (ketone C=O), 1630 (sh.) and 1605 (enolic $\beta$-diketone C=O) cm$^{-1}$. $\delta$(CDCl$_3$): 2.03 (s, 6H, COCH$_3$ and SCH$_3$), 2.97 (dd, J 16, J' 2 Hz, 1H, $\beta$-lactam CHH), 3.41 (dd, J 16, J' 5 Hz, 1H, $\beta$-lactam CHH), 3.60 (s, 0.4H, COCH$_2$CO), 3.65 (d, J 17 Hz, 1H, NCHH), 4.18 (d, J 17 Hz, 1H, NCHH), 4.78 (dd, J 5, J' 2 Hz, 1H, $\beta$-lactam CH), 5.68 (s, 0.8H, olefinic H for enol), ca 14(v.broad, 0.8H, enolOH).

EXAMPLE 24.2

(Z)-3-(1-Chloro-2-oxopropylidene)-4-oxa-1-azabicyclo[3.2.0]heptan-7-one, (E)- and (Z)-3-(2-oxopropylidene)-4-oxa-1-azabicyclo[3.2.0]heptan-7-one

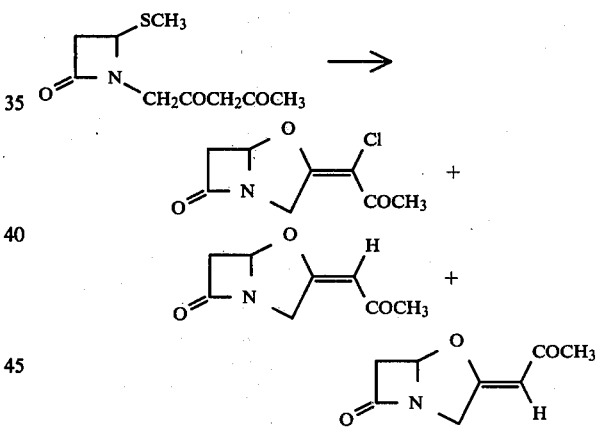

1-(2-Oxo-4-methylthioazetidin-1-yl)-pentan-2,4-dione(1.45 g.) was dissolved in dry methylene dichloride (75 ml.) and chlorine (480 mg.) in carbon tetrachloride (6 ml.) was added in one portion to the stirred ice-cooled solution. After addition of the chlorine, the cooling bath was removed and stirring was continued for 5 minutes. The solvent was then evaporated under reduced pressure to yield a yellow gum (1.4 g.). The gum was dissolved in dry DMF (20 ml.) and anhydrous, finely-powdered potassium carbonate (0.9 g.) was added.

The mixture was stirred at room temperature for one hour. The mixture was diluted with ethyl acetate (150 ml.) and was washed three times with water. The solution was dried (magnesium sulphate) and the solvent was evaporated under reduced pressure to yield a dark coloured gum (600 mg.). The gum was chromatographed on silica gel (30 g.) using ethyl acetate/petroleum ether (b.p. 60°–80°) to give, in order of elution, the following compounds.

(Z)-3-(1-Chloro-2-oxopropylidene)-4-azabicyclo[3.2.0]heptan-7-one as a colourless gum (64 mg.). (Found: M+, 201.01950. C₈H₈NO₃ ³⁵Cl requires 201.019265). λ$_{max}$ (EtOH): 268 nm. ν$_{max}$ (CHCl₃): 1805 (β-lactam C=O), 1682 (ketone C=O), 1600 (olefinic C=C) cm⁻¹. δ(CDCl₃): 2.35 (s, 3H, COCH₃), 3.15 (d, J 17 Hz, 1H, C(6)H), 3.55 (dd, J 17, J' 2 Hz, 1H, C(6)H), 3.90 (d, J 18 Hz, 1H, C(2)H), 4.98 (d, J 18 Hz, 1H, C(2)H), 5.70 (d, J 2 Hz, 1H, C(5)H). m/e: 203 (M+7%), 201 (M+, 19), 159 (12), 157 (10), 134 (14), 132 (41), 85 (87), 83 (100).

(E)-3-(2-Oxopropylidene)-4-oxa-1-azabicyclo[3.2.9-]heptan-7-one as colourless needles (139 mg.), m.p. 80°–82°. (Found: M+, 167.05812. C₈H₉NO₃ requires 167.05824). λ$_{max}$ (EtOH): 255 nm (ε 13,200). ν$_{max}$ (CHCl₃): 1800 (β-lactam C=O), 1690 (ketone C=O), 1605 (olefinic C=C) cm⁻¹. δ(CDCl₃): 2.12 (s, 3H, COCH₃), 3.15 (d, J 16 Hz, 1H, C(6)H), 3.46 (dd, J 16, J' 2 Hz, 1H, C(6H), 3.85 (br.d, J 18 Hz, 1H, C(2)H), 5.02(dd, J 18, J' 1.5 Hz, 1H, C(2)H), 5.54 (d, J 2 Hz, 1H, C(5)H), 5.88 (br. s, 1H, olefinic H). m/e: 167 (M+, 100%), 152 (36), 139 (39), 125 (77), 123 (31), 111 (25), 110 (55), 98 (90), 85 (77), 83 (100), 82 (45). (Z)-3-(2-Oxopropylidene)-4-oxa-1-azabicyclo[3.2.0]heptan-7-one as a colourless gum (15 mg.). (Found: M+, 167.05812. C₈H₉NO₃ requires 167.05824). ν$_{max}$ (CHCl₃): 1803 (β-lactam C=O), 1670 (ketone C=O), 1620 (olefinic C=C) cm⁻¹. δ(CDCl₃): 2.27 (s, 3H, COCH₃), 3.15 (d, J 16 Hz, 1H, C(6)H), 3.53 (dd, J 16, J' 2 Hz, 1H, C(6)H), 3.71 (d, J 16 Hz, 1H, C(2)H), 4.51 (d, J 16 Hz, 1H, C(2)H), 5.16 (s, 1H, olefinic H), 5.75 (d, J 2 Hz, 1H, C(5)H). m/e: 167 (M+, 50%), 152 (20), 139 (25), 125 (70), 123 (14), 111 (30), 110 (45), 98 (75), 85 (70), 83 (100), 82 (30).

EXAMPLE 25.1

1-(4-Methylthio-2-oxoazetidin-1-yl)-3-methylpentan-2,4-dione

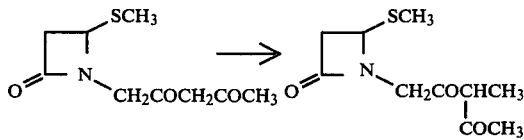

1-4-Methylthio-2-oxoazetidin-1-yl)-pentan-2,4-dione (920 mg., 4.28 mmole) was dissolved in dry dimethylformamide (10 ml.) and to the stirred, ice-cooled solution potassium carbonate (590 mg., 4.28 mmole) was added. The mixture was stirred and ice-cooled with exclusion of moisture while methyl iodide (610 mg., 4.3 mmole) in dry dimethylformamide (2 ml.) was added dropwise over 5 minutes. After addition was complete, the cooling bath was removed and stirring was continued for 1.5 hours. The mixture was then diluted with ethyl acetate (50 ml.) and was washed once with citric acid solution and twice with water. The solution was dried (magnesium sulphate) and the solvent was evaporated under reduced pressure to yield a dark coloured gum (900 mg.). The gum was chromatographed on silica gel (30 g.) using ethyl acetate/petroleum ether (b.p. 60°–80°) to give the title compound as a pale yellow gum (270 mg., 28% yield). ν$_{max}$ (CHCl₃): 3450 (br.) (enol OH), 1760 (β-lactam C=O), 1710 (ketone C=O), 1600 (br.) (enolised β-diketone) cm⁻¹. δ(CDCl₃): 1.34 (d, J 7 Hz, 2.1H, CHCH₃), 1.82 (s, 0.9H, enol=CCH₃), 1.98 (s, 3H, SCH₃), 2.18 (s, 3H, COCH₃), 2.93 (dd, J 15, J' 2 Hz, 1H, β-lactam CHH), 3.40 (dd, J 15, J' 5 Hz, 1H, β-lactam CHH), 3.55–4.90 (complex, ca 4H, NCH₂ Keto CHMe, β-lactam CH), 15.6 (s, 0.3H, enol OH).

EXAMPLE 25.2

(E)-3-(1-Methyl-2-oxopropylidene)-4-oxa-1-azabicyclo[3.2.0]-heptan-7-one

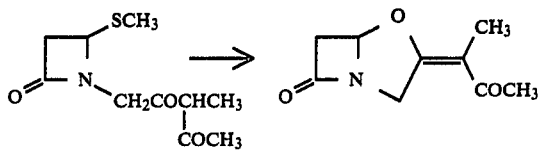

1-(4-Methylthio-2-oxoazetidin-1-yl)-3-methylpentan-2,4-dione (260 mg.) was converted into the title compound using the process described in Example 24.2. The title compound was obtained as a colourless gum (17 mg.). (Found: M+ 181.07388. C₉H₁₁NO₃ requires 181.07389). ν$_{max}$ (CHCl₃); 1797 (β-lactam C=O), 1685 (ketone C=O), 1605 (olefinic C=C) cm⁻¹. δ(CDCl₃): 1.95 (t, J 1 Hz, 3H, CH₃), 2.18 (s, 3H, COCH₃), 3.03 (d, J 16 Hz, 1H, C(6)H), 3.48 (dd, J 16, J' 2 Hz, 1H, C(6)H), 3.83 (br.d, J 18 Hz, 1H, C(2)H), 4.91 (dd, J 18, J' 1 Hz, 1H C(2)H), 5.54 (d, J 2 Hz, 1H, C(5)H). m/e: 181 (M+, 100%), 166 (28), 139 (36), 137 (58), 112 (58), 99 (39), 97 (29), 83(40).

EXAMPLE 26.1

Methyl 5-(4-Methylthio-2-oxoazetidin-1-yl)-2,4-dioxopentanoate

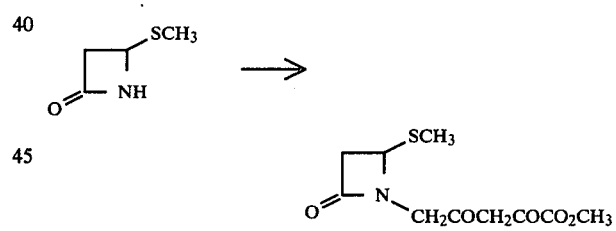

4-Methylthioazetidin-2-one (940 mg., 8 mmole) and methyl 5-bromo-2,4-dioxopentanoate (2.21 g., 10 mmole) were converted into the title compound using the process described in Example 24.1. The title compound was obtained as a pale yellow gum (550 mg., 27% yield). (Found: M+, 259.05113. C₁₀H₁₃NO₅S requires 259.05144). ν$_{max}$ (CHCl₃): 1750 (br.) (β-lactam and ester C=O), 1650 and 1600 (β-diketone C=O) cm⁻¹. δ(CDCl₃): 2.00 (s, 3H, SCH₃), 2.98 (dd, J 16 J' 2 Hz, 1H, β-lactam CHH), 3.43 (dd, J 16, J' 5 Hz, 1H, β-lactam CHH), 3.80 (s, 3H, OCH₃), 3.80 (d, J 17 Hz, 1H, NCHH), 4.31 (d, J 17 Hz, 1H, NCHH), 4.73 (dd, J 5, J' 2 Hz, 1H, β-lactam CH), 6.46 (s, 1H, enol, olefinic H), 11.8 (br.s, 1H, enol, OH). m/e: 259 (M+9%), 212 (100), 184 (8), 170 (19), 155 (28), 152 (40), 116 (80), 110 (95).

EXAMPLE 26.2

(E)-3-(2-Methoxycarbonyl-2-oxoethylidene)-4-oxa-1-azabicyclo[3.2.0]heptan-7-one

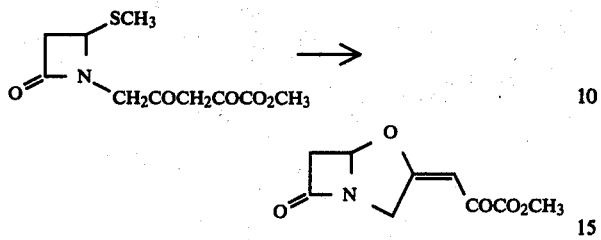

Methyl 5-(4-methylthio-2-oxoazetidin-1yl)-2,4-dioxopentanoate (550 mg.) was converted into the title compound using the process described in Example 24.2. The title compound was obtained as a colourless gum (14 mg., 3% yield). (Found: M+, 211.04789. C$_9$H$_9$NO$_5$ requires 211.04806). $\nu_{max}$ (CHCl$_3$): 1800 ($\beta$-lactam C=O), 1735 (ester C=O), 1690 (ketone C=O), 1615 (olefinic C=C) cm$^{-1}$. $\delta$(CDCl$_3$): 3.12 (d, J 16 Hz, 1H, C(6)H), 3.53 (dd, J 16, J' 2 Hz, 1H, C(6)H), 3.82 (s, 3H, OCH$_3$), 3.95 (br.d, J 19 Hz, 1H, C(2)H), 5.10 (dd, J 19, J' 1 Hz, 1H, C(2)H), 5.68 (d, J 2 Hz, 1H, C(5)H), 6.60 (t,J 1 Hz, 1H, olefinic H).

EXAMPLE 27

(E)-3-(2-Hydroxypropylidene)-4-oxa-1-azabicyclo[3.2.0]heptan-7-one

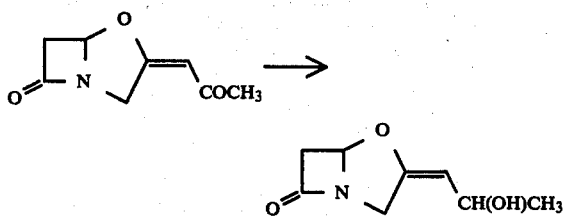

(E)-3-(2-Oxopropylidene)-4-oxa-1-azabicyclo[3.2.0]heptan-7-one (145 mg., 0.87 mmole) was dissolved in dry benzene (6 ml.) and the solution was stirred and ice-cooled under a dry nitrogen atmosphere while di-iso butyl aluminium hydride (20% solution in toluene, 0.7 ml., 0.98 mmole) was added dropwise. After addition, the mixture was stirred at 0° under dry nitrogen for 4 hours. The mixture was then diluted with ethyl acetate and the solution was shaken with saturated brine. The mixture was filtered, the filtrate was shaken, and the layers were separated. The ethyl acetate layer was dried (magnesium sulphate) and the solvent was evaporated under reduced pressure to give a yellow gum. The gum was chromatographed on silica gel (10 g.) using ethyl acetate/petroleum ether (b.p. 60°-80°) to give the two diastereomers of the title compound. Both isomers were obtained as colourless oils (3 mg. each) and had identical i.r. spectra. $\nu_{max}$ (CHCl$_3$): 3500 and 3360 (alcohol OH), 1790 ($\beta$-lactam C=O), 1690 (olefinic C=C) cm$^{-1}$.

EXAMPLE 28.1

1-(2-Oxo-4-methylthioazetidin-1-yl)-3-phenylsulphonylpropan-2-one

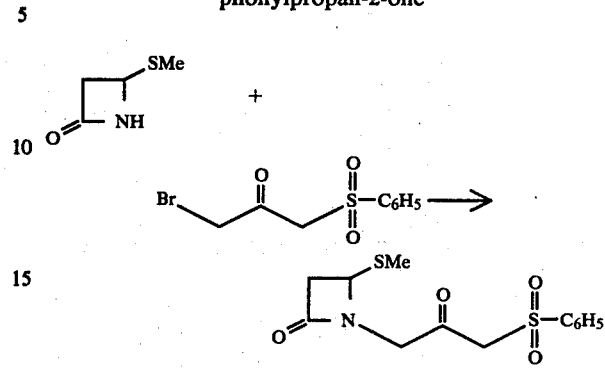

4-Methylthioazetidin-2-one (940 mg., 8 mmole) was dissolved in 1:1 dry DMF/dry 1,2-dimethoxyethane (25 ml) and the solution was stirred at −25° C. with exclusion of moisture while sodium hydride (50% dispersion in mineral oil, 820 mg., 17 mmole) was added in one portion. The mixture was stirred at −25° C. to −20° for 5 minutes after addition of the hydride. 1-Bromo-3-phenylsulphonylpropan-2-one (2.5 g., 9 mmole) in dry 1,2-dimethoxyethane (10 ml) was then added dropwise to the stirred mixture at −20°. After addition of the bromide, the mixture was warmed to 0° and was stirred at that temperature for 20 minutes. The mixture was then poured into ice-water (ca 100 ml) and the aqueous solution was acidified (pH 3) using citric acid solution. The mixture was stirred well with ethyl acetate (ca 100 ml) and was then filtered. The solid was washed several times with ethyl acetate. The filtrate and washings were shaken and the layers were separated. The organic layer was washed twice with water (2×50 ml), dried (magnesium sulphate), and the solvent was evaporated under reduced pressure to give a brown gum (2.8 g). The gum was chromatographed on silica gel (50 g) using ethyl acetate/petroleum ether to give the pure title compound as a colourless gum (1.22 g., 49% yield) which crystallised on storing at 4°. Recrystallisation from ethyl acetate/petroleum ether gave colourless crystals, m.p. 82°-84° (found: C, 49.78; H, 4.97; N, 4.21; S, 20.75. C$_{13}$H$_{15}$NO$_4$S$_2$ requires C, 49.85; H, 4.82; N, 4.47; S, 20.45%). $\nu$max. (CHCl$_3$): 1765 ($\beta$-lactam C=O), 1735 (ketone C=O), 1335 and 1160 (sulphone) cm$^{-1}$. $\delta$(CDCl$_3$): 2.00 (s, 3H, SCH$_3$), 2.92 (dd, J 15, 2.5 Hz, 1H, $\beta$-lactam CHH), 3.34 (dd, J 15, 4.5 Hz, 1H, $\beta$-lactam CHH), 3.96 (d, J 18 Hz, 1H, NCHH), 4.17 (s, 2H, CH$_2$SO$_2$Ph), 4.48 (d, J 18 Hz, 1H, NCHH), 4.68 (dd, J 4.5, 2.5 Hz, 1H, $\beta$-lactam CH), 7.4–8.0 (m, 5H, Ar-H).

EXAMPLE 28.2

1-(2-Oxo-4-chloroazetidin-1-yl)-3-phenylsulphonylpropan-2-one

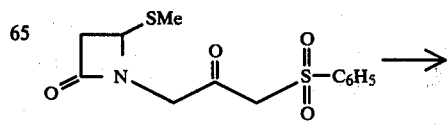

-continued

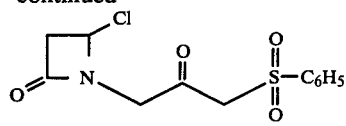

1-(2-Oxo-4-methylthioazetidin-1-yl)-3-phenylsulphonyl-propen-2-one (1.17 g., 3.7 mmole) was dissolved in 1:1 carbon tetrachloride/methylene dichloride (40 ml) and the solution was stirred and ice-cooled while chlorine (265 mg., 3.7 mmole) in carbon tetrachloride (6 ml) was added in one portion. After addition of the chlorine, the cooling bath was removed and the mixture was stirred for 3 minutes. The solvent was removed under reduced pressure to give the title compound as a colourless foam (1.12 g.). νmax. (CHCl₃): 1780 (β-lactam C=O), 1735 (ketone C=O), 1330 and 1160 (sulphone) cm⁻¹. δ(CDCl₃): 3.07 (dd, J 15, 1.5 Hz, 1H, β-lactam CHH), 3.56 (dd, J 15, 3.5 Hz, 1H, β-lactam CHH), 3.87 (d, J 18 Hz, 1H, NCHH), 4.09 (s, 2H, CH₂SO₂Ph), 4.45 (d, J 18 Hz, NCHH), 5.69 (dd, J 3.5, 1.5 Hz, 1H, β-lactam CH), 7.4–8.0 (m, 5H, Ar-H).

EXAMPLE 28.3

(E)- and (Z)-3-(Phenylsulphonylmethylene)-4-oxa-1-azabicyclo[3.2.0]heptan-7-one

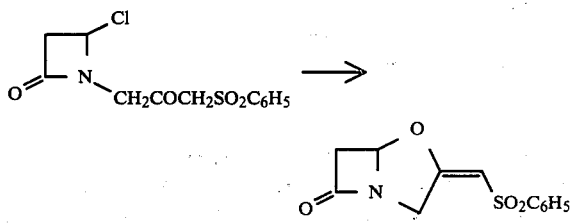

1-(4-Chloro-2-oxoazetidin-1-yl)-3-phenylsulphonyl-propan-2-one (1.12 g.) was dissolved in dry dimethylformamide (10 ml.) and anhydrous finely-powdered potassium carbonate (570 mg.) was added. The mixture was stirred with exclusion of moisture for 2 hours. More potassium carbonate (570 mg.) was added and stirring was continued for 2.5 hours. The mixture was diluted with ethyl acetate (100 ml.) and was washed three times with water. The solution was dried (magnesium sulphate) and the solvent was evaporated under reduced pressure to yield a dark coloured gum (260 mg.). The gum was chromatographed on silica gel (20 g.) using ethyl acetate/petroleum ether (b.p. 60°–80°) to give, in order of elution, the following compounds.

(E)-3-(Phenylsulphonylmethylene)-4-oxa-1-azabicyclo[3.2.0]heptan-7-one as a colourless gum (8.5 mg.). λmax (EtOH), 239 nm (ε 17,800). νmax (CHCl₃): 1808 (β-lactam C=O), 1650 (olefinic C=C), 1330 and 1160 (sulphone) cm⁻¹. δ(CDCl₃): 3.02 (d, J 17 Hz, 1H, C(6)H), 3.48 (dd, J 17, J' 2 Hz, 1H, C(6)H), 4.02 (br.d, J 18 Hz, 1H, C(2)H), 5.14 (dd, J 18, J' 1.5 Hz, 1H, C(2)H), 5.58 (d, J 2 Hz, 1H, C(5)H), 5.84 (t, J 1.5 Hz, 1H, olefinic H), 7.3–7.9 (m, 5H, Ar-H).

(Z)-3-(Phenylsulphonylmethylene)-4-oxa-1-azabicyclo[3.2.0]heptan-7-one as a colourless gum (8 mg.). λmax (EtOH): 240 nm. νmax (CHCl₃): 1808 (β-lactam C=O), 1670 (olefinic C=C), 1330 and 1160 (sulphone) cm⁻¹. δ(CDCl₃): 3.00 (d, J 17 Hz, 1H, C(6)H), 3.47 (br.d, J 17 Hz, 1H, C(6)H), 3.66 (d, J 16 Hz, 1H, C(2)H), 4.46 (d, J 16 Hz, 1H, C(2)H), 5.52 (s, 1H, olefinic H), 5.70 (br.s, 1H, C(5)H), 7.35–8.00 (m, 5H, Ar-H).

EXAMPLE 29.1

Methyl (4-methylthio-2-oxoazetidin-1-yl)acetate

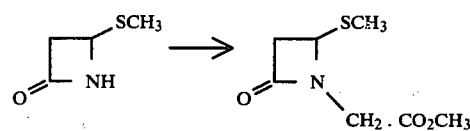

4-Methylthioazetidin-2-one (2.34 g, 20 mmole) was dissolved in dry dimethylformamide (40 ml) and treated at 0°–5° C. with sodium hydride (20 mmole). After 3 minutes methyl bromoacetate (3.37 g, 22 mmole) dissolved in dry dimethylformamide (20 ml) was added and the reaction mixture stirred for ¾ hour at 0°–5° C. After diluting with water (300 ml), the mixture was extracted with ethyl acetate (3×100 ml) and the extracts combined, washed with water, dried (MgSO₄) and evaporated. Chromatography of the residue on silica gel eluting with 30% ethyl acetate in petrolether provided methyl (4-methylthio-2-oxoazetidin-1-yl)acetate (2.4 g, 62%) as a mobile liquid. νmax (CHCl₃): 1760 (b), 1410, 1240, 1185 cm⁻¹; δ(CDCl₃): 2.13 (s, 3H, SCH₃); 2.95–3.75 (2H, AB of ABX, CH₂); 3.88 (s, 3H, OCH₃); 3.93 and 4.23 (2H, main peaks of ABq, J=18 Hz, NCH₂) and 5.02 (1H, X of ABX, CH).

EXAMPLE 29.2

1-methoxycarbonyl-1-(4-methylthio-2-oxoazetidin-1-yl)-3-phenyl-propan-2-one

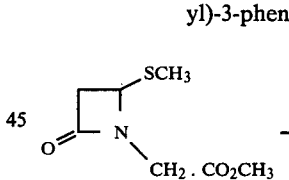

A solution of lithium 2,2,6,6-tetramethylpiperidide was prepared by adding butyl-lithium (2.0 ml of a 1.64 M solution in hexane) to a solution of 2,2,6,6-tetramethylpiperidine (0.45 g) in dry tetrahydrofuran (10 ml) at −70° C. under a nitrogen atmosphere. After 3 minutes a solution of methyl (4-methylthio-2-oxoazetidin-1-yl)acetate (0.346 g) in dry tetrahydrofuran (4 ml) was added quickly and the mixture stirred for 5 minutes at −70° C. A solution of phenylacetyl chloride (0.219 g) in dry tetrahydrofuran (4 ml) was then added quickly and the reaction allowed to proceed for 30 minutes at −70° C. and then 30 minutes during which time it warmed to 20° C. The mixture was acidifed with N hydrochloric acid at 0°–10° C. and extracted with ethyl acetate (3×50 ml). These extracts were combined, washed with water, dried (MgSO4) and evaporated. The residue (0.709 g) was chromatographed on silica gel eluting with 25% ethyl acetate in petrol-ether which provided the desired azetidinone (0.15 g, 37%) as a colourless gum which was a mixture of enolic isomers. $\nu_{max}$ (CHCl3): 3500, 1760 (b), 1655, 1605, 1440, 1400, 1355, 1260 cm$^{-1}$; δ(CDCl3): 2.00 and 2.06 (2s, 3H, SC$\underline{H}_3$); 2.7–3.6 (m, AB of ABX, 2H, C$\underline{H}_2$CH); 3.58, 4.09 (main peaks of ABq, J=17 Hz, C$\underline{H}_2$Ph); 3.69, 3.76 (2s, 3H, CO2C$\underline{H}_3$); 4.8 (m, 1H, C$\underline{H}$) and 7.37 (s, 5H, Ph-H) ppm. If Lithium bis (trimethylsilyl) amide is used as the base in this example the yield of keto ester rises to 90%.

EXAMPLE 29.3

Methyl (Z)-(2RS,5RS)-3-benzylidene-7-oxo-4-oxa-1-azabicyclo[3,2,0]-heptane-2-carboxylate

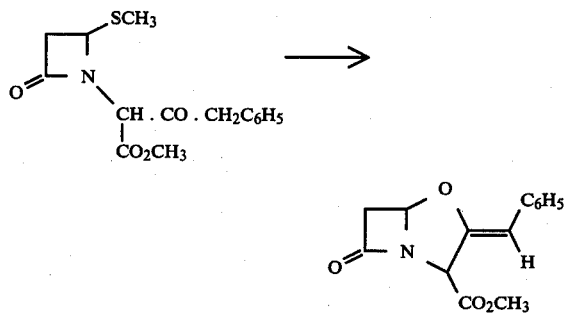

The β-ketoester (0.15 g, 0.5 mmole) was dissolved in dry carbon tetrachloride (3 ml) and treated with a solution of chlorine (1.1 equivalents) in carbon tetrachloride (0.44 ml). After 3 minutes at 20° C. the solution was evaporated to dryness to give the crude product as a colourless gum. [$\nu_{max}$ (CHCl3): 3500–3100, 1780, 1755, 1660, 1610, 1450, 1400, 1360, 1255 cm$^{-1}$]. The colourless gum was dissolved in dry dimethylformamide (3 ml) and treated at 20° C. with dry potassium carbonate (0.05 g), and the mixture stirred for 1.3 hours. After diluting with ethyl acetate (50 ml) the solution was washed with pH 7 phosphate buffer (5 ml) and then 5% sodium chloride solution (3×5 ml), dried (MgSO4) and the solution evaporated. The product was chromatographed on silica gel (15 g) eluting with 20% ethyl acetate in 60°–80° petrol-ether. The desired product was obtained as a colourless gum in 27% yield and was pure by thin layer chromatography. $\nu_{max}$ (CHCl3): 1800, 1755, 1680, 1315, 1120, 1050, 905 cm$^{-1}$; $\lambda_{max}$ (EtOH): 265 n.m. (ε 5800); δ(CDCl3): 3.16 (d, J=16 Hz, 1H, C6-H); 3.54 (dd, J=16 Hz, J'=2.5 Hz, 1H, C6-H); 3.78 (s, 3H, OC$\underline{H}_3$); 5.20 (bs, 1H, exchanges on treatment with D2O containing DBN, C3-H); 5.58 (bs, 1H, vinyl-H); 5.87 (d, J=2.5 Hz, 1H, C5-H); 7.1–7.6 (m, 5H, Ph-H) ppm.

EXAMPLE 30

Sodium (Z)-(2RS,5RS)-(3-benzylidene)-7-oxo-4-oxa-1-azabicyclo[3,2,0]-heptane-2-carboxylate

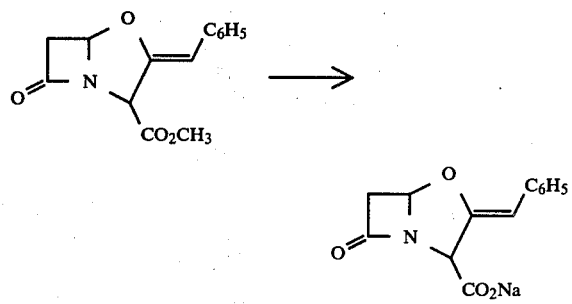

The methyl ester (0.041 g, 0.158 mmole) was dissolved in tetrahydrofuran (8 ml) and water (20 ml) and treated with N NaOH over 1.25 hours maintaining the pH at 9.5–9.8 by use of a pH-stat control. Thin layer chromatography showed complete loss of starting material and production of a single more polar component. (Rf in CHCl3:Me2CO:HOAc; 50:50:7=0.7). Adjustment of the pH to 7.0 using dilute HCl and freeze-drying gave the adequately pure sodium salt (0.035 g). $\nu_{max}$ (KBr): 1790, 1675, 1630, 1580 (b), 1395, 1315, 1200, 1110 cm$^{-1}$; δ(D2O) ($\underline{H}$OD at 4.45 ppm): 2.95 (d, J=17 1H); and 3.40 (dd, J=17, 2.6 Hz) (C6-H); 4.86 (s, 1H, C2-H); 5.47 (bs, 1H, =C$\underline{H}$); 5.67 (d, J=2.6 Hz, 1H, C5-H) and 7.0–7.5 (m, 5H, pH-H).

EXAMPLES 31–32

Example 31—Methyl (Z)-(2RS,5RS)-3-(4-nitrobenzylidene)-7-oxo-4-oxa-1-azabicyclo[3,2,0]heptane-2-carboxylate and Example 32—Methyl (Z)-(2RS,5RS)-3-(4-methoxybenzylidene)-7-oxo-4-oxa-1-azabicyclo[3,2,0]heptane-2-carboxylate These compounds were prepared in the manner of Example 29 using triethylamine in chloroform to effect the ring closure. (31) $\nu_{max}$ (CHCl3): 1800, 1751, 1767, 1592, 1510, 1341, cm$^{-1}$; δ(CDCl3): 3.17 (d, J=17 Hz, 1H, C6-H trans to C5-H); 3.60 (dd, J=17 and 3 Hz, 1H, C6-H cis to C5-H); 3.79 (s, 3H, OCH3); 5.21 (s, 1H, C2-H); 5.62 (s, 1H, =CH—); 5.91 (d, J=3 Hz, 1H, C5-H); 7.83 (ABq, 4H, aromatic CH); $\lambda_{max}$ (EtOH): 335.5 n.m. (ε=11800). (32) $\nu_{max}$ (CHCl3): 1795, 1748, 1674, 1603, 1508, 1248 cm$^{-1}$; δ(CDCl3): 3.10 (d, J=16.5 Hz, 1H, C6-H trans to C5-H); 3.51 (dd, J=16.5 Hz and 3 Hz, 1H, C6-H cis to C5-H); 3.75 (s, 3H, OCH3); 5.14 (s, 1H, C2-H); 5.49 (s, 1H, =CH—); 5.81 (d, J=3 Hz, 1H, C5-H); 7.10 (ABq, 4H, aromatic CH).

EXAMPLE 33

Methyl (Z)-(2RS,5RS)-3-(3-thienylmethylene)-7-oxo-4-oxa-1-azabicyclo[3,2,0]heptane-2-carboxylate

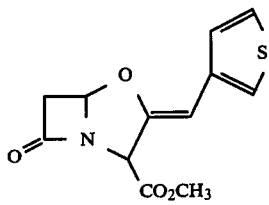

The title compound was prepared by the method of Example 29 using triethylamine in chloroform to effect the ring closure (69% yield). $\nu_{max}$ (CHCl$_3$): 1800, 1751, 1680, 1310 cm$^{-1}$; δ(CDCl$_3$): 3.09 (d, J=16.5 Hz, 1H, C6-H trans to C5-H); 3.51 (dd, J=16.5 and 3 Hz, 1H, C6-H cis to C5-H); 3.75 (s, 3H, OCH$_3$); 5.13 (s, 1H, C2-H); 5.64 (s, 1H, =CH—); 5.80 (d, J=3 Hz, 1H, C5-H); 7.1–7.4 (m, 3H, aromatic CH); $\lambda_{max}$(EtOH): 265 (ε=7850).

EXAMPLE 34

Sodium (Z)-(2RS,5RS)-3-(3-thienylmethylene)-7-oxo-4-oxa-1-azabicyclo[3,2,0]heptane-2-carboxylate

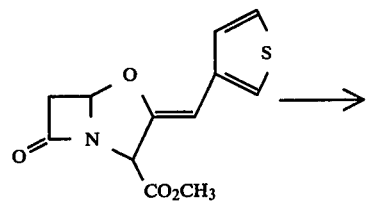

The title compound was prepared in 89% yield from its methyl ester by the method described in Example 30. $\nu_{max}$(KBr): 1780, 1677, 1620 (b), 1390, 1315, 1192, 1112 cm$^{-1}$; δ(D$_2$O) (HOD 4.45 ppm): 3.00 (d, J=17 Hz, 1H) and 3.60 (dd, J=17 and 2.8 Hz, 1H, C6-H); 4.86 (bs, 1H, C2-H); 5.60 (bs, 1H, =CH—); 5.68 (d, J 2.8 Hz, 1H, C5-H); and 7.1–7.4 (m, 3H, Ar-H).

EXAMPLES 35–37

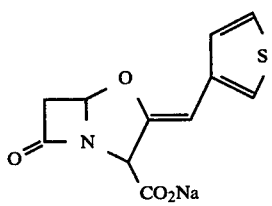

The compounds wherein R is a CH$_2$=CH$_2$ group (35), a CH=CH.C$_6$H$_5$ group (36) and a 2-furyl group (37) were prepared by the method of Example 33.

(35) $\nu_{max}$ (CHCl$_3$): 1800, 1750, 1670, 1305 cm$^{-1}$; δ(CDCl$_3$): 2.96 (d, J=16 Hz, 1H, C6-H trans to C5-H); 3.41,(dd, J=16 and 3 Hz, 1H, C6-H cis to C5-H); 3.66 (s, 3H, OCH$_3$); 4.8–7.1 (6H, C2-H+C5-H+vinyl-H); $\lambda_{max}$ (EtOH): 247 (ε=30200).

(36) $\nu_{max}$(CHCl$_3$): 1800, 1750, 1662, 1592, 1489, 1310 cm$^{-1}$; δ(CDCl$_3$): 3.06 (d, J=16.5 Hz, 1H, C6-H trans to C5-H); 3.48 (dd, J=16.5 and 3 Hz, 1H, 1H, C6-H cis to C5-H); 3.74 (s, 3H, OCH$_3$); 5.08 (s, 1H, C2-H); 5.43 (d, J=10 Hz, 1H, vinyl-H); 5.71 (d, J=3 Hz, 1H, C5-H); 6.3–7.0 (m, 2H, vinyl-H); 7.25 (bs, 5H, phenyl-H); $\lambda_{max}$ (EtOH): 307 (ε=10300).

(37) $\nu_{max}$(CHCl$_3$): 1805, 1750, 1680, 1640, 1435, 1310 cm$^{-1}$; δ(CDCl$_3$): 3.13 (d, J=16 Hz, 1H) and 3.50 (dd, J=16 and 2.5 Hz, 1H) (C6-H); 3.74 (s, 3H, OCH$_3$); 5.14 (bs, 1H, C2-H); 5.62 (bs, 1H, =CH); 5.80 (d, J=2.5 Hz, 1H, C5-H); 6.36 (m, 2H) and 7.28 (m, 1H) (furanyl-H); m/e: 249 (M$^+$).

EXAMPLE 38

(E)-(2SR,5RS)-2-hydroxymethyl-3-methoxycarbonyl-methylene-7-oxo-4-oxa-1-azabicyclo-[3,2,0]heptane

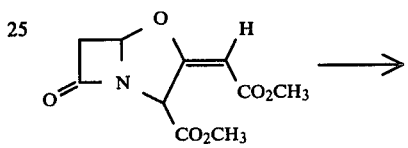

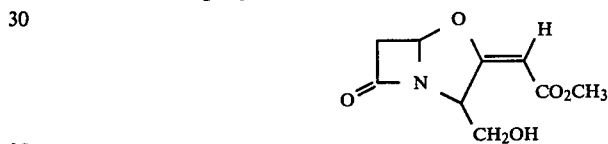

The diester (100 mg, 0.4 mmole) was dissolved in dry diethyl ether (10 ml). The cooled (0° C.), stirred solution was treated with LiAlH$_4$ (4 mg, 1 equivalent) and reaction allowed to proceed for 0.5 hour. After diluting with ether the solution was washed with diluted citric acid solution and water, dried and evaporated to a yellow oil (44 mg). Repeated chromatography of the product on a thick layer plate eluting with ethyl acetate-petrol ether provided the diester starting material (20 mg) and the title ester as a pale yellow oil (5 mg). $\nu_{max}$ (CHCl$_3$): 3300, 1795, 1695, 1645, 1115 cm$^{-1}$; δ(CDCl$_3$): 2.9–3.6 (m, 2H, C6-H); 3.62 (s, 3H, OCH$_3$); 3.86 (m, 2H, CH$_2$O); 5.3 (bt, 1H, C3-H); 5.48 (bs, 1H, =CH); 5.66 (m, 1H, C5-H).

EXAMPLE 39

(E)-(2RS, 5RS)-2-Carboxy-3-carboxymethylene-7-oxo-4-oxa-1-azabicyclo[3,2,0]heptane di-sodium salt

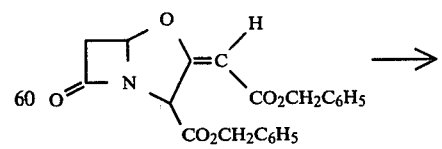

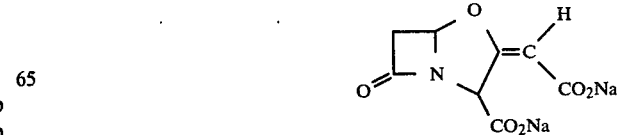

The dibenzyl ester (20 mg, 0.051 mmole) in dry tetrahydrofuran (20 ml) was hydrogenated for 20 minutes in the presence of 10% palladium charcoal (7 mg total). After filtration the procedure was repeated using fresh catalyst, and finally the filtered solution was hydrogenated for 3 hours in the presence of fresh 10% palladium charcoal (30 mg total). Thin layer chromatography examination showed hydrogenation to be complete. The filtered solution was diluted with water (10 ml) followed by the dropwise addition of dilute sodium bicarbonate solution to bring the pH to 7-7.5. After evaporation of the tetrahydrofuran in vacuo freeze-drying of the aqueous solution afforded the di-sodium salt as a pale yellow solid which was washed briefly with ether and air dried to give a product homogeneous by thin lyaer chromatography; $\nu_{max}$ (KBr): 1780 ($\beta$-lactam C=O), 1660-1590 (carboxylate $CO_2^-$) Rf~0.18 in $CHCl_3/(CH_3)_2CO/CH_3CO_2H$, 50:50:7.

Example 39 was repeated using dibenzyl ester (100 mg) and monitored by thin layer chromatography in chloroformacetone-acetic acid (50:50:7). A mono ester was identified by its Rf compared to that of the disodium salt. After a total of 6 hours hydrogenation, the catalyst was filtered off, the filtrate diluted with water and dilute $NaHCO_3$ solution added to bring the pH to 7.5. The aqueous solution was extracted with ether and then evaporated to dryness. Chromatography of the residue on silica gel (5 g), eluting with n-butanole-thanol-water (4:1:1) afforded a white solid (13 mg) identified as the title compound; $\nu_{max}$ (KBr): 1793, 1700, 1640 (b), 1380, 1110 $cm^{-1}$; $\lambda_{max}$ ($H_2O$): 244 nm ($\epsilon$7800).

EXAMPLE 41

Sodium
(E)-(2RS,5RS)-3-benzyloxycarbonylmethylene-7-oxo-4-oxa-1-azabicyclo[3,2,0]heptane-2-carboxylate

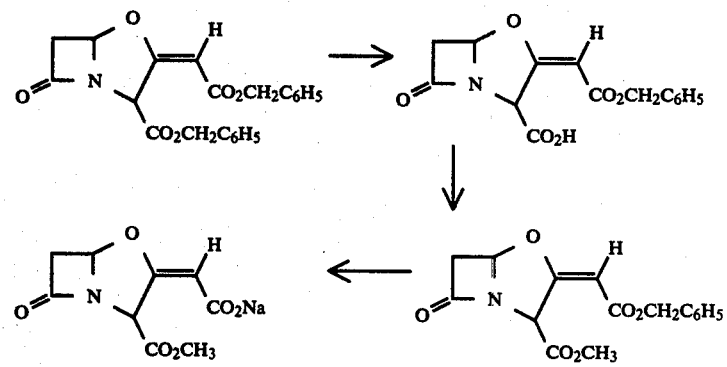

EXAMPLE 40

Sodium
(E)-(2RS,5RS)-3-benzyloxycarbonylmethylene-7-oxo-4-oxa-1-azabicyclo[3,2,0]heptane-2-carboxylate

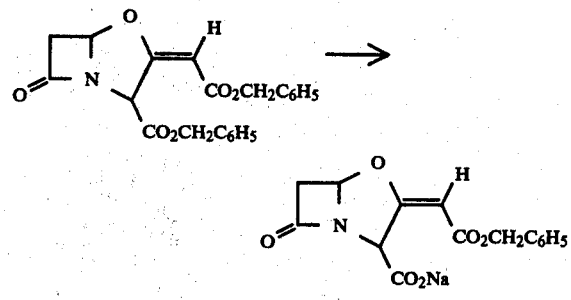

The dibenzyl ester (130 mg) in dry tetrahydrofuran (30 ml) was hydrogenated for 2-3 hours in the presence of 10% Pd/C (260 mg). After filtration, the tetrahydrofuran solution was treated with excess diazomethane.

Chromatography on silica gel provided the mixed diester as a colourless oil (13 mg). $\delta$($CDCl_3$): 3.08 (d, J=17, 1H) and 3.50 (dd, J=17 and 2.4 Hz, 1H) (C6-H), 3.68 (s, 3H, $OC\underline{H}_3$), 5.09 (s, 2H, $C\underline{H}_2Ph$), 5.60 (d, J=1.4 Hz, 1H) and 5.7 (m, 2H) (C2, C5 and $=C\underline{H}$). Hydrogenolysis of the latter in dry tetrahydrofuran (for 3 hours) in the presence of 10% Pd/C (20 mg) and working up as described in Example 39 provided the title compound as a colourless solid (5 mg), Rf 0.65 in chloroform:acetone:acetic acid (50:50:7).

EXAMPLE 42.1

Methyl
E-(2RS,5RS)-3-carbmethoxymethylene-7-oxo-4-oxa-1-azabicyclo[3,2,0]heptan-2-carboxylate

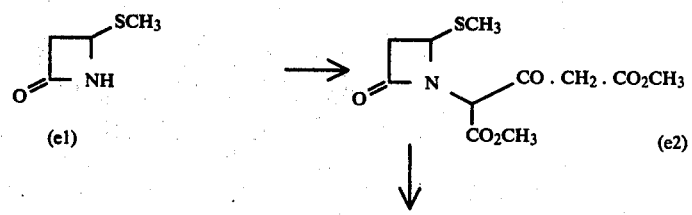

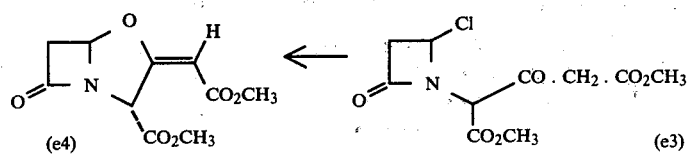

(a) 4-Methylthioazetidin-2-one (940 mg) (e1) in dry dimethylformamide (10 ml) was cooled to −20° C. and treated with sodium hydride (50% dispersion in oil, 1 g). After 5 minutes the resulting suspension was treated dropwise with dimethylbromoacetone dicarboxylate (2 g) and then stirred at 20° C. for 30 minutes. The mixture was diluted with ethyl acetate and washed with 10% citric acid solution (3×10 ml) and water (2×10 ml). The organic phase was dried (Na$_2$SO$_4$) and evaporated to yield a brown oil. This oil was chromatographed on silica gel (20 g) using ethyl acetate/petroleum ether (1:1) to yield the desired product (e2) as a yellow oil (490 mg). [$\nu_{max}$ (CHCl$_3$): 3500 - 3000 (enol OH), 1760 ($\beta$-lactam C=O), 1750 (ester C=O), 1660, 1620 (enol) cm$^{-1}$].

(b) The azetidinone (132 mg) (e2) in dry carbon tetrachloride (5 ml) at 0° C. was stirred during the addition of a solution of chlorine (32 mg) in carbon tetrachloride (2 ml). The mixture was stirred at 20° C. for 3 minutes and the solvent removed by evaporation. The residue was dissolved in carbon tetrachloride (5 ml) and re-evaporated. The crude chloro-azetidinone (145 mg) (e3) was obtained as a yellow oil. [$\nu_{max}$ (CHCl$_3$): 3500 - 3000 (enol OH), 1790 ($\beta$-lactam C=O), 1750 (ester C=O), 1670, 1620 (enol) cm$^{-1}$].

(c) The above yellow oil (145 mg) in dry dimethylformamide (5 ml) was stirred for 2 hours at 20° C. in the presence of finely powdered K$_2$CO$_3$ (200 mg). The mixture was then diluted with ethyl acetate (200 ml) and washed with water (3×10 ml). The organic layer was dried (Na$_2$SO$_4$) and evaporated to give a brown oil. A solution of the oil in diethyl ether was filtered through a short column of alumina to yield the title compound (e4) as a yellow oil (37 mg). [$\nu_{max}$ (CHCl$_3$): 1800 ($\beta$-lactam C=O), 1745 (ester C=O), 1710 (conjugated C=O), 1660 (C=C) cm$^{-1}$]. $\delta$(CDCl$_3$): 3.09 (1H, d, J=17 Hz, $\beta$-lactam CHH); 3.53 (1H, dd, J=17 Hz and 3 Hz, $\beta$-lactam CHH); 3.65 (3H, s, OCH$_3$); 3.76 (3H, s, OCH$_3$); 5.57 (1H, d, J=1 Hz, vinyl-H); 5.68 (1H, d, J=1 Hz, CH, exchanges with D$_2$O); 5.72 (1H, d, J=3 Hz, $\beta$-lactam CH). $\lambda_{max}$ (EtOH): 234 ($\epsilon$8,440)n.m.

EXAMPLES 43–45

The ring closure step described in Example 42 may be repeated using the following times and bases:

| Base | Time | Yield |
|---|---|---|
| K$_2$CO$_3$ | 2 hours | 34% |
| K$_2$CO$_3$ | 6 hours | 21% |
| N(C$_2$H$_5$)$_3$ | 20 minutes | 34% |

The spectroscopic characteristics of the product of each of these reactions were substantially as described in Example 42.

EXAMPLE 46

Benzyl E-(2RS,5RS)-3-benzyloxycarbonylmethylene-7-oxo-4-oxa-1-azabicyclo[3,2,0]heptane-2-carboxylate

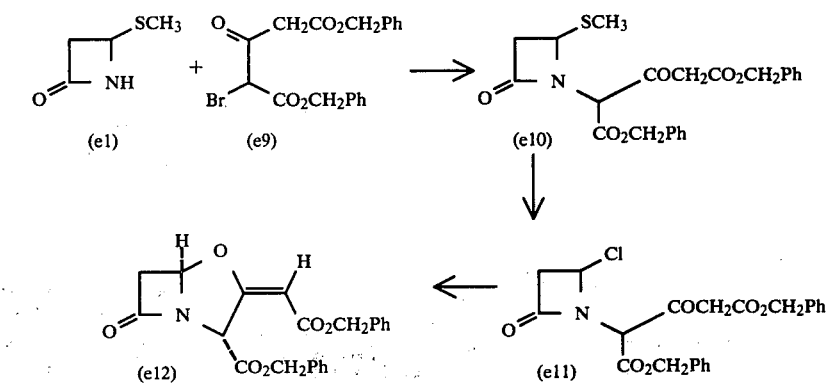

(a) 2-Methylthioazetidin-2-one (1.88 g, 16.0 mmol) in dry dimethylformamide (20 ml) was stirred at room temperature and treated with sodium hydride (1.60 g, 33.3 mmol, 50% suspension in oil) in small portions. A solution of the bromoester (e9) (6.50 g, 16.0 mmol) in dry dimethoxyethane (20 ml) was added dropwise to the above suspension over 10 minutes and stirring continued for a further 30 minutes. The reaction mixture was diluted with ethyl acetate (100 ml) and washed twice with 10% citric acid solution followed by water washing (3x). The organic layer was dried (Na$_2$SO$_4$) and the solvent removed to afford a brown oil which was chromatographed on silica gel (50 g). Elution with ethyl acetate-light petroleum (1:2) gave the desired product (e10) as a yellow oil (1.40 g, 20%); $\nu_{max}$ (CHCl$_3$): 3500-3300 (enol OH), 1760-1720 ($\beta$-lactam C=O and CO.OCH$_2$C$_6$H$_5$), 1670, 1630, 1580, 1500 cm$^{-1}$; $\delta$(CDCl$_3$): 1.90 (3H, s, SCH$_3$); 2.73 (1, dd, J=16 Hz and 3 Hz, $\beta$-lactam CHH), 3.23 (1H, dd, J=16 Hz and 5 Hz, $\beta$-lactam CHH), 3.50 (2H, s, CH$_2$); 4.70 (1H, m, $\beta$-lactam CH); 5.23–5.37 (4H, complex, —OCH$_2$C$_6$H$_5$), 7.40 (10H, s, Aryl H) ppm.

(b) The alkylated methylthioazetidinone (e10) (1.00 g, 2.27 mmol) in carbon tetrachloride (20 ml) was cooled (0° C.) and stirred during the addition in one portion of a solution of chlorine (161 mg, 2.27 mmol) in carbon tetrachloride (2 ml). The mixture was stirred at room temperature for 5 minutes and the solvent removed under reduced pressure. The residue was dissolved in further carbon tetrachloride and again evaporated to afford the crude chloroacetidinone (e11) as a yellow oil (1.10 g); $\nu_{max}$(CHCl$_3$): 3500-300 (enol OH), 1790 ($\beta$-lactam C=O), 1745 (CO.OCH$_2$C$_6$H$_5$), 1665 and 1620 (enol) cm$^{-1}$;

(c) The crude chloroazetidinone (e11) (1.1 g) in dry dimethylformamide (20 ml) was stirred at room temperature in the presence of dry, distilled triethylamine (0.26 g, 2.60 mmol) for 25 minutes. The resulting red solution was diluted with ethyl acetate and washed with 10% citric acid solution followed by water. The organic layer was dried (MgSO$_4$) and evaporation of the solvent gave an oil which was again taken up in ethyl acetate and washed with water. Evaporation of the solvent and chromatography of the residue on silica gel (ca. 5 g), eluting with ethyl acetate-light petroleum (1:4), afforded the desired product (e12) as a pale yellow solid (285 mg, 32% from e10): $\nu_{max}$(CHCl$_3$): 1805, ($\beta$-lactam C=O), 1745 (CO.OCH$_2$C$_6$H$_5$), 1705 (conj. CO.OCH$_2$C$_6$H$_5$), 1660 (conj. C=C), 1120 (C—O) cm$^{-1}$; $\delta$(CHCl$_3$): 3.05 (1H, d, J=17 Hz, $\beta$-lactam CHH); 3.48 (1H, dd, J=17 Hz and 3 Hz, $\beta$-lactam CHH), 5.05 (2H, s, —OCH$_2$C$_6$H$_5$); 5.14 (2H, s, —OCH$_2$C$_6$H$_5$); 5.62 (1H, d, J=1 Hz, vinyl H); 5.67 (1H, d, J=3 Hz, $\beta$-lactam CH); 5.76 (1H, d, J=1 Hz, CH); 7.30 (10H, s, Aryl H) ppm.

EXAMPLE 47

Benzyl (E)-(2RS, 5RS)-3-methoxycarbonylmethylene-7-oxo-4-oxa-1-azabicyclo-[3.2.0.]-heptane-2-carboxylate and Methyl (E) (2RS, 5RS)-3-benzyloxycarbonylmethylene-7-oxo-4-oxa-1-azabicyclo-[3.2.0.]-heptane-2-carboxylate

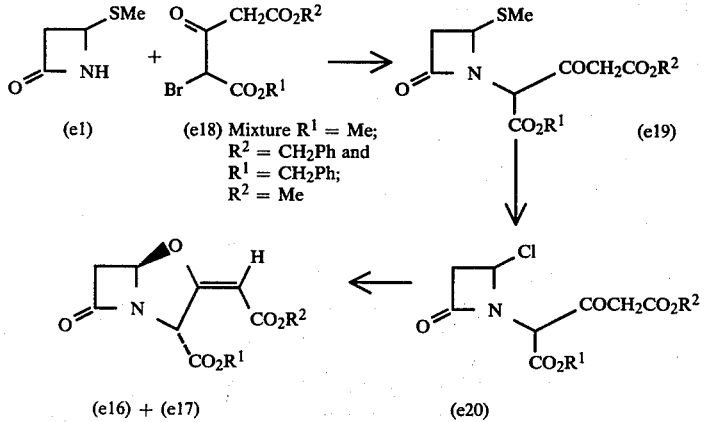

The procedure of Example 46 was followed. Thus the azetidinone (e 1) (2.5 g, 21.2 mmole) was alkylated with the mixture of bromo esters (e 18) in exactly the same way to afford after chromatography the desired mixture of diesters (e 19) as a pale yellow oil (1.60 g, 21%). $\nu_{max}$CHCl$_3$: 1730-1780

(b) 1660, 1610, 1425, 1595, 1550, 1245, 1220 cm$^{-1}$. $\delta$(CDCl$_3$) 1.97 (3H, s, SCH$_3$), 2.75 (1H, dd, J 16 and 3 Hz, $\beta$-lactam CHH), 3.25 (1H, dd, J 16 and 5 Hz, $\beta$-lactam CHH), 3.43 (2H, s, CH$_2$), 3.63 and 3.72 (3H, CO$_2$CH$_3$), 4.67 (1H, m, $\beta$-lactam CH), 5.03-5.26 (2H, complex, CH$_2$Ph)7.33 (5H, s, Arom H) ppm.

The mixture of diesters (e 19) (1.50 g, 4.1 mmole) was treated with chlorine as for Example 46. The crude mixture of chloro compound (e 20) was dissolved in dry DMF (20 mls) and treated at 0° with triethylamine (0.45 g, 4.5 mmole). Stirring was continued for 0.5 hr before being diluted with ethyl acetate and worked up as for Example 46. Chromatography of the crude reaction product on silica-gel eluting with ethyl acetate-petrol provided the desired mixture of diesters (e 16) and (e 17) as a pale yellow oil (0.32 g, 25%) $\nu_{max}$ (CHCl$_3$): 1800, 1745, 1705, 1655, 1335, 1120cm$^{-1}$. $\delta$(CDCl$_3$) 3.00 (1H, d, J=16 Hz), 3.46 (1H, dd, J=16 Hz and 3 Hz) 3.50 and 3.63 (3H, s, CO$_2$CH$_3$), 5.03 and 5.13 (2H, s, CO$_2$CH$_2$Ph), 5.57-5.75 (3H, complex), 7.30(5H, s, Arom H)ppm.

Careful chromatography of the mixture on silica-gel allowed the separation of the mixture into its components (e16) and (e 17) and $\delta$(CDCl$_3$) 3.03 (d,J=16.5, 1H) and 3.41 (dd, J=16.5, 2.5, 1H) (C6H) 3.58 (s, 3H, OCH$_3$), 5.05 (s, 2H, CH$_2$Ph), 5.6–5.8 (m, 3H, C2, C5 and =CH), and 7.3 (s, 5H, Ph-H). and 3.09 (d, J=17, 1H) and 3.47 (dd, J=17 and 3, 1H) (C6-H), 3.48 (s, 3H, OCH$_3$), 5.18 (s, 2H, CH$_2$Ph), 5.6–5.75 (m, 3H, C5, C2 and =CH) and 7.32 (s, 5H, Ph-H).

EXAMPLE 48

Methyl (E) (2RS,5RS)-3-(2-hydroxyethylidene)-7-oxo-4-oxa-1-azabicyclo-[3.2.0.]-heptane-2-carboxylate

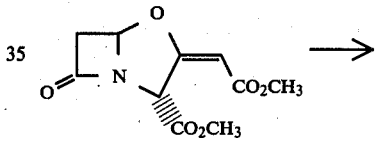

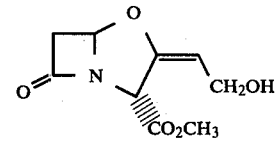

The diester (160 mg) in toluene (15 ml) was cooled to −70° and treated with a 20% solution of di-isobutyl aluminium hydride in toluene (0.25 ml, 0.5 equiv). Stirring at −70° continued for 1 hr and then the solution was allowed to warm to room temperature. Water was added and the organic layer diluted with benzene and washed with dil. HCl and water. Drying and evaporation of the solvent afforded an oil which was chromatographed on silica gel. Elution with ethyl acetate/petrol (1:1) gave unreacted starting material as a white solid (108 mg, 68%), followed by methyl isoclavulanate as a yellow oil (2 mg, 1%) νmax (CHCl₃): 3400, 1795, 1740 1680cm⁻¹; δ(CDCl₃) 2.98 (1H, d, J 16 Hz, C6H), 3.43 (1H, dd, J 16 and 3 Hz, C6H), 3.74 (3H, s, OC$\underline{H}$₃), 4.09 (2H, d, J 8 Hz, C$\underline{H}$₂O), 5.27 (1H, s, C2H), ca. 5.27 (1H, t, J 8 Hz, vinyl $\underline{H}$), 5.59 (1H, d, J 3 Hz, C5H) ppm.

EXAMPLE 49

Methyl (Z)-(2RS,5RS)-3-methoxycarbonylmethylene-7-oxo-4-oxa-1-azabicyclo[3.2.0]-heptane-2-carboxylate

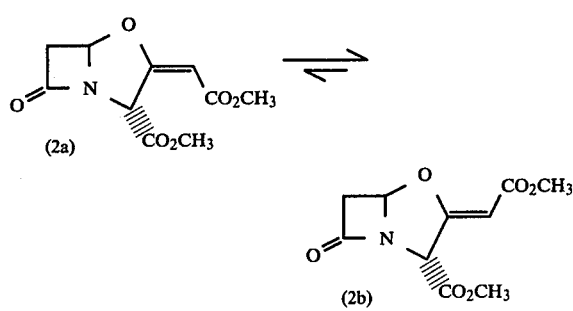

The diester (2a) (120 mg) in dry benzene (220 ml) was irradiated for 2¼ hrs using a low-pressure mercury lamp with water cooling. The solvent was removed in vacuo and the n.m.r. spectrum of the crude product indicated that it consisted of (2a) (59%) and (2b) (41%). Attempted isolation of (2b) by column chromatography failed and recovered starting material (2a) was isolated as a pale yellow solid (71 mg, 59%).

Ξ$_{max}$. (CHCl₃) (for 2a & 2b mixture): 1805, 1740, 1705, 1660, 1120 cm⁻¹; δ (CDCl₃) (for 2b) 5.14 (1H, d, J 1 Hz), 5.19 (1H, d, J 1 Hz), 5.91 (1H, d, J 2 Hz, C5H) ppm.

EXAMPLE 50

Methyl (Z)-(2SR,5RS)-3-(2-hydroxyethylidene)-7-oxo-4-oxa-1-azabicyclo-[3.2.0]-heptane-2-carboxylate

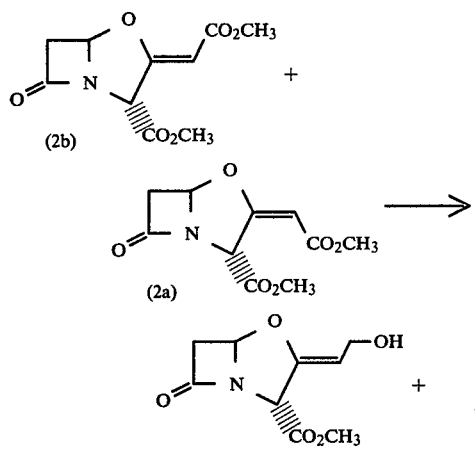

The mixture of esters (2a) and (2b) (190 mg) in dry toluene were cooled to −70° and treated with a 20% solution of di-isobutylaluminium hydride (0.6 ml, 1 equiv). The mixture was then stirred for 1 hr and allowed to warm to room temperature. Dilution with benzene, followed by washing with a little dilute HCl and water, afforded an oil on evaporation of the solvent. Chromatography on silica gel gave diester (2a) as a colourless solid (47 mg, 25%) followed by methyl isoclavulanate (1 mg, 1%) and methylclavulanate (1 mg, 1%) νmax (CHCl₃): 3400, 1795, 1740, 1680 cm⁻¹; δ(CDCl₃) 3.00 (1H, d, J 16 Hz, C6H), 3.45 (1H, d, J 16 Hz, C6H), 3.77 (3H, s, OC$\underline{H}$₃), 4.22 (2H, d, J 7 Hz, C$\underline{H}$₂O), 4.89 (1H, t, J 7 Hz, vinyl $\underline{H}$), 5.00 (1H, s, C2H), 5.65 (1H, m, C5H) ppm.

EXAMPLE 51

(Z)-(2SR,5RS)-2-hydroxymethyl-3-benzylidene-7-oxo-4-oxa-1-azabicyclo-[3.2.0]-heptane

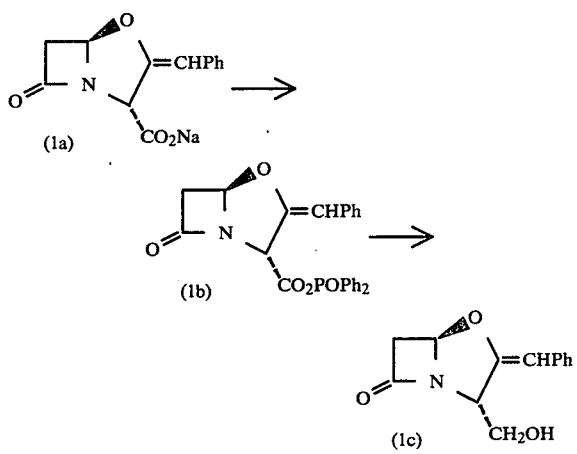

The sodium salt (1a) (0.112 g) (previously disclosed) was acidified by suspending in cold ether (30 mls) and adding N-HCl (0.84 ml). After washing with water, drying and evaporating the acid corresponding to (1a) was obtained as a colourless gum. ν$_{max}$ (CHCl₃): 1800, 1735, 1680 cm⁻¹. This compound in dry methylene chloride (5 mls) was cooled to −20° and treated in turn with N-methylmorpholine (0.038 g) and diphenyl phosphinylchloride (0.089 g). The mixed anhydride (1b) was allowed to form at −20° over 30 mins. The mixture was evaporated to give (1b) contaminated with the amine hydrochloride. ν$_{max}$(CHCl₃): 1805, 1175, 1675 cm⁻¹. A solution of this mixture (0.056 g) was redissolved in methylene chloride (2 ml), cooled to 5° and treated with tetra n-butylammonium borohydride (0.05 g) dissolved in methylene chloride (2 mls). After 30 mins the mixture was diluted with ether and washed H₂O (2xs), dried and evaporated. Column chromatography on silica gel eluting with ethylacetate-petrol-ether gave the desired compound (1c) (4 mgs) (18%) as a colourless gum. ν$_{max}$ (CHCl₃): 3360(b), 1795, 1680, 1305, 1110 cm⁻¹.

EXAMPLE 52

(E)-5-R- and
(E)-5-S-3-[N-(R-1-Phenylethyl)carbamoylmethylene]-
4-oxa-1-azabicyclo[3.2.0]heptan-7-one

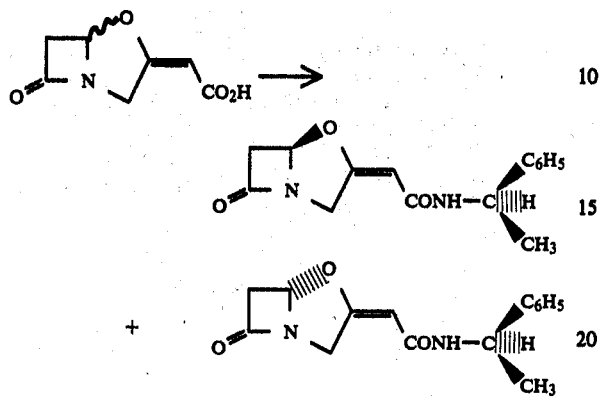

dl-(E)-7-oxo-4-oxa-1-azabicyclo[3.2.0]heptane-3-methylenecarboxylic acid in dry tetrahydrofuran (5 ml) was obtained by hydrogenolysis of the corresponding benzyl ester (130 mg, 0.5 mmole) as described in Example 7.

The tetrahydrofuran solution of the acid was stirred and ice-cooled while N-methylmorpholine (50 mg, 0.5 mmole) was added followed by diphenylphosphinic chloride (120 mg, 0.5 mmole). The mixture was stirred and ice-cooled with exclusion of moisture for 10 minutes. d-α-Phenylethylamine [60 mg, 0.5 mmole; $[\alpha]_D^{20} = +39°$ (neat)] was then added and the mixture was stirred and ice-cooled with exclusion of moisture for a further 2 hours. The mixture was diluted with ethyl acetate (50 ml) and was washed with 10% citric acid solution (20 ml), saturated sodium bicarbonate solution (20 ml), and saturated brine (20 ml). The solution was dried (magnesium sulphate) and the solvent was evaporated under reduced pressure to yield a yellow oil (100 mg). The oil was chromatographed on silica gel (15 g) using ethyl acetate/petroleum ether (b.p. 60°-80°) to give, in order of elution; (E)-5-R-3-[N-(R-1-Phenylethyl)carbamoylmethylene]-4-oxa-1-azabicyclo [3.2.0]heptan-7-one as a colourless gum (13 mg), $[\alpha]_D^{22} = +345°$ (c=0.6, CHCl₃), and (E)-5-S-[N-(R-1-Phenylethyl)carbamoylmethylene]-4-oxa-1-azabicyclo[3.2.0]heptan-7-one as a colourless gum (14 mg), $[\alpha]_D^{22} = -54.5°$ (c=0.35, CHCl₃). Both examples were better than 90% pure as judged by t.l.c. and n.m.r. spectroscopy.

Spectroscopic Data for the 5-R-epimer $\nu_{max}$ (CHCl₃): 3400, 3200 (amide NH), 1797 (β-lactam C═O), 1680 (amide I), 1625 (olefinic C═C), 1500 (amide II) cm⁻¹. $\lambda_{max}$ (EtOH): 237 nm. (CDCl₃): 1.44 (d, J 7 Hz, 3H, CH₃), 2.96 (d, J 16 Hz, 1H, C(6)H), 3.41 (dd, J 16, J', 2 Hz, 1H, C(6)H), 3.90 (d, J 18 Hz, 1H, C(2)H), 4.9-5.6 (complex, 5H, olefinic H, C(5)H, C(3)H, NH.CH), 7.20 (s, 5H, C₆H₅). m/e: 272 (M⁺, 2.2%), 216 (1.1), 188 (90), 120 (100).

The 5-S-epimer had u.v., i.r., n.m.r., and mass spectra identical to those described above for the 5-R-epimer.

| Source of enzyme | β-Lactamase inhibition: I₅₀ (μg/ml) | |
|---|---|---|
| | 5-R-epimer | 5-S-epimer |
| Staph. aureus Russell | 0.25 | 13.0 |
| Kleb. aerogenes E70 | 2.4 | >40 |
| Proteus mirabilis C889 | 0.6 | 8.8 |
| E. coli JT 4 | 0.4 | 5.8 |
| Pseudomonas aerogenosa Dalgleish | 0.65 | 17.6 |
| Pseudomonas aerogenosa A | 1.5 | 19 |
| Enterobacter P99 | 0.4 | 1.2 |

EXAMPLE 53

(E)-3-(1-Carbamoylbenzylidene)-4-oxa-1-azabicyclo[3.2.0]-heptan-7-one

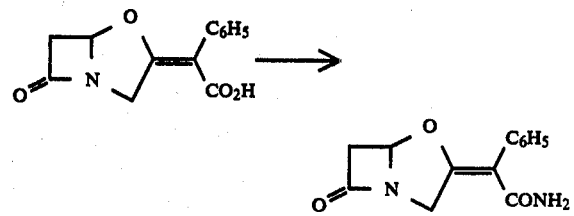

(E)-7-Oxo-4-oxa-1-azabicyclo[3.2.0]heptane-3-(benzylidene-1-carboxylic)acid (1.0 mmole) was converted into the title compound using the process described in Example 52. The title compound was obtained as a colourless prisms (28 mg.), m.p. 197°-99°. $\lambda_{max}$ (EtOH): 234.5 nm (ε=13,400). $\nu_{max}$ (CHCl₃): 3500, 3370 (amide NH₂); 1797 (β-lactam C═O), 1683 (amide C═O), 1620 (olefinic C═C), 1590 (amide II band) cm⁻¹.

EXAMPLE 54.1

Benzyl 1-(4-methylthio-2-oxoazetidin-1-yl)-1-(2-phenylacetyl)acetate

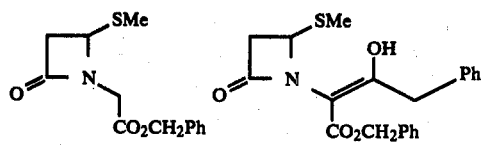

Benzyl (4-methylthio-2-oxoazetidin-1-yl)acetate (1.75 g, 6.6 mmole) was dissolved in dry THF (4 mls) and added to a solution of LiN(TMS)₂ prepared from hexamethyldisilazane (2.13 g, 13.2 mmole) and BuLi (1.7 M, 7.9 ml) in dry THF (20 mls) at −70°. After 5-7 mins at −70° phenylacetylchloride (0.92 ml, 7 mmole) dissolved in dry THF (4 mls) was added. Acidification with N-HCl (20 ml) after 45 mins was followed by extraction with ethyl acetate (3×40 mls). The combined extracts were washed with water (3 times), dried, evaporated and the residue chromatographed on silica gel. Elution with 20% ethyl acetate in petrol-ether provided benzyl 1-(4-methylthio-2-oxo-azetidin-1-yl)-1-(2-phenylacetyl)acetate as a colourless syrup (1.71 g, 84%).

$\nu_{max}$ (CHCl₃): 1760, 1650, 1600 (d), 1400, 1375, 1335, 1235 cm⁻¹.

EXAMPLE 54.2

Benzyl (Z)-(2RS,RS)-3-benzylidene-7-oxo-4-oxa-1-azabicyclo[3.2.0]heptane-2-carboxylate

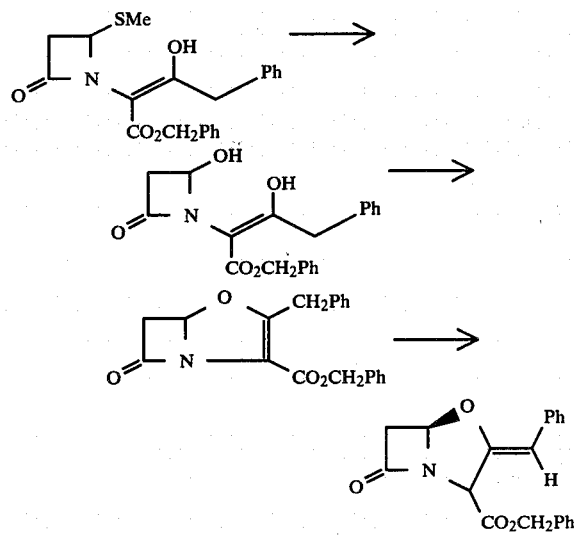

The ester from 54.1 (1.70 g) was dissolved in CCl$_4$ (50 mls) and treated at 18° with a solution of Cl$_2$ in CCl$_4$ (1.1 equivalents). After 4 minutes the solution was evaporated and the residue re-dissolved in CCl$_4$ and re-evaporated. The residue [$\nu_{max}$ (CHCl$_3$): 1785, 1655, 1600 (d), 1240 cm$^{-1}$] was dissolved in dry diethylether (50 mls) and treated with cooling to 0°–5° with Et$_3$N (0.72 ml), 1 equivalent). After 15 minutes at 18° the mixture was filtered and the filtrates evaporated. The residue [$\nu_{max}$ (CHCl$_3$): 1800, 1705, 1620 cm$^{-1}$] was re-dissolved in methylene chloride and treated at −18° with Et$_3$N (0.36 ml). After stirring for 18 hours the solution was evaporated. Chromatography on silica gel eluting with 20% ethyl acetate in petrol/ether provided the (Z)- ester (0.468 g, 21%) as a pale yellow oil: $\nu_{max}$ (CHCl$_3$): 1800, 1745, 1675, 1310, 1165, 1110 1010 cm$^{-1}$. δ(CDCl$_3$): 3.10 (d, 1H) and 3.50 (dd, J=16, 3 1H), (C6-H), 5.17 (2s, 3H, C2-H and PhCH$_2$), 5.50 (bs, 1H, =CH), 5.80 (d, J=3, 1H C5-H), and 7.1–7.5 (m, 10H, Ph-H).

EXAMPLE 55.1

Methyl (Z)-(2RS,5RS)-3-(2-thienylmethylene)-7-oxo-4-oxa-1-azabicyclo-[3.2.0]heptane-1-carboxylate

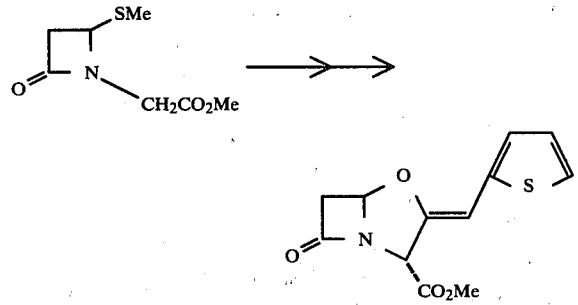

In the same manner as for the benzylidene derivative (Example 54) was prepared the title compound as a colourless oil $\nu_{max}$ (CHCl$_3$): 1800, 1750, 1678, 1310, 1232, 1008 cm$^{-1}$. δ(CDCl$_3$): 3.10 (d, J=16 Hz, 1H, C6-H trans to C5-H), 3.50 (dd, J=16 and 3 Hz, 1H, C6-H cis to C5-H), 3.73 (s, 3H, OCH$_3$), 5.13 (d, J=1 Hz, 1H, C2-H), 5.79–5.85 (m, 2H, =CH- and C5-H), 6.8–7.2 (m, 3H, aromatic-H), $\lambda_{max}$ (EtOH): 287 nm (ε=17350). m/e: 265 (M$^+$)

EXAMPLE 55.2

Sodium (Z)-(2RS,5RS)-3-(2-thienylmethylene)-7-oxo-4-oxa-1-azabicyclo-[3.2.0]heptane-2-carboxylate

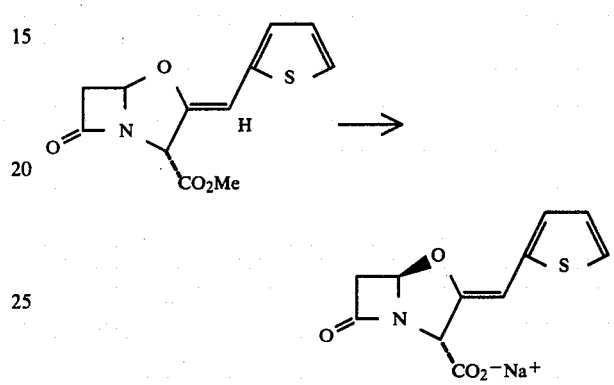

Hydrolysis of the ester from 55.1 according to the general method of Example 30 provided the title compound as a off-white solid in 85% yield. $\nu_{max}$ (KBr): 1790, 1673, 1630, 1400, 1312 cm$^{-1}$. δ (D$_2$O- ref HOD at 4.45δ): 2.97 (d, J=17 Hz, 1H, C6-H trans to C5-H), 3.42 (dd, J=17 and 2.5 Hz, 1H, C6-H cis to C5-H), 4.89 (s, 1H, C2-H), 5.68 (d, J=2.5 Hz, 1H, C5-H), 5.80 (s, 1H, =CH-), 6.8–7.3 (m, 3H aromatic -H). $\lambda_{max}$ (EtOH): 291.5 (ε=13410).

EXAMPLE 56

Sodium (Z)-(2RS,5RS)-3-p-nitrobenzylidene-7-oxo-4-oxa-1-azabicyclo-[3.2.0]heptane-2-carboxylate

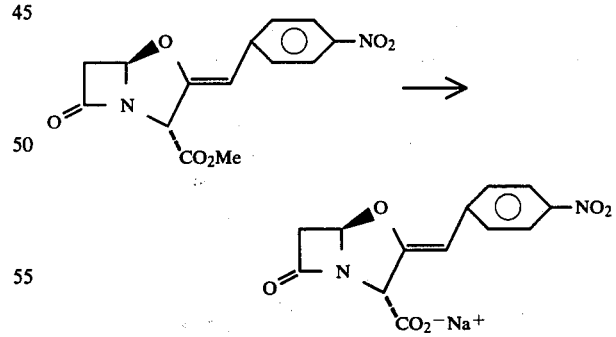

Hydrolysis of the ester from Example 31 according to the general method of Example 50 provided the title compound as a off-white solid in 65% yield. $\nu_{max}$(KBr): 1748, 1667, 1627, 1592, 1502, 1350 cm$^{-1}$. δ (D$_2$O - ref HOD=4.45δ): 3.03 (d, J=16.5 Hz, 1H, C6-H trans to C5-H); 3.49 (dd, J=16.5 and 2 Hz, 1H, C6-H cis to C5-H), 4.96 (s, 1H, C2-H), 5.58 (s, 1H, =CH-), 5.76 (d, J=2 Hz, 1H, C5-H), 7.57 and 7.90 (main peaks of ABq, 4H, aromatic H). $\lambda_{max}$ (EtOH): 238 nm (ε=7760) and 349 nm (ε=10300).

EXAMPLE 57

Sodium (Z)-(2RS,5RS)-3-(2-furanylmethylene)-7-oxo-4-oxa-1-azabicyclo-[3.2.0]heptane-2-carboxylate

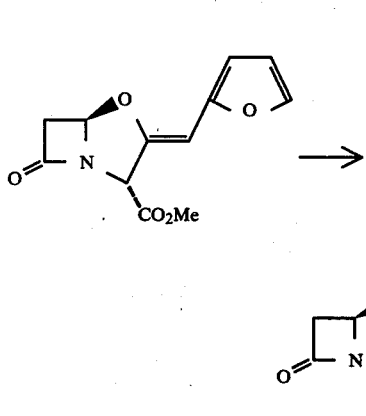

Hydrolysis of the ester from Example 37 according to the general method of Example 30 provided the title compound as a off-white solid in 83% yield. $\nu_{max}^{KBr}$: 1775, 1675, 1620(b), 1400, 1320, 1185 cm$^{-1}$. δ (D$_2$O, HOD at 4.45): 2.97 (d, J=17, 1H) and 3.44 (dd, J=17, 2.5, 1H) (C6-H), 4.89 (bs, 1H, C2-H), 5.53 (bs, 1H =C$\underline{H}$), 5.68 (d, J=2.5, 1H, C5-H), 6.3 (d, 2H) and 7.24 (d, 1H) (furan -H).

EXAMPLE 58.1

Methyl (Z)-(2RS,5RS)-3-(2-naphthylmethylene)-7-oxo-4-oxa-1-azabicyclo-[3.2.0]-heptane 2-carboxylate

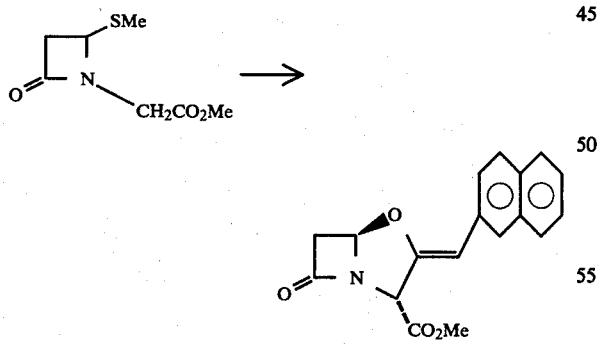

In the same manner as for the 3-benzylidene derivative (Example 54) was prepared the title compound as a colourless oil: $\nu_{max}^{CHCl_3}$ 1805, 1755, 1680, 1320, 1245, 1115, 1010 cm$^{-1}$; δ (CDCl$_3$): 3.13 (d, J=17, 1H), and 3.52 (dd, J=17, 2.5, 1H)(C6-H), 3.75 (s, 3H, OC$\underline{H}_3$) 5.19 (bs, 1H, C2-H), 5.66 (bs, 1H =C$\underline{H}$), 5.85 (d, J=2.5, 1H C5-H), and 7.3–7.9 (m, 7H, Ar-H).

EXAMPLE 58.2

Sodium (Z)-(2RS,5RS)-3-(2-naphthylmethylene)-7-oxo-4-oxa-1-azabicyclo-[3.2.0]heptane-2-carboxylate

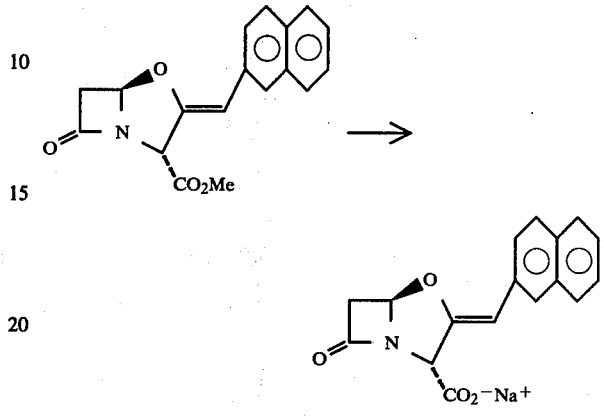

Hydrolysis of the ester from 58.1 according to the general method of Example 30 provided the title compound as a off-white solid in 65% yield: $\nu_{max}^{KBr}$ 1785, 1670, 1625, 1590 (s), 1395, 1315 cm$^{-1}$. δ (D$_2$O, HOD at 4.45): 2.38 (d, 1H) and 3.07 (dd, 1H), 4.79 (s, 1H, C2-H), 5.47 (bs, 2H =C$\underline{H}$ and C5-H), 6.9–7.6 (m, 7H, Ar-H).

EXAMPLE 59

Methyl (2RS,5RS)-2-deuterio-3-(3-thienylmethylene)-7-oxo-4-oxa-1-azabicyclo[3.2.0]-heptane-2-carboxylate

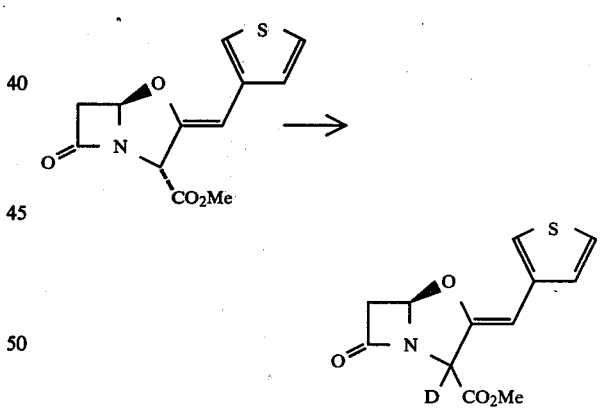

Methyl (2RS,5RS)-7-oxo-3-(3'-thienylmethylene)-4-oxa-1-azabicyclo[3.2.0]heptane-2-carboxylate (0.05 g, 0.19 mmole) (See Example 33) was dissolved in CDCl$_3$ and 1 drop D$_2$O and a trace of DBN added. After 1½ hours the solution was dried (MgSO$_4$) and evaporated and the residue chromatographed. The whole procedure was repeated to yield the 2-deutero compound (76%). $\nu_{max}$ (CHCl$_3$): 1798, 1743, 1678, 1308, 1268, 1021 cm$^{-1}$. δ (CDCl$_3$): 3.15 (d, J=17 Hz, 1H, C6-H trans to C5-H), 3.63 (dd, J=17 and 3 Hz, 1H, C6-H cis to C5-H), 3.83 (s, 3H, OCH$_3$), 5.78 (s, 1H, =CH-), 5.94 (d, J=3 Hz, 1H, C5-H), 7.2–7.5 (m, 3H, aromatic -H). $\lambda_{max}$ (EtOH): 223 nm (ε=8260), 265 nm (ε=7450). m/e: 266. 04712 (M$^+$); calculated for C$_{12}$H$_{10}$DNO$_4$S 266.04715.

EXAMPLE 60.1

2-(4-methylthio-2-oxo-azetidin-1-yl)-propionic acid

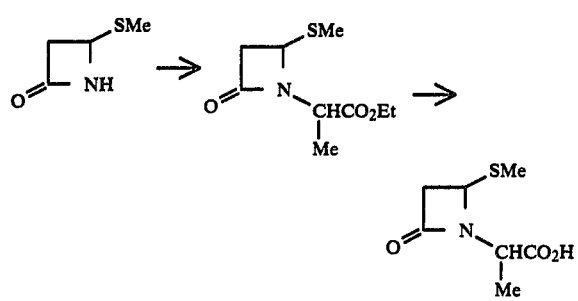

4-Methylthio-2-oxoazetidine (0.50 g, 4.25 mmole) in 8 ml DMF at 0°–5° C. was treated with NaH (4.25 mmole) and, after 15 minutes, with ethyl α-bromopropionate (0.85 g 4.7 mmole). The mixture was stirred for 1 hour at 0°–5° C., allowed to warm up over 2 hours and worked up by dilution with ethyl acetate and washing with water. The crude product was chromatographed to yield 62% ethyl 2-(4'-methylthio-2'-oxoazetidin-1'-yl)propionate. $\nu_{max}$ (CHCl$_3$): 1755, 1748, 1383, 1188 cm$^{-1}$. Ethyl 2-(4'-methylthio-2'-oxoazetidin-1'-yl)propionate (0.458 g, 2.11 mmole) in 3 ml MeOH at 0°–5° C. was treated dropwise over 1 hour with 2.11 ml 1 N NaOH and stirred a further ½ hour. The solution was diluted with water, ether washed, acidified to pH 2 and the 2-(4'-methylthio-2'-oxoazetidin-1'-yl)propionic acid extracted into ethyl acetate (86%). $\nu_{max}$ (CHCl$_3$): 1750, 1387, 1190 cm$^{-1}$. δ (CDCl$_3$): 1.60 and 1.68 (2d, 3H, CHC$\underline{H}_3$), 2.07 and 2.1 (2s, 3H, SCH$_3$), 2.97 (dd, J=15 and 2.5 Hz, 1H, C3-H trans to C4-H), 3.29 and 3.35 (2dd, J=15 and 14.5 Hz, 1H, C3-H cis to C4-H), 4.10 and 4.47 (2q, 1H, C$\underline{H}$CH$_3$), 4.73 and 4.98 (2dd, J=4.5 and 2.5 Hz, 1H, C4-H), 9.77 (s, 1H, COOH, D$_2$O exchanges).

EXAMPLE 60.2

(E)-2-methyl-3-(1-benzyloxycarbonylbenzylidene)-4-oxa-1-azabicyclo[3.2.0]heptan-7-one

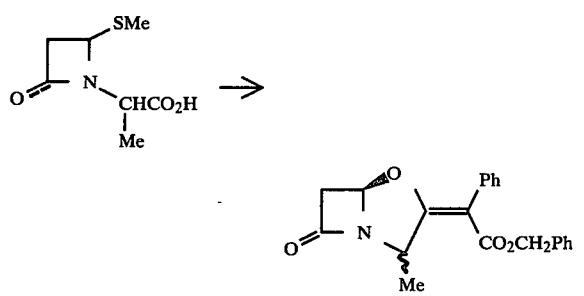

Transformation of the propionic acid derivative from 60.1 into the title compound was achieved essentially according to the details given in Example 19 The yield in the final cyclisation step using K$_2$CO$_3$ in DMF was 82%, and the product consisted of one major isomer and one minor isomer. $\nu_{max}$ (CHCl$_3$): 1793, 1700, 1630, 1305, 1165, 1048 cm$^{-1}$. δ(CDCl$_3$): 1.37 (major) and 1.75 (minor) (2d, 3H, CHC$\underline{H}_3$) 2.88 (d, J=16 Hz, 1H, C6-H trans to C5-H), 3.33 (dd, J=16 and 3 Hz, 1H, C6-H cis to C5-H), 5.10 (s, 2H, C$\underline{H}_2$Ph) 5.49 (q, 1H, C$\underline{H}$CH$_3$), 5.58 (d, J=3 Hz, 1H, C5-H), 7.2 (s, 10H, Ph). λ$_{max}$ (EtOH): 246.5 nm (ε=11700). m/e: 349 (M+)

EXAMPLE 60.3

Sodium (E)-2-methyl-7-oxo-4-oxa-1-azabicyclo[3.2.0]-heptane-3-benzylidene-1-carboxylate

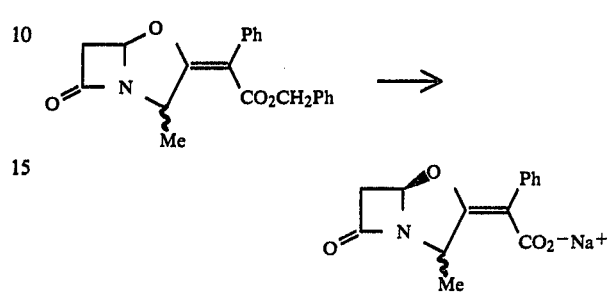

The hydrogenolysis of the ester from 60.2 was carried out by the process described in Example 20 providing the title compound as a colourless solid (97%). $\nu_{max}$ (KBr): 1780, 1650, 1560, 1380, 1310 cm$^{-1}$. δ(D$_2$O ref HOD=4.45δ): 1.16 (major) and 1.51 (minor) (2d, 3H, CHC$\underline{H}_3$), 2.72 (d, J=17 Hz, 1H, C6-H) trans to C5-H), 3.27 (dd, J=17 and 2 Hz, 1H, C6-H) cis to C5-H), 5.19 (q, 1H, C$\underline{H}$CH) 5.57 (d, J=2 Hz, 1H, C5-H), 3.17 (s, 5H, Ph). λ$_{max}$ (EtOH): 258.5 nm (ε=9530).

EXAMPLE 61

Methyl Z-(2RS, 5RS)-3-(pentafluorophenylmethylene)-7-oxo-4-oxa-1-azabicyclo[3.2.0]-heptane-2-carboxylate

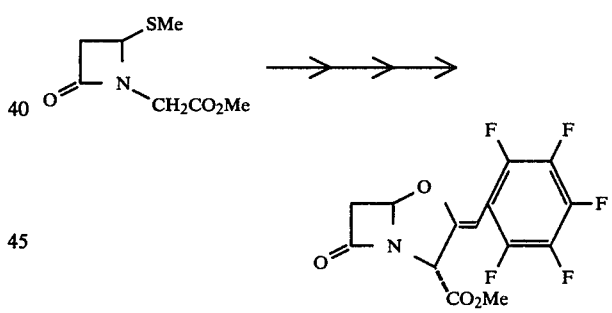

If pentafluorophenylacetyl chloride is substituted for the phenylacetyl chloride in the reactions described in Example 54, the title compound is obtained as a pale yellow coloured gum. $\nu_{max}^{CHCl_3}$: 1800, 1745, 1685, 1650, 1500, 1120 cm$^{-1}$; δ(CDCl$_3$): 3.08 (d, J=17, 1H) and 3.52 (dd, J=17, 2.5 1H) (C6-H) 3.90 (s, 3H, OC$\underline{H}_3$), 5.21 (bs, 1H, C2-H), 5.37 (bs, 1H, =C$\underline{H}$, and 5.77 (d, J=2.5, 1H, C5-H).

EXAMPLE 62.1

Ethyl (Z)-2-methyl-3-benzylidene-7-oxo-4-oxa-1-azabicyclo[3.2.0]-heptane-2-carboxylate

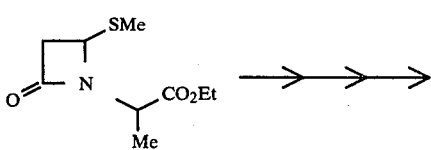

-continued

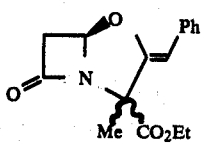

Reaction of Ethyl 2-(4-methylthio-2-oxoazetidin-1-yl)propionate (See Example 60) essentially according to Example 54 and using $K_2CO_3$ in DMF as the cyclisation agent provided the title compound as a colourless oil which was a mixture of one major and one minor isomer. Yield of the cyclisation step was 59%. $\nu_{max}$ (CHCl$_3$): 1792, 1735, 1678, 1259, 1030 cm$^{-1}$. $\delta$(CDCl$_3$): 1.24 (t, 3H, OCH$_2$CH$_3$), 1.59 (minor) and 1.93 (major) (2s, 3H, 2-CH$_3$), 3.08 (d, J=16 Hz, 1H, C6-H trans to C5-H major isomer), 3.41 (dd, J=16 and 2.5 Hz, 1H, C6-H cis to C5-H major isomer), 4.1 (major) and 4.19 (minor) (2q, 2H, OCH$_2$CH$_3$), 5.25 (minor) and 5.37 (major) (2s, 1H, =CH-), 5.52 (minor) and 5.72 (major) (2d, 1H, C5-H), 7.0–7.6 (m, 5H, Ph). $\lambda_{max}$ (EtOH): 270 nm ($\epsilon$=25300).

EXAMPLE 62.2

Sodium (Z)-2-methyl-3-benzylidene-7-oxo-4-oxa-1-azabicyclo[3.2.0]-heptane-2-carboxylate

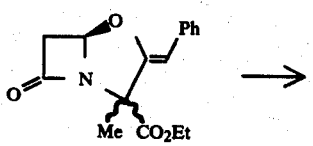

Ethyl (Z)-2-methyl-3-benzylidene-7-oxo-4-oxa-1-azabicyclo[3.2.0]-heptane-2-carboxylate (0.05 g, 0.174 mmole) was dissolved in 2 ml THF/2 ml H$_2$O, ice cooled and treated with 1 N NaOH (0.174 ml). After 2 hours the solution was ether washed, brought to pH 7 with dil. HCl and freeze dried to yield the title compound (82%) as a off-white solid. $\nu_{max}$ (KBr): 1772, 1673, 1600, 1390, 1208, 1034 cm$^{-1}$. $\delta$(D$_2$O—ref HOD=4.45$\delta$); 1.64 (s, 3H, 2-CH$_3$), 2.88 (d, J=17 Hz, 1H, C6-H trans to C5-H), 3.30 (dd, J=17 and 2.5 Hz, 1H, C6-H cis to C5-H), 5.40 (s, 1H, =CH-), 5.58 (d, J=2.5 Hz, 1H, C5-H), 7.0–7.6 (m, 5H, Ph). $\lambda_{max}$ (EtOH): 270 nm ($\epsilon$=18380).

EXAMPLE 63

Sodium (E)-(2RS, 5RS)-2-methoxycarbonyl-7-oxo-4-oxa-1-azabicyclo[3.2.0]-heptane 3-(methylene-1-carboxylate) and Sodium (E)-(2RS, 5RS)-3-Methoxycarbonylmethylene-7-oxo-4-oxa-1-azabicyclo[3.2.0]-heptane-2-carboxylate

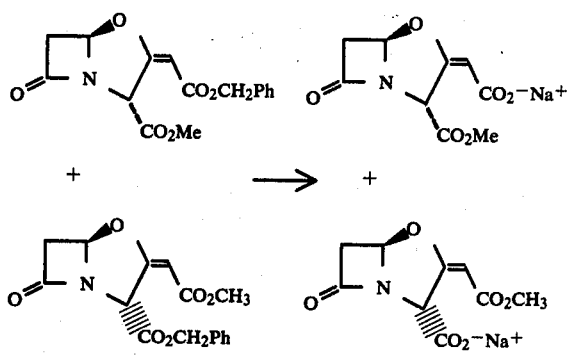

The mixture of diesters (136 mg) obtained in Example 47 was dissolved in tetrahydrofuran (50 ml) and stirred at room temperature for 2 hours in the presence of 10% palladium on charcoal (300 mg). The catalyst was then filtered. This purification procedure was carried out a second time with fresh catalyst. The purified material was then hydrogenated at atmospheric pressure over fresh Pd/C (300 mg).

The solution of acids thus obtained was diluted with water (50 ml) and neutralized with dilute sodium bicarbonate solution. Evaporation of the solvents at room temperature under high vacuum afforded a yellow powder which was chromatographed on silica gel eluting with n-butanol/ethanol/water (4:1:1)

The first title compound was obtained as a white solid (19 mg, 18%). $\nu_{max}$ (KBr) 1800, 1740, 1660 1130 cm$^{-1}$. $\delta$(D$_2$O) 3.00 (1H, d, J 17 Hz, $\beta$-lactam CHH), 3.42 (1H, dd, J 17 and 3 Hz, $\beta$-lactam CHH), 3.56 (3H, s, OCH$_3$), 5.38 (1H, d, J 1 Hz), 5.51 (1H, d, J 1 Hz), 5.59 (1H,m, $\beta$-lactam CH) ppm.

Continued elution afforded the second title compound as a white solid (34 mg, 32%). $\nu_{max}$ (KBr) 1790, 1700, 1650, 1120 cm$^{-1}$; $\delta$(D$_2$O) 3.21 (1H, d, J 17 Hz, $\beta$-lactam CHH), 3.64 (1H,dd, J 19 and 3 Hz, $\beta$-lactam CHH), 3.68 (3H, s, OCH$_3$), 5.53 and 5.58 (2H, d's, J 1 Hz vinyl H and C2-H), 5.84 (1H, d, J 3 Hz, $\beta$-lactam CH)ppm.; $\lambda_{max}$ (H$_2$O) 241 ($\epsilon$ 15,100) nm.

EXAMPLE 64.1

2(4-methylthio-2-oxo-azetidin-1-yl)-2-phenylacetic acid

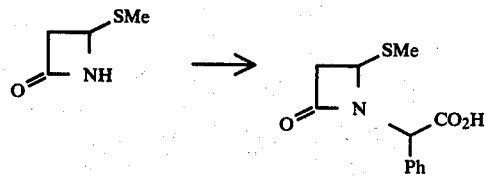

The reactions of 4-methylthio-azetidin-2-one to provide the title acid were accomplished essentially as described in Example 19 using methyl $\alpha$-bromophenylacetate. The title acid was obtained as a colourless gum: $\nu_{max}$ (CHCl$_3$) 1752, 1375, 1187 cm$^{-1}$. δ(CDCl$_3$): 1.65 and 1.90 (2s, 3H, SCH$_3$), 2.7-3.4 (m, 2H, C3-H), 4.52 and 4.93 (2dd, J=2.5 and 5 Hz, 1H, C4-H), 5.20 and 5.36 (2s, 1H, PhCH), 7.30 (bs, 5H, Ph), 9.79 (s, 1H, COOH, D$_2$O exchanges).

EXAMPLE 64.2

Benzyl 2-phenyl-7-oxo-4-oxa-1-azabicyclo-[3.2.0]-heptane-3-(benzylidene-1'-carboxylate)

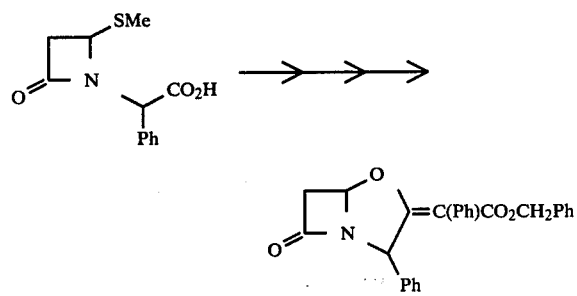

The conversion of the acetic acid derivative from 64.1 into the title compound was achieved essentially according to the details given in Example 19. The product was a colourless oil and was separable into 2 isomers of the title compound. The major isomer (39% yield in final cyclisation) had the following characteristics: $\nu_{max}$ (CHCl$_3$): 1795, 1702, 1635, 1302, 1048 cm$^{-1}$. δ(CDCl$_3$) 3.00 (d, J=16.5 Hz, 1H, C6-H trans to C5-H), 3.38 (dd, J=16.5 and 3 Hz, 1H, C6-H cis to C5-H), 4.96 (s, 2H, OCH$_2$Ph), 5.60 (d, J=3 Hz, 1H, C5-H), 6.50 (s, 1H, PhCH), 6.9-7.4 (m, 15H, phenyl).

EXAMPLE 64.3

Sodium 2-phenyl-7-oxo-4-oxa-1-azabicyclo[3.2.0]-heptane-3-(benzylidene-1'-carboxylate)

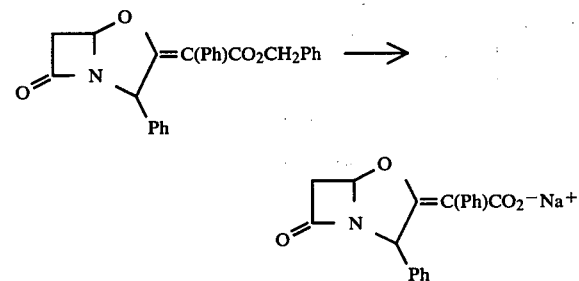

The major isomer from Example 64.2 was hydrogenolyzed according to the details given in Example 20. The title compound was obtained as a colourless solid (95% yield. $\nu_{max}$ (KBr): 1785, 1640 cm$^{-1}$. δ(D$_2$O—ref HOD at 4.45δ): 2.83 (d, J=17 Hz, 1H, C6-H trans to C5-H), 3.30 (dd, J=17 and 3 Hz, 1H, C6-H cis to C5-H) 5.57 (d, J=3 Hz, 1H, C5-H), 6.21 (s, 1H, PhCH), 7.17 and 7.23 (2bs, 10H, Ph). $\lambda_{max}$ (EtOH) 246 nm (ε=5000).

EXAMPLE 65

Methyl (Z)-(2RS, 5RS)-3-(2',5'-dichlorothien-3'-ylmethylene)-7-oxo-4-oxa-1-azabicyclo[3.2.0]-heptane-2-carboxylate

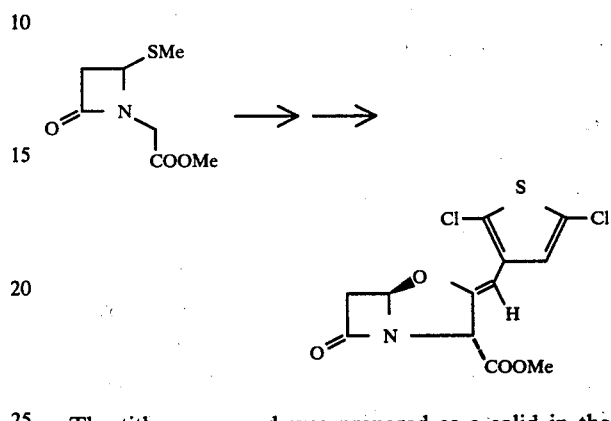

The title compound was prepared as a solid in the manner as for the 3-benzylidene derivative (Example 54). $\nu_{max}$ (CHCl$_3$): 1800, 1750, 1678, 1312, 1225, 1113 cm$^{-1}$. δ(CDCl$_3$): 3.10 (d, J=16 Hz, 1H, C6-H trans to C5-H), 3.53 (dd, J=16 and 2.5 Hz, 1H, C6-H cis to C5-H), 3.76 (s, 3H, OCH$_3$), 5.14 (d, J=1 Hz, 1H, C2-H), 5.58 (d, J=1 Hz, 1H, =CH-), 5.80 (d, J=2.5 Hz, 1H, C5-H), 7.24 (s, 1H, aromatic H). $\lambda_{max}$ (EtOH): 244 nm (ε=21,100), 278 nm (ε=14,680).

EXAMPLE 66

Lithium (Z)-(2RS, 5RS)-3-benzylidene-7-oxo-4-oxa-1-azabicyclo[3.2.0-]heptane-2-carboxylate

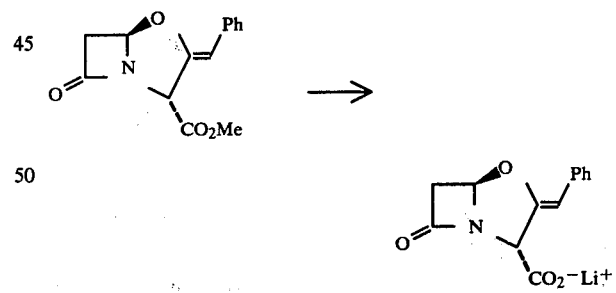

The ester (0.114 g) from Example 29 was hydrolysed according to Example 30 but replacing the N-NaOH solution by a N-LiOH solution. The freeze dried sample was crystallised from 95% ethanol, ethyl acetate and ether (2:1:1) as colourless needles m.p. 215°-220° dec; The compound was chromatographically homogeneous Rf 0.5 in Chloroform:acetic acid:acetone (50:7:50). The I.R. spectrum (KBr) was identical to the Na salt of Example 30.

EXAMPLES 67-71

| Example No. | R | R' | Yield (%) step (a) | step (b) |
|---|---|---|---|---|
| 67 | —$CO_2CH_2C_6H_5$ | $CH_2C_6H_5$ | 38 | 33 |
| 68 | $C_6H_5CH_2O$—⟨O⟩— | $CH_2C_6H_5$ | 10 | 58 |
| 69 | $O_2N$—⟨O⟩— | $CH_2C_6H_5$ | 21 | 23 |
| 70 | (thien-3-yl) | $CH_2C_6H_5$ | 8 | 49 |
| 71 | (thien-2-yl) | $CH_2$—⟨O⟩—$NO_2$ | 22 | 52 |

The compounds described in the above Table was prepared using the processes described in Examples 19.1 and 19.2. Spectroscopic properties of the bicyclic compounds are given below.

EXAMPLE 67
3-Di(benzyloxycarbonyl)methylene-4-oxa-1-azabicyclo[3.2.0]heptan-7-one Colourless gum. $\lambda_{max}$ (EtOH): 239 nm ($\epsilon$=15,800). $\nu_{max}$ (CHCl$_3$): 1802 ($\beta$-lactam C=O), 1720 (ester C=O), 1710 (ester C=O), 1640 (olefinic C=C)cm$^{-1}$. $\delta$(CDCl$_3$): 3.11 (d, J 16 Hz, 1H, C(6)H), 3.52 (dd, J 16, J' 2 Hz, 1H, C(6)H), 3.93 (d, J 18 Hz, 1H, C(2)H), 5.06 (d, J 18 Hz, 1H, C(2)H), 5.12 (s, 2H, OCH$_2$Ar), 5.18 (s, 2H, OCH$_2$Ar), 5.68 (d, J 2 Hz, 1H, C(5)H), 7.23 (s, 10H, Ar-H).

EXAMPLE 68
(E)-3-(1-Benzyloxycarbonyl-p-benzyloxy-benzylidene)-4-oxa-1-azabicyclo[3.2.0]heptan-7-one Colourless gum. $\nu_{max}$ (CHCl$_3$): 1800 ($\beta$-lactam C=O), 1705 (ester C=O), 1640 (olefinic C=C), 1610 and 1510 (aromatic C=C)cm$^{-1}$. $\delta$(CDCl$_3$): 3.00 (d, J 17 Hz, 1H, C(6)H), 3.42 (dd, J 17, J' 2 Hz, 1H, C(6)H), 4.01 (d, J 18 Hz, 1H, C(2)H), 5.00 (s, 2H, OCH$_2$Ar), 5.10 (d, J 18 Hz 1H, C(2)H), 5.12 (s, 2H, OCH$_2$Ar), 5.50 (d, J 2 Hz, 1H, C(5)H), 6.85–7.40 (complex, 14H, Ar-H).

EXAMPLE 69
(E)-3-(1-Benzyloxycarbonyl-p-nitrobenzylidene)-4-oxa-1-azabicyclo[3.2.0]heptan-7-one Pale yellow gum. $\lambda_{max}$ (EtOH): 297 ($\epsilon$=9,200), 2.46 ($\epsilon$ 16,000) nm. $\nu_{max}$ (CHCl$_3$): 1800 ($\beta$-lactam C=O), 1705 (ester C=O), 1630 (olefinic C=C), 1600 (aromatic C=C), 1515 and 1340 (aromatic NO$_2$) cm$^{-1}$. $\delta$(CDCl$_3$): 3.02 (d, J 17 Hz, 1H, C(6)H), 3.49 (dd, J 17, J' 2 Hz, 1H, C(6)H), 4.06 (d, J 18 Hz, 1H, C(2)H), 5.12 (s, 2H, OCH$_2$Ar), 5.15 (d, J 18 Hz, 1H, C(2)H), 5.58 (d, J 2 Hz, 1H, C(5)H), 7.22 (s, 5H, Ar-H), 7.36 (d, J 8 Hz, 2H, Ar-H), 8.12 (d, J 8 Hz, 28, Ar-H).

EXAMPLE 70
(E)-3-(Benzyloxycarbonyl-thien-3-yl-methylene)-4-oxa-1-azabicyclo[3.2.0]heptan-7-one Colourless gum. $\nu_{max}$ (CHCl$_3$): 1800 ($\beta$-lactam C=O), 1702 (ester C=O), 1630 (olefinic C=C) cm$^{-1}$. $\delta$(CDCl$_3$): 3.03 (d, J 16 Hz, 1H, C(6)H), 3.47 (dd, J 16, J' 2 Hz, 1 H, C(6)H), 4.00 (d, J 18 Hz, 1H, C(2)H), 5.08 (d, J 18 Hz, 1H, C(2)H), 5.15 (s, 2H, OCH$_2$Ar), 5.58 (d, J 2 Hz, 1H, C(5)H), 7.05–7.40 (complex, 8H, Ar-H).

EXAMPLE 71
(Z)-3-(p-Nitrobenzyloxycarbonyl-thien-2-yl-methylene)-4-oxa-1-azabicyclo[3.2.0]heptan-7-one Pale yellow gum. $\nu_{max}$ (EtOH): 268 ($\epsilon$ 17,600), 217 ($\epsilon$ 16,300) nm. $\nu_{max}$ (CHCl$_3$): 1800 ($\beta$-lactam C=O), 1705 (ester C=O), 1630 (olefinic C=C), 1600 (aromatic C=C), 1520 and 1340 (aromatic NO$_2$) cm$^{-1}$. $\delta$(CDCl$_3$): 3.08 (d, J 16 Hz, 1H, C(6)H), 3.51 (dd, J 16, J' 2 Hz, 1H, C(6)H), 4.03 (d, J 18 Hz, 1H, C(2)H), 5.10 (d, J 18 Hz, 1H, C(2)H), 5.25 (s, 2H, OCH$_2$Ar), 5.68 (d, J 2 Hz, 1H, C(5)H), 6.90–7.35 (complex, 3H, Ar-H) 7.40 (d, J 8 Hz 2H Ar-H), 8.13 (d, J 8 Hz, 2H, Ar-H).

EXAMPLE 72

Sodium (E)-7-oxo-4-oxa-1-azabicyclo[3.2.0]heptane-3-(p-hydroxybenzylidene-1-carboxylate)

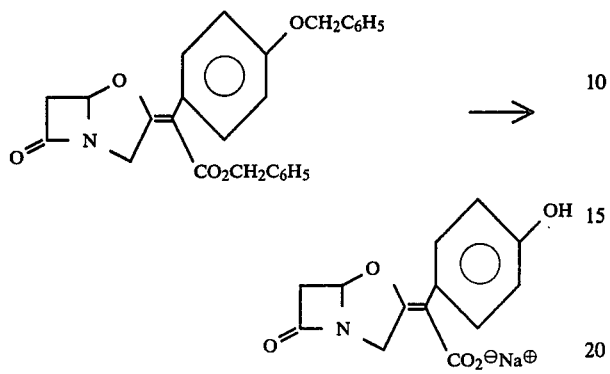

(E)-3-(1-Benzyloxycarbonyl-p-benzyloxybenzylidene)-4-oxa-1-azabicyclo[3.2.0]heptan-7-one (78 mg) in tetrahydrofuran (2 ml) was added to a mixture of 10% palladium-on-charcoal (80 mg) and tetrahydrofuran (5 ml) which had been shaken in a hydrogen atmosphere for 10 minutes. The mixture was then shaken under one atmosphere of hydrogen at room temperature for 2.5 hours. The catalyst was removed by filtration and was washed with tetrahydrofuran. To the combined filtrate and washings a solution of sodium bicarbonate (15 mg) in water (5 ml) was added. The tetrahydrofuran was evaporated under reduced pressure and the resulting aqueous residue was freeze-dried to give the title compound as a colourless amorphous powder (36 mg). $\lambda_{max}$(water): 220 ($\epsilon$ 15,000), 250 (sh.) ($\epsilon$ 11,150) nm. $\nu_{max}$ (KBr): 1785 ($\beta$-lactam C=O), 1660 (olefinic C=C), 1610 and 1510 (aromatic C=C), 1550 and 1375 (carboxylate) cm$^{-1}$. $\delta$(D$_2$O): 2.97 (d, J 16 Hz, 1H, C(6)H), 3.45 (dd, J 16, J' 2 Hz, 1H, C(6)H), 3.95 (d, J 17 Hz, 1H, C(2)H), 4.90 (d, J 17 Hz, 1H, C(2)H), 5.56 (d, J 2 Hz, 1H, C(5)H), 6.82 (d, J 8 Hz, 2H, Ar-H), 7.15 (d, J 8 Hz, 2H, Ar-H).

EXAMPLE 73

Sodium (Z)-7-oxo-4-oxa-1-azabicyclo[3.2.0]heptane-3-(thien-2-yl-methylenecarboxylate)

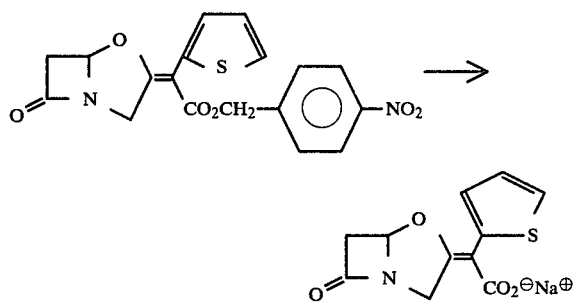

(Z)-3-(p-Nitrobenzyloxycarbonyl-thien-2-ylmethylene)-4-oxa-1-azabicyclo[3.2.0]heptan-7-one (60 mg) in tetrahydrofuran (2 ml) was added to a mixture of 10% palladium-on-charcoal (60 mg) and tetrahydroguran (5 ml) which has been shaken in a hydrogen atmosphere for 10 minutes. The mixture was then shaken under one atmosphere of hydrogen at room temperature for 3 hours. The catalyst was removed by filtration and was washed with tetrahydrofuran. To the combined filtrate and washings sodium bicarbonate (13 mg) in water (10 ml) was added. The tetrahydrofuran was evaporated under reduced pressure and the resulting aqueous residue was washed once with ether (10 ml). The aqueous solution was freeze-dried to give the title compound as a colourless amorphous powder (27 mg). $\lambda_{max}$(water): 229 ($\epsilon$ 8,200), 284 ($\epsilon$ 9,550)nm. $\nu_{max}$(KBr): 1782 ($\beta$-lactam C=O), 1660 (olefinic C=C), 1560 and 1380 (carboxylate)cm$^{-1}$. $\delta$(D$_2$O): 2.95 (d, J 16 Hz, 1H, C(6)H), 3.40 (dd, J 16, J' 2 Hz, 1H, C(6)H), 3.97 (d, J 17 Hz, 1H, C(2)H), 4.86 (d, J 17 Hz, 1H, C(2)H), 5.58 (d, J 2 Hz, 1H, C(5)H), 6.8–7.0 (m, 2H, Ar-H), 7.18 (br. d, J 5 Hz, 1H, Ar-H).

EXAMPLE 74

Sodium (Z)-7-OxO-4-oxa-1-azabicyclo[3.2.0]heptane-3-methylenecarboxylate

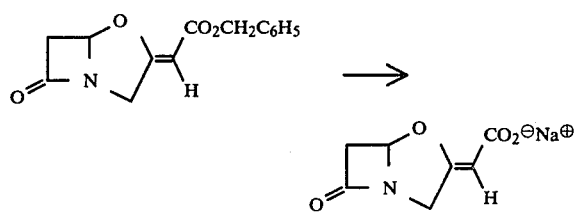

(Z)-3-(Benzyloxycarbonylmethylene)-4-oxa-1-azabicyclo-[3.2.0]heptan-7-one (100 mg) was converted into the title compound using the process described in Example 7. The title compound was obtained as a colourless amorphous powder (65 mg.), $\lambda_{max}$ (KBr): 1785 ($\beta$-lactam C=O), 1670 (olefinic C=C), 1565 and 1410 (carboxylate) cm$^{-1}$. $\delta$(D$_2$O): 2.95 (d, J 17 Hz, 1H, C(6)H), 3.37 (dd, 17, J' 2 Hz, 1H, C(6)H), 3.57 (d, J 16 Hz, 1H, C(2)H), ca 4.5 (part obscured by HOD, C(2)H), 4.85 (s, 1H, olefinic H), 5.58 (d, J 2 Hz, 1H, C(5)H).

EXAMPLE 75

(E)-3-[N-(Benzyloxycarbonylmethyl)carbamoylmethylene]-4-oxa-1-azabicyclo[3.2.0]heptan-7-one

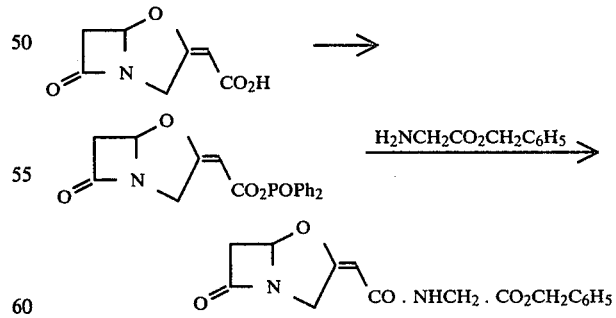

(E)-7-Oxo-4-oxa-1-azabicyclo[3.2.0]heptane-3-methylenecarboxylic acid (0.5 mmole) and glycine benzyl ester (0.5 mmole) (obtained from the p-toluenesulphonate salt by treatment with excess sodium carbonate in water/ether) were converted into the title compound using the process described in Example The title compound was obtained as a colourless gum (22 mg.). $\lambda_{max}$ (EtOH): 234 nm (ε 19,500). $v_{max}$ (CHCl$_3$): 3400 and 3300 (amide NH), 1800 (β-lactam C=O), 1740 (ester C=O), 1680 (amide C=O), 1630 (olefinic C=C), 1510 (amide II band) cm$^{-1}$. ε (CDCl$_3$) 2.99 (d, J 16 Hz, 1H, C(6)H), 3.43 (dd, J 16, J' 2 Hz, 1H, C(6)H), 3.90 (dd, J 18, J' 1 Hz, 1H; C(2)H), 4.05 (d, J 5 Hz, 2H, NCH$_2$), 5.08 (dd, J 18, J' 1 Hz, 1H, C(2)H), 5.12 (s, 2H, OCH$_2$Ar), 5.42 (t, J 1 Hz, 1H, olefinic H), 5.48 (d, J 2 Hz, 1H, C(5)H), 5.98 (br.t, 1H, NH), 7.28 (s, 5H, Ar-H).

EXAMPLE 76

N-[(E)-7-Oxo-4-oxa-1-azabicyclo[3.2.0]heptane-3-methylene-carbonyl]glycine sodium salt

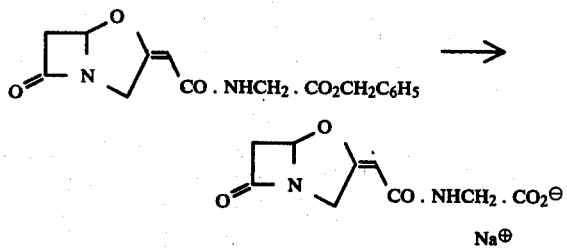

(E)-3-[N-(Benzyloxycarbonylmethyl)carbamoylmethylene]-4-oxa-1-azabicyclo[3.2.0]heptan-7-one (13 mg) was converted into the title compound using the process described in Example 9. The title compound was obtained as a colourless amorphous powder (9 mg). $\lambda_{max}$ (water): 237 nm (ε 15,000). $v_{max}$ (KBr): 1785 (β-lactam C=O), 1680 (amide C=O), 1620 (olefinic C=C), 1540 (sh) (amide II band), 1560 and 1400 (carboxylate) cm$^{-1}$.

EXAMPLE 77

(E)-3-[N-((R)-1-Benzyloxycarbonylbenzyl)carbamoylmethylene]-4-oxa-1-azabicyclo[3.2.0]heptan-7-one

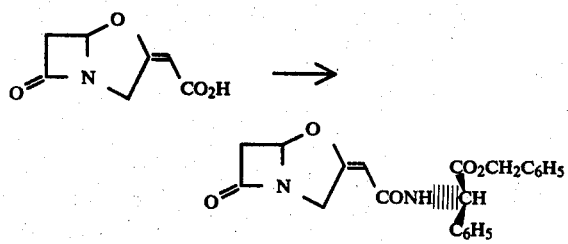

(E)-7-Oxo-4-oxa-1-azabicyclo[3.2.0]heptane-3-methylenecarboxylic acid (1 mmole) and R-α-phenylglycine benzyl ester (1 mmole) were converted into the title compound using the process described in Example 51. The title compound was obtained as a colourless gum (100 mg.) $[\alpha]_D^{22} = -86.5°$ (c=0.9, CHCl$_3$). $\lambda_{max}$ (EtOH): 225 nm (ε 16,800). $v_{max}$ (CHCl$_3$): 1800 (β-lactam C=O), 1740 (ester C=O), 1675 (amide C=O), 1625 (olefinic C=C), 1500 (amide II band) cm$^{-1}$ ε(CDCl$_3$): 2.94 and 2.95 (both d, J=17 Hz, 1H, C(6)H), 3.42 (dd, J 17, J' 2 Hz, 1H, C(6)H), 3.87 (br. d, J=18 Hz, 1H, C(2)H), 5.02 (br.d, J=18 Hz, 1H, C(2)H), 5.10 (s, 2H, OCH$_2$Ar), 5.45 (m, 2H, olefinic H and C(5)H), 5.58 (d, J=6 Hz, 1H, NCHPh), 6.37 (br. d, J=6 Hz, 1H, NH), 7.25 (narrow m, 10H, Ar-H).

EXAMPLE 78

(R)-N-[(E)-7-Oxo-4-oxa-1-azabicyclo[3.2.0]heptane-3-methylenecarbonyl]-α-phenylglycine sodium salt

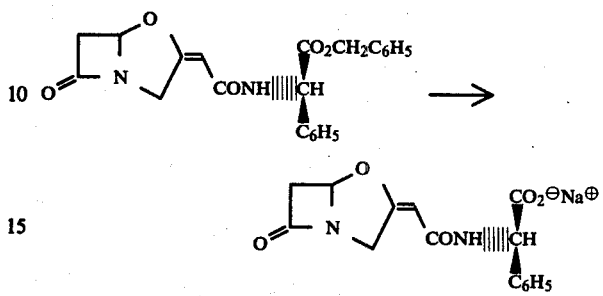

(E)-3-[N-((R)-1-Benzyloxycarbonylbenzyl)carbamoylmethylene]-4-oxa-1-azabicyclo[3.2.0]heptan-7-one (75 mg.) was converted into the title compound using the process described in Example 9. The title compound was obtained as a colourless amorphous powder (57 mg.). δ(D$_2$O): 2.98 and 3.00 (both d, J=17 Hz, 1H, C(6)H), 3.42 (dd, J 17, J' 2 Hz), 1H C(6)H), 3.84 (d, J=18 Hz, 1H, C(2)H), 5.05 (d, J 18 Hz, 1H, C(2)H), 5.09 (s, 1H, NCHPh), 5.55 (br.s, 2H, olefinic H and C(5)H), 7.27 (s, 5H, Ar-H).

EXAMPLE 79

(Z)-3(1-Methoxycarbonyl-2-phenylsulphonyl-1,1-ethylidene)-4-oxa-1-azabicyclo[3.2.0]-heptan-7-one

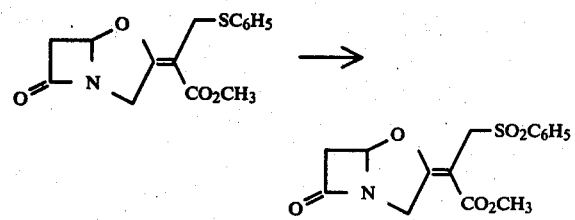

(Z)-3-(1-Methoxycarbonyl-2-phenylthio-1,1-ethylidene)-4-oxa-1-azabicyclo[3.2.0]heptan-7-one (40 mg., 0.13 mmole) was dissolved in dry methylene chloride (2 ml) and the solution was stirred and ice-cooled while a solution of m-chloroperbenzoic acid (35 mg., 0.2 mmole) in methylene chloride (1 ml) was added dropwise. After addition was complete, the mixture was stirred and ice-cooled with exclusion of moisture for 20 minutes. The mixture was diluted with ethyl acetate (30 ml) and was washed once with saturated sodium bicarbonate solution (10 ml.) and once with saturated brine (10 ml). The solution was dried and the solvent was evaporated under reduced pressure to yield a colourless gum. The gum was chromatographed on silica gel (10 g) using ethyl acetate/petroleum ether (b.p. 60°-80°) to give the title compound as a colourless gum (20 mg). (Found: M+, 337.06148. C$_{15}$H$_{15}$NO$_6$S requires 337.06200). $\lambda_{max}$ (EtOH): 243 nm (ε15,600) $v_{max}$ (CHCl$_3$): 1797 (β-lactam C=O), 1705 (ester C=O), 1640 (olefinic C=C), 1140 (sulphone)cm$^{-1}$. m/e: 337 (M, 0.12%), 306 (0.08), 250 (19), 218 (17), 196 (100), 164 (15), 154 (35), 127 (81), 125 (34).

EXAMPLE 80

(E)-3-(2-Formyloxy-1-methoxycarbonyl-1,1-ethylidene)-4-oxa-1-azabicyclo[3.2.0]-heptan-7-one

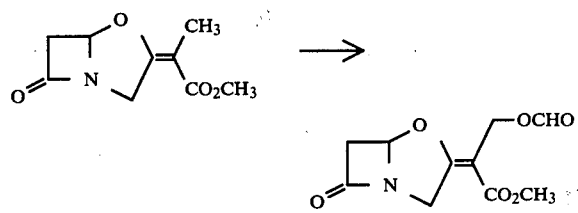

(E)-3(1-Methoxycarbonyl-1,1-ethylidene)-4-oxa-1-azabicyclo[3.2.0]-heptan-7-one (100 mg., 0.5 mmole) and 1,3-dibromo-5,5-dimethylhydantoin (75 mg., 0.26 mmole) were dissolved in dry carbon tetrachloride (6 ml) and α,α'-azoisbutyronitrile (4 mg) was added to the solution. The solution was refluxed and irradiated with white light (tungsten lamp) with exclusion of moisture. After 25 minutes a colourless precipitate started to develope in the solution. One minute after this precipitate started the mixture was cooled to room temperature. The mixture was concentrated to ca 0.5 ml. by evaporation of solvent under reduced pressure and was then diluted with dry 1,2-dimethoxyethane (2 ml). This solution was added to a stirred, ice-cooled solution of potassium formate (170 mg) in dry dimethylformamide. After addition, the cooling bath was removed and the mixture was stirred at room temperature for 4 hours. The mixture was diluted with ethyl acetate (30 ml) and was washed three times with water (10 ml. portions). The solution was dried and the solvent was removed to yield a yellow gum (150 mg) The gum was chromatographed on silica gel (15 g.) using ethyl acetate/petroleum ether (b.p. 60°–80°) to give the title compound as a colourless gum (27 mg.) (Found: M+, 241.05880. $C_{10}H_{11}NO_6$ requires 241.05863). $\lambda_{max}$ (EtOH): 236 nm (ε=14,100). $\nu_{max}$(CHCl$_3$): 1800 (β-lactam C=O), 1720 (sh.) (ester C=O), 1710 (ester C=O), 1645 (olefinic C=C). δ(CDCl$_3$): 3.11 (d, J 17 Hz, 1H, C(6)H), 3.55 (dd, J 17, J' 2 Hz, 1H, C(6)H), 3.72 (s, 3H, OCH$_3$), 3.96 (d, J 18 Hz, 1H, C(2)H), 4.96 (s, 2H,OCH$_2$), 5.07 (d, J 18 Hz, C(2)H), 5.69 (d, J 2 Hz, 1H, C(5)H), 8.00 (s, 1H, CHO). m/e: 241 (M+, 5%), 213 (2), 210 (3), 196 (50), 185 (20), 164 (12), 153 (100), 139 (30), 127 (90), 113 (33).

EXAMPLE 81

(E)-3-(2-Hydroxy-1-methoxycarbonyl-1,1-ethylidene)-4-oxa-1-azabicyclo[3.2.0]heptan-7-one

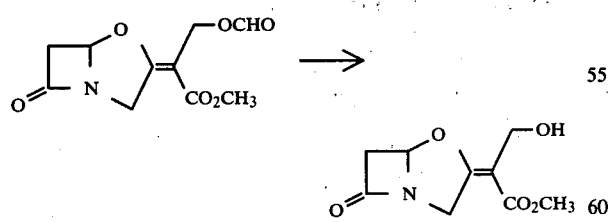

(E)-3-(2-Formyloxy-1-methoxycarbonyl-1,1-ethylidene)-4-oxa-1-azabicyclo[3.2.0]heptan-7-one (15 mg.) was dissolved in dry methanol (3 ml) and a saturated solution of potassium formate in methanol (0.5 ml) was added. The mixture was stirred at room temperature for 6 hours at which time thin layer chromatography showed that all of the starting material had been consumed. The mixture was diluted with dry benzene (50 ml) and was filtered. Evaporation of the solvent from the filtrate gave the title compound as a pale yellow gum (8 mg.). (Found: M+, 213.0644. $C_9H_{11}NO_5$ requires 213.0638). $\nu_{max}$ (CHCl$_3$): 3500 and 3250 (br.) (hydroxyl OH), 1800 (β-lactam C=O), 1705 and 1690 (ester C=O), 1645 (olefinic C=C)cm$^{-1}$. δ(CDCl$_3$): 3.06 (d, J 16 Hz, 1H, C(6)H), 3.48 (dd, J 16, J' 2 Hz, C(6)H), 3.73 (s, 3H, OCH$_3$), 3.88 (d, J 18 Hz, 1H, C(2)H), 4.38 (s, 2H, CH$_2$O), 4.98 (d, J 18 Hz, 1H, C(2)H), 5.62 (d, J 2 Hz, 1H, C(5)H), m/e: 213 (M+, 27%), 185 (17), 182 (21), 157 (100), 153 (72), 139 (86).

EXAMPLE 82

(Z)-3-(2-Hydroxyethylidene)-4-oxa-1-azabicyclo[3.2.0]-heptan-7-one

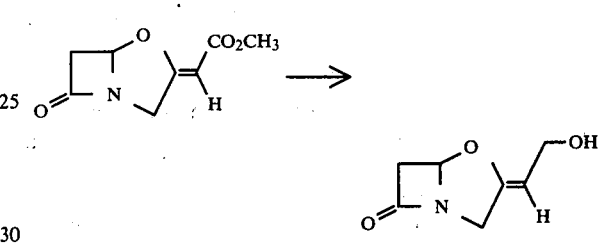

(Z)-3-Methoxycarbonylmethylene-4-oxa-1-azabicyclo[3.2.0]-heptan-7-one (120 mg., 0.65 mmole) was dissolved in dry 1,2-dimethoxyethane (5 ml.)/dry toluene (5 ml.) and the solution was stirred at −30° under a dry nitrogen atmosphere while a 20% solution of di-isobutyl aluminium hydride in toluene (0.5 ml.) was added dropwise. After addition was complete, the mixture was stirred at −30° to −10° for 1 hour. Methanol (1 ml.) was added to the solution which was then diluted with ethyl acetate (30 ml). The solution was washed once with saturated brine to which a few drops of 2 N. HCl had been added. The solution was dried and the solvent was evaporated under reduced pressure to yield a yellow gum. The gum was chromatographed on silica gel (10 g.) using ethyl acetate/petroleum ether (b.p. 60°–80°) to give the title compound as a colourless oil (5 mg.). $\nu_{max}$ (CHCl$_3$): 3350 (hydroxyl OH), 1793 (β-lactam C=O), 1695 (olefinic C=C)cm$^{-1}$. δ (CDCl$_3$): 2.95 (d, J 16 Hz, 1H, C(6)H), 3.38 (dd, J 16, J' 2 Hz, 1H, C(6)H). 3.56 (d, 17 Hz, 1H, C(2)H), 4.18 (d, 7 Hz, 2H, CH$_2$O), 4.52 (d, J 17 Hz, 1H, C(2)H), 4.60 (t, J 7 Hz, 1H, olefinic H), 5.47 (d, J 2 Hz, 1H, C(5)H).

EXAMPLE 83.1

2,3-Benzylidenedioxypropyl 4-(4-methylthio-2-oxoazatidin-1-yl)-3-oxobutyrate

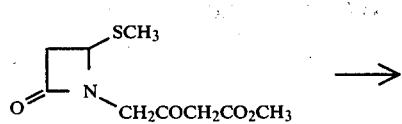

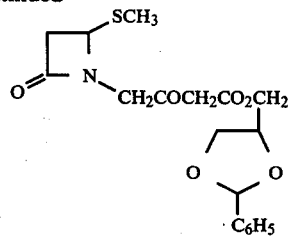

Methyl 4-(4-methylthio-2-oxoazetidin-1-yl)-3-oxobutyrate (460 mg., 2 mmole) and 2,3-benzylidenedioxypropanol (1.0 g.) were converted into the title compound using the process described in Example 6.1. The title compound was obtained as a colourless gum (465 mg.) $\nu_{max}$ (CHCl$_3$): 1760 ($\beta$-lactam C=O), 1740 (sh.), (keto-ester C=O)cm$^{-1}$. $\delta$ (CDCl$_3$): 2.00 (s, 3H, SCH$_3$), 2.97 (dd, J 16, J' 2 Hz, 1H, $\beta$-lactam CHH), 3.45 (dd, J 16, J' 5 Hz, 1H, $\beta$-lactam CHH), 3.53 and 3.59 (both s, 2H, COCH$_2$CO), 3.65–4.70 (complex, 7H, NCH$_2$CO, OCH$_2$,OCH$_2$,OCH 4.87 (m, 1H, $\beta$-lactam CH), 5.86 and 5.99 (both s, 1H, OCH(Ph)O), 7.40 (s, 5H, Ar-H).

EXAMPLE 83.2

(E)- and
(Z)-3-[(2,3-Benzylidenedioxy)propoxycarbonylmethylene]-4-oxa-1-azabicyclo[3.2.0]heptan-7-one and (Z)-3-[(2,3-benzylidenedioxy)propoxycarbonylchloromethylene]-4-oxa-1-azabicyclo[3.2.0]heptan-7-one

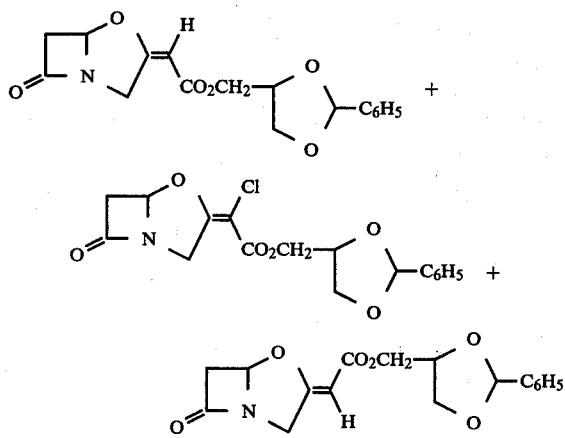

2,3-Benzylidenedioxypropyl 4-(4-methylthio-2-oxoazetidin-1-yl)-3-oxobutyrate (215 mg., 0.56 mmole) was subjected to the process described in Example 6.2. Chromatography of the crude product gave, in order of elution, the following compounds.

(Z)-3-[2,3-Benzylidenedioxy)propoxychloromethylene]-4-oxa-1-azabicyclo[3.2.0]heptan-7-one as a colourless gum (3 mg.). $\lambda_{max}$ (EtOH): 238.5 nm. $\nu_{max}$ (CHCl$_3$): 1803 ($\beta$-lactam C=O), 1710 (ester C=O), 1643 (olefinic C=C)cm$^{-1}$ (E)-3-[(2,3-Benxzylidenedioxy)propoxycarbonylmethylene]-4-oxa-1-azabicyclo[3.2.0]heptan-7-one as a colourless gum (64 mg.). (Found: M$^+$, 331.1046. C$_{17}$H$_{17}$NO$_6$ requires 331.1056 )$\lambda_{max}$(EtOH): 235.5 ($\delta$=17,000)nm. $\nu_{max}$(CHCl$_3$): 1800 ($\beta$-lactam C=O), 1710 (ester C=O), 1655 (olefinic C=C)cm$^{-1}$. $\epsilon$ (CDCl$_3$): 3.00 (d, J. 16 Hz, 1H, C(6)H), 3.43 (dd, J 16, J' 2 Hz, 1H, C(6)H), 3.6–4.6 (complex, 6H, CH$_2$O, CH$_2$O, CHO, C(2)H), 4.99 and 5.02 (both dd, J 18, J' 2 Hz, 1H, C(2)H), 5.48 (t, J 2 Hz, 1H, olefinic H), 5.53 (d, J 2 Hz, 1H, C(5)H), 5.74 and 5.88 (both s, 1H, OCH(Ph)O), 7.32 (s, 5H, Ar-H). m/e: 331 (M$^+$, 5%), 330(4). 302 (2), 247 (17), 225 (80), 198 (14), 183 (13), 179 (16), 162 (11), 152 (20), 149 (27), 110 (22), 105 (100), 91 (83).

(Z)-3-[(2,3-Benzylidenedioxy)propoxycarbonylmethylene]-4-oxa-1-azabicyclo[3.2.0]heptan-7-one was as a colourless gum (7 mg.). $\lambda_{max}$ (EtOH): 236 ($\epsilon$15,200)nm. $\nu_{max}$ (CHCl$_3$): 1800 ($\beta$-lactam C=O), 1710 (ester C=O), 1665 (olefinic C=C)cm$^{-1}$. m/e: 331 (M$^+$, 0.4%), 330 (0.8), 247 (3.5), 225 (3), 179 (100), 149 (16), 105 (20), 91 (26).

EXAMPLE 84

(E)-3-[(2,3-Dihydroxy)propoxycarbonylmethylene]-4-oxa-1-azabicyclo[3.2.0]heptan-7-one

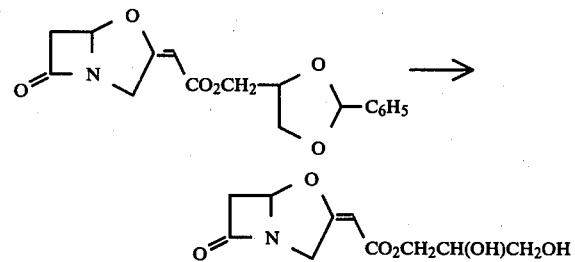

(E)-3-[(2,3-Benzylidenedioxy)propoxycarbonylmethylene]-4-oxa-1-azabicyclo[3.2.0]heptan-7-one (41 mg.) in tetrahydrofuran (2 ml.) was added to a mixture of 10% palladium-on-charcoal (50 mg.) and tetrahydrofuran (10 ml.) which had been shaken in a hydrogen atmosphere for 10 minutes. The mixture was shaken under one atmosphere of hydrogen at room temperature for 1 hour. More 10% palladium-on-charcoal (50 mg.) was added to the mixture and hydrogenation was continued for a further 30 minutes. The catalyst was removed by filtration and was washed with tetrahydrofuran. Evaporation of solvent from the filtrate yielded the title compound as a colourless gum (30 mg.). $\lambda_{max}$ (EtOH): 233.5 ($\epsilon$17,400)nm. $\nu_{max}$ (CHCl$_3$): 3350 (hydroxyl OH), 1800 ($\beta$-lactam C=O), 1705 (ester C=O), 1650 (olefinic C=C)cm$^{-1}$. $\delta$ (CDCl$_3$): 3.00 (br., 2H, OH), 3.05 (d, J 16.5 Hz, 1, C(6)H), 3.40–4.10 (complex, 5H, C(6)H), C(2)H, CH$_2$O, CHO), 4.15 (d, J 5 Hz, 2H, CH$_2$O), 5.02 (dd, J 18, J' 1 Hz, 1H, C(2)H), 5.47 (t, J 1 Hz, 1H, olefinic H), 5.59 (d, J 2 Hz, 1H, C(5)H).

EXAMPLE 85

Demonstration of Effectiveness a. Compounds of this invention were tested by conventional methods to determine their effect on the MIC (minimum inhibitory concentration) values of ampicillin against certain $\beta$-lactamase producing bacteria. The results for the compounds of the formula

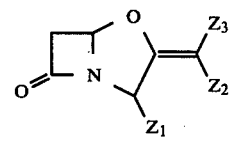

were as follows:

| Compound | | | MIC for Ampicillin (μg/ml) in presence of (5 μg/ml) of test compound | |
|---|---|---|---|---|
| $Z_1$ | $Z_2$ | $Z_3$ | Klebsiella E 70 | Staphylococcus aureus Russell |
| H | $CO_2Na$ | H | 16–31 | 100 |
| H | $CO_2CH_3$ | $CH_3$ | 16 | 0.8 |
| H | $CO_2Na$ | $CH_3$ | 1.56 | 1.56 |
| H | $CO_2Na$ | $C_6H_5$ | 3.1 | 1.56 |
| H | $CO_2CH_3$ | $CH_3$ | 1.56 | 0.4 |
| $CO_2Na$ | H | $C_6H_5$ | 8–16 | 0.2 |
| $CO_2CH_3$ | H | 3-thienyl | — | 0.3 |
| $CO_2Na$ | H | 3-thienyl | 8 | 0.1 |
| $CO_2Na$ | H | p-$C_6H_4OH$ | 3.1 | 0.6 |

The MICs of ampicillin in these tests against Klebsiella aerogenes E70 and Staph. aureus Russell were >2000, >2000 and 250 μg/ml respectively. The MICs of the synergist were >500, >500 and >62.5 μg/ml against these organisms.

b. The compounds of the invention do not have high acute toxicities, thus for example the compound wherein $Z_2$ is H, $Z_3$ is $C_6H_5$ and $Z_1$ is $CO_2Na$ did not cause any deaths in a group of mice when administered subcutaneously at 1000 mg/kg and the compound wherein $Z_1$ is H, $Z_2$ is $CO_2Na$ and $Z_3$ is $C_6H_5$ did not cause any deaths in a group of mice when administered subcutaneously at 250 mg/kg.

What we claim is:

1. A compound of the formula:

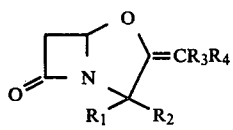

wherein $R_1$ and $R_2$ are each hydrogen; $R_3$ is lower alkyl, or phenyl unsubstituted or substituted by hydroxyl; $R_4$ is carboxylic acid, a pharmaceutically acceptable salt thereof, an unsubstituted amide thereof, α-ethoxycarbonyloxyethyl ester thereof, the phthalidyl ester thereof or an ester thereof of the formula —CO—O—$E_1$ or —CO—O—$CH_2E_2E_3$ wherein $E_1$ is a hydrocarbon of up to 8 carbon atoms unsubstituted or substituted by halogen or a moiety of the formula $OE_4$, $O.CO.E_4$, $SE_4$ or $SO_2E_4$ wherein $E_4$ is a hydrocarbon of up to 8 carbon atoms; $E_2$ is hydrogen, lower alkyl, phenyl or hydroxyphenyl; and $E_3$ is phenyl or hydrophenyl.

2. A compound according to claim 1 wherein $R_3$ is methyl, ethyl, n-propyl, phenyl or hydroxyphenyl.

3. A compound according to claim 1 in the form of a pharmaceutically acceptable salt.

4. A compound according to claim 1 in the form of a ester.

5. A compound according to claim 1 wherein $R_3$ is phenyl.

6. A compound according to claim 1 wherein $R_3$ is methyl, ethyl, or n-propyl.

7. A compound according to claim 6 wherein $R_3$ is methyl.

8. A salt according to claim 3 which is the lithium, sodium or potassium salt.

9. A salt according to claim 8 in crystalline form.

10. The compound according to claim 1 which is (E)-3-(1-methoxycarbonylethylidene)-4-oxa-1-azabioyclo[3.2.0]heptan-7-one.

11. The compound according to claim 1 which is (E)-3-(1-benzyloxycarbonylethylidene)-4-oxa-1-azabicyclo[3.2.0]heptan-7-one.

12. The compound according to claim 1 which is sodium(E)-7-oxo-4-oxa-1azabicyclo[3.2.0]heptane-3-(ethylidene-1-carboxylate).

13. The compound according to claim 1 which is sodium(E)-7-oxo-4-oxa-1-azabicyclo[3.2.0]heptane-3-(1,1-propylidene-1-carboxylate).

14. The compound according to claim 1 which is (E)-2-(1-benzyloxycarbonyl-1,1-n-butylidene)-4-oxa-1-aza-bicyclo[3.2.0]heptan-7-one.

15. The compound according to claim 1 which is sodium(E)-7-oxo-4-oxa-1-azabicyclo[3.2.0]heptane-3-(1,1-n-butylidene-1-carboxylate).

16. The compound according to claim 1 which is (E)-3-(1-benzyloxycarbonylbenzylidene)-4-oxa-1-azabicyclo[3.2.0]heptan-7-one.

17. The compound according to claim 1 which is sodium(E)-7-oxo-4-oxa-1-azabicyclo[3.2.0]heptane-3-(benzylidene-1-carboxylate).

18. The compound according to claim 1 which is (E)-3-(1-carbamoylbenzylidene)-4-oxa-1-azabicyclo[3.2.0]-heptan-7-one.

19. An ester according to claim 4 which is the lower alkyl, benzyl, p-methoxybenzyl, allyl, phthalidyl, pivaloyloxymethyl, acetoxymethyl, methoxymethyl or α-ethoxycabonyloxyethyl ester.

* * * * *